US009339519B2

(12) United States Patent
Ayares

(10) Patent No.: US 9,339,519 B2
(45) Date of Patent: May 17, 2016

(54) MULTI-TRANSGENIC PIGS FOR DIABETES TREATMENT

(75) Inventor: David Ayares, Blacksburg, VA (US)

(73) Assignee: Revivicor, Inc., Blacksburg, VA (US)

( * ) Notice: Subject to any disclaimer, the term of this patent is extended or adjusted under 35 U.S.C. 154(b) by 0 days.

(21) Appl. No.: 12/857,514

(22) Filed: Aug. 16, 2010

(65) Prior Publication Data

US 2011/0038841 A1    Feb. 17, 2011

Related U.S. Application Data

(60) Provisional application No. 61/234,150, filed on Aug. 14, 2009.

(51) Int. Cl.

| A01K 67/00 | (2006.01) |
|---|---|
| A01K 67/033 | (2006.01) |
| A61K 35/39 | (2015.01) |
| A01K 67/027 | (2006.01) |
| C12N 15/85 | (2006.01) |

(52) U.S. Cl.
CPC ............. *A61K 35/39* (2013.01); *A01K 67/0276* (2013.01); *A01K 67/0278* (2013.01); *C12N 15/8509* (2013.01); *A01K 2217/052* (2013.01); *A01K 2217/075* (2013.01); *A01K 2217/15* (2013.01); *A01K 2217/206* (2013.01); *A01K 2227/108* (2013.01); *A01K 2267/025* (2013.01); *A01K 2267/0362* (2013.01); *C12N 2830/40* (2013.01)

(58) Field of Classification Search
CPC ............................... A61K 35/39; A01K 67/00
See application file for complete search history.

(56) References Cited

U.S. PATENT DOCUMENTS

| 5,578,314 A | 11/1996 | Cochrum et al. |
| 5,821,117 A | 10/1998 | Sandrin et al. |
| 5,859,307 A | 1/1999 | Mombaerts et al. |
| 6,153,428 A | 11/2000 | Gustafsson et al. |
| 6,303,355 B1 | 10/2001 | Opara |
| 6,413,769 B1 | 7/2002 | Gustafsson et al. |
| 6,423,316 B1 | 7/2002 | Riesbeck et al. |
| 6,482,404 B1 | 11/2002 | White et al. |
| 6,495,735 B1 | 12/2002 | White et al. |
| 7,122,177 B2 | 10/2006 | Elliot et al. |
| 7,304,033 B2 | 12/2007 | Larsen et al. |
| 7,378,569 B2 | 5/2008 | Tu et al. |
| 7,432,344 B1 | 10/2008 | Lechler et al. |
| 8,097,598 B2 | 1/2012 | Lechler et al. |
| 2003/0014770 A1 | 1/2003 | Gustafsson et al. |
| 2003/0024002 A1 | 1/2003 | Colman et al. |
| 2005/0260176 A1 | 11/2005 | Ayares et al. |
| 2012/0090039 A1 | 4/2012 | Ayares et al. |

FOREIGN PATENT DOCUMENTS

| EP | 0495852 | 8/2008 |
| WO | WO 94/21799 | 9/1994 |
| WO | WO 95/20661 | 3/1995 |
| WO | WO 95/28412 | 10/1995 |
| WO | WO 99/57266 | 1/1999 |
| WO | WO 01/30966 | 3/2001 |
| WO | WO 03/055302 | 10/2003 |
| WO | WO 2004/016742 | 2/2004 |
| WO | WO 2004/028243 | 8/2004 |
| WO | WO 2007/035213 | 3/2007 |
| WO | WO 2007035213 | 3/2007 |

OTHER PUBLICATIONS

Rood, 2007,. Transplantation, 83:202-210.*
Cowan, 2007, Xenotransplantation, 14:7-12.*
Bischof Diabetes, 2001, 50:502-514.*
van der Windt, 2012, Diabetes, 61:3046-3055.*
Tai et al., Progress in xenotransplantation following the introduction of gene-knockout technology. Transplant International, 2007, vol. 20, pp. 107-117.
D'Apice et al., Gene-modified pigs. Xenotransplantation, 2008, vol. 15, pp. 87-90.
Yamaoka et al., Regeneration therapy of pancreatic b cells: towards a cure for diabetes? Biochemical and Biophysical Research Communications, 2002, vol. 296, pp. 1039-1043.
Bennet et al., Ups J Med Sci 2000, 105:125-133.
Cowan and D'Apice, Curr Opin Organ Transplant. Apr. 2008; 13(2):178-83).
Dai et al. (Nature Biotechnology 20: 251-255, 2002.
Dalmasso et al. Transplantation 52:530-533 (1991).
Dalmasso et al., Clin. Exp. Immunol. 86:31-35, 1991.
Denning et al. (Nature Biotechnology 19: 559-562, 2001.
Diamond, et al., Transpl Immunol. Dec. 1995; 3(4):305-12.
Dwyer et al. (2004) J Clin Invest 113: 1440-46.
Elayat et al. (1995). J. Anat. 186: 629-37).
Gerrish K et al., Mol. Endocrinol., 2004, 18(3): 533.
Harrison et al. (Transgenics Research 11: 143-150, 2002).
Johansson et al. Diabetes, 2005, 54:1755.
Lai et al. (Science 295: 1089-1092, 2002).
Lui et al. J Immunol Methods 2003 277:171-183.
Martin, et al. (2005) Transg. Rsch. 14:373-84.
Mirenda et. al., Diabetes 54:1048-1055, 2005.
Miyagawa et al. (J. Biol. Chem. 276, 39310 (2000).
Phelps et al. Science, 2003, 299:411-414.
Rood, et al. (2007) Transplantation 83:202-210.
Stone et al., Transplantation 63: 640-645, 1997.
Squinto, Curr Opin Biotechnol. Dec. 1996; 7(6):641-5.
Sutherland et al. Transplantation. 2000 69(9):1806-12.
Tanemura et al., J. Biol. Chem. 27321: 16421-16425, 1998 and.
Vaughn A. et al., J Immunol (2000) 3175-3181.
Ye et al., Transplantation 58: 330-337, 1994.

(Continued)

*Primary Examiner* — Valarie Bertoglio
(74) *Attorney, Agent, or Firm* — King & Spalding

(57) ABSTRACT

The present invention provides certain animals, and in particular porcine animals, tissue and cells derived from these, which lack any expression of functional alpha 1,3 galactosyltransferase (αGT) and express one or more additional transgenes which make them suitable donors for pancreatic islet xenotransplantation. Methods of treatment and prevention of diabetes using cells derived from such animals are also provided.

28 Claims, 9 Drawing Sheets

(56) References Cited

OTHER PUBLICATIONS

Cardona K, et al., Nat Med, 12:304-306. 2006.
Chen D, et al. Am J Transplant 2004; 4: 1958-1963.
Chuang et al., 2008; Martin et al., Endocr Dev. 2007; 12:24-32.
Costa et al. (FASEB J 13, 1762 (1999)).
Faideau et al., Diabetes. Dec. 2005; 54 Suppl 2:S87-96.
Flotte, J. of Cellular Physiology, 2007, 213:301-305.
Garcia-Ocana et al., Journal of Biol. Chem., 2003, 278:343-351.
Hering B J, et al., Nat Med, 12:301-303. 2006.
Iino et al., (J Thromb Haemost. May 2004; 2(5):833-4).
Lane et al. J Exp Med. Mar. 1, 1994; 179(3):819.
Otterbein L E et al., J Clin Invest 1999; 103: 1047-1054.
Poss K D et al., Proceedings of the National Academy of Sciences of the United States of America 1997; 94:10925-10930.
Poss K D et al., Proceedings of the National Academy of Sciences of the United States of America 1997; 94:10919-10924.
Sato K et al., J. Immunol. 2001; 166:4185-4194.
Shiraishi F et al., Am J Physiol Renal Physiol 2000; 278:F726-F736.
Sklavos et al., Diabetes. Jul. 2010; 59(7):1731-8. Epub Apr. 22, 2010.
Van de Wouwer et al., Arterioscler Thromb Vasc Biol. Aug. 2004; 24(8):1374-83.
Venstrom et al. 2003; 290:2817-2823.
Yachie A et al., Journal of Clinical Investigation 1999; 103:129-135.
Yet S F, et al., Cir Res 2001; 89:168-173.
Van der Windt American Journal of Transplantation vol. 9, Issue 12, pp. 2716-2726, Dec. 2009.
Loveland et al. "Characterization of a CD46 Transgenic Pig and Protection of Transgenic Kidneys Against Hyperacute Rejection in Non-Immunosuppressed Baboons." Xenotrasplantation. 2004: 11: 171-183.
Petersen B et al: "The perspectives for porcine-to-human xenografts", Comparative Immunology, Microbiology and Infectious Diseases. Pergamon Press, Oxford, GB, vol. 32, No. 2, Mar. 1, 2009.
Cozzi et al: "On the road to clinical xenotransplantation". Transplant Immunology, Elsevier, NL, vol. 21, No. 2, Jun. 1, 2009.
Smith RM et al: "Pancreatic islet xenotransplantation: the potential for tolerance induction", Immunology Today, Elsevier Publications, Cambridge, GB, vol. 21, No. 1, Jan. 1, 2000.
Leventhal Joseph R et al: "Evidence that tilapia islets do not express alpha-(1,3)gal: implications for islet xenotransplantation". Xenotransplantation, vo 1 . 11, No. 3, May 2004.

* cited by examiner hCD46 hTFPI hIgG1 / pCTLA4 hCD39 insulin

SEQUENCE LISTING

```
<160> NUMBER OF SEQ ID NOS: 17

<210> SEQ ID NO 1
<211> LENGTH: 34
<212> TYPE: DNA
<213> ORGANISM: Artificial Sequence
<220> FEATURE:
<223> OTHER INFORMATION: Synthesized

<400> SEQUENCE: 1
gacgagatct accaaatcag gaacagaaag agtc                                34

<210> SEQ ID NO 2
<211> LENGTH: 34
<212> TYPE: DNA
<213> ORGANISM: Artificial Sequence
<220> FEATURE:
<223> OTHER INFORMATION: Synthesized

<400> SEQUENCE: 2
tatcaagctt acctgcttgc tgatggtttc cgac                                34

<210> SEQ ID NO 3
<211> LENGTH: 34
<212> TYPE: DNA
<213> ORGANISM: Artificial Sequence
<220> FEATURE:
<223> OTHER INFORMATION: Synthesized

<400> SEQUENCE: 3
actgagatct tctagagagt tcttctgttt gcta                                34

<210> SEQ ID NO 4
<211> LENGTH: 34
<212> TYPE: DNA
<213> ORGANISM: Artificial Sequence
<220> FEATURE:
<223> OTHER INFORMATION: Synthesized

<400> SEQUENCE: 4
gctcggatcc ttaaaggtaa atgaattta tata                                 34

<210> SEQ ID NO 5
<211> LENGTH: 30
```

-continued

```
<212> TYPE: DNA
<213> ORGANISM: Artificial Sequence
<220> FEATURE:
<223> OTHER INFORMATION: Synthesized

<400> SEQUENCE: 5
attaatcgat gggacagccc cccccaaag                                    30

<210> SEQ ID NO 6
<211> LENGTH: 34
<212> TYPE: DNA
<213> ORGANISM: Artificial Sequence
<220> FEATURE:
<223> OTHER INFORMATION: Synthesized

<400> SEQUENCE: 6
atattctaga ttttccccgt atcccccag gtgt                               34

<210> SEQ ID NO 7
<211> LENGTH: 30
<212> TYPE: DNA
<213> ORGANISM: Artificial Sequence
<220> FEATURE:
<223> OTHER INFORMATION: Synthesized

<400> SEQUENCE: 7
attaactagt gggacagccc cccccaaag                                    30

<210> SEQ ID NO 8
<211> LENGTH: 34
<212> TYPE: DNA
<213> ORGANISM: Artificial Sequence
<220> FEATURE:
<223> OTHER INFORMATION: Synthesized

<400> SEQUENCE: 8
atatatcgat ttttccccgt atcccccag gtgt                               34

<210> SEQ ID NO 9
<211> LENGTH: 19
<212> TYPE: DNA
<213> ORGANISM: Artificial Sequence
<220> FEATURE:
<223> OTHER INFORMATION: Synthesized

<400> SEQUENCE: 9
agcaaagtcc aggggtcag                                               19

<210> SEQ ID NO 10
<211> LENGTH: 22
<212> TYPE: DNA
<213> ORGANISM: Artificial Sequence
<220> FEATURE:
<223> OTHER INFORMATION: Synthesized

<400> SEQUENCE: 10
gaaatctggc ttttcttgtt gc                                           22

<210> SEQ ID NO 11
<211> LENGTH: 515
<212> TYPE: DNA
<213> ORGANISM: Artificial Sequence
<220> FEATURE:
<223> OTHER INFORMATION: Synthesized

<400> SEQUENCE: 11
```

```
ggattgtgtc gtgccaatga gaacagattc tactacaatt cagtcattgg gaaatgccgc    60
ccatttaagt acagtggatg tgggggaaat gaaaacaatt ttacttccaa acaagaatgt   120
ctgagggcat gtaaaaaagg tttcatccaa agaatatcaa aaggaggcct aattaaaacc   180
aaaagaaaaa gaaagaagca gagagtgaaa atagcatatg aagaaatttt tgttaaaaat   240
atctgcagga accagaagaa ggtggaattc aaaatagaca tcgtggtgct agctttccag   300
aaggcctcca gcatagtcta taagaaagag ggggaacagg tggagttctc cttcccactc   360
gcctttacag ttgaaaagct gacgggcagt ggcgagctgt ggtggcaggc ggagagggct   420
tcctcctcca gtcttggat caccttgac ctgaagaaca aggaagtgtc tgtaaaacgg    480
gttacccagg accctaagct ccagatgggc aagaa                             515
```

<210> SEQ ID NO 12
<211> LENGTH: 23
<212> TYPE: DNA
<213> ORGANISM: Artificial Sequence
<220> FEATURE:
<223> OTHER INFORMATION: Synthesized

<400> SEQUENCE: 12

```
cgctgtgggc tcttctctta cat                                           23
```

<210> SEQ ID NO 13
<211> LENGTH: 22
<212> TYPE: DNA
<213> ORGANISM: Artificial Sequence
<220> FEATURE:
<223> OTHER INFORMATION: Synthesized

<400> SEQUENCE: 13

```
gagcaagcca tggctaagct ta                                            22
```

<210> SEQ ID NO 14
<211> LENGTH: 474
<212> TYPE: DNA
<213> ORGANISM: Artificial Sequence
<220> FEATURE:
<223> OTHER INFORMATION: Synthesized

<400> SEQUENCE: 14

```
cgctgtgggc tcttctctta catgtacctt ttgctagcct caaccctgac tatcttccag    60
gtcattgttc caacaagctt tattgcggta gtttatcaca gttaaattgc taacgcagtc   120
agtgcttctg acacaacagt ctcgaactta agctgcagtg actctcttaa ggtagccttg   180
cagaagttgg tcgtgaggca ctgggcaggt aagtatcaag gttacaagac aggtttaagg   240
agaccaatag aaactgggct tgtcgagaca gagaagactc ttgcgtttct gataggcacc   300
tattggtctt actgacatcc actttgcctt tctctccaca ggtgtccact cccagttcaa   360
ttacagctct taaggctaga gtacttaata cgactcacta taggctagcc tcgagaattc   420
acgcgtggta cctctagagt cgacggtatc gataagctta gccatggctt gctc         474
```

<210> SEQ ID NO 15
<211> LENGTH: 21
<212> TYPE: DNA
<213> ORGANISM: Artificial Sequence
<220> FEATURE:
<223> OTHER INFORMATION: Synthesized

<400> SEQUENCE: 15

```
catagaggcg aaattgcaga g                                             21
```

```
<210> SEQ ID NO 16
<211> LENGTH: 21
<212> TYPE: DNA
<213> ORGANISM: Artificial Sequence
<220> FEATURE:
<223> OTHER INFORMATION: Synthesized

<400> SEQUENCE: 16
agtatgggat tgtgctggat g                                              21

<210> SEQ ID NO 17
<211> LENGTH: 585
<212> TYPE: DNA
<213> ORGANISM: Artificial Sequence
<220> FEATURE:
<223> OTHER INFORMATION: Synthesized

<400> SEQUENCE: 17
agtatgggat tgtgctggat gcgggttctt ctcacacaag tttatacatc tataagtggc     60
cagcagaaaa ggagaatgac acaggcgtgg tgcatcaagt agaagaatgc agggttaaag    120
gtcctggaat ctcaaaattt gttcagaaag taaatgaaat aggcatttac ctgactgatt    180
gcatggaaag agctagggaa gtgattccaa ggtcccagca ccaagagaca cccgtttacc    240
tgggagccac ggcaggcatg cggttgctca ggatggaaag tgaagagttg gcagacaggg    300
ttctggatgt ggtggagagg agcctcagca actacccctt tgacttccag ggtgccagga    360
tcattactgg ccaagaggaa ggtgcctatg gctggattac tatcaactat ctgctgggca    420
aattcagtca gaaaacaagg tggttcagca tagtcccata tgaaaccaat aatcaggaaa    480
cctttggagc tttggacctt gggggagcct ctacacaagt cacttttgta ccccaaaacc    540
agactatcga gtccccagat aatgctctgc aatttcgcct ctatg                   585
```

MULTI-TRANSGENIC PIGS FOR DIABETES TREATMENT

RELATED APPLICATIONS

This non-provisional patent application claims priority under 35 U.S.C. §119 to U.S. Provisional Patent Application No. 61/234,150, titled "Multi-Transgenic Pigs for Diabetes Treatment," filed Aug. 14, 2009, the complete disclosure of which is hereby fully incorporated herein by reference.

FIELD OF THE INVENTION

The present invention provides certain donor animals, tissues and cells that are particularly useful for xenotransplantation therapies. In particular, the invention includes porcine animals, as well as tissue and cells derived from these, which lack any expression of functional alpha 1,3 galactosyltransferase (αGT) and express one or more additional transgenes which make these animals suitable donors for pancreatic islet xenotransplantation. Methods of treatment and prevention of diabetes using tissues and cells derived from such animals are also provided.

BACKGROUND OF THE INVENTION

Diabetes

Insulin is a hormone produced by the pancreas that moves sugar from the bloodstream into the cells of the body, where it becomes an essential energy source. In mammals, insulin is synthesized in the pancreas within the beta cells (β-cells) of the islets of Langerhans (pancreatic islets). There are about one million islets in a healthy adult human pancreas (about 1-2% of the total mass of the pancreas), which are distributed throughout the organ Diabetes is a disease state characterized by abnormally high levels of sugar (hyperglycemia) in the blood, either because the body does not produce enough insulin (Type 1 diabetes) or because the body cannot respond to the insulin that is produced (Type 2 diabetes). Uncontrolled, hyperglycemia can lead to serious complications including blindness, heart disease, kidney disease and even death.

In the United States alone, more than 20 million people have diabetes. Type 2 diabetes (T2D) is by far the most common type, and is associated with lack of physical activity and obesity. According to statistics compiled by the World Health Organization (WHO), in 2007, over 180 million people world wide have diabetes, resulting in 2.9 million deaths (6% of total global mortality), and associated with a total economic burden of more than $230 billion.

Type 1 diabetes (T1D) is far less common than T2D. It is an autoimmune disease in which the patient's own immune system destroys the body's insulin-producing pancreatic beta cells. Typically diagnosed at a young age, it is a chronic disease that requiring life-long treatment. Treatment is generally in the form of insulin replacement therapy, which is typically delivered by injection or pump. Successful insulin management depends on how closely a given regimen can mimic normal physiologic insulin release patterns. There are several different forms of insulin available, and the choice of a particular form/regime may reflect that patient's preferences and ability to adhere to a particular treatment regime. Despite advances in the pharmacology and delivery of insulin, achieving tight glycemic control using insulin replacement therapy can be very demanding. As a result, many T1D patients still experience episodes of hyper- and hypo-glycemia and suffer long term complications as a result.

Given the burdens of insulin replacement therapy, therapeutic alternatives are highly desirable. Transplanted human pancreases (allografts) offer a potential cure for T1D patients. Sources include human donors that have recently deceased or living donors (partial pancreas transplant). The recipient's native pancreas is generally left in place, and the donated pancreas is attached in a different location. Challenges include the risks inherent in any surgical procedure as well the possibility of rejection common to most transplanted organs. Rejection of the allograft pancreas may occur at any time from within seconds (acute) to years (chronic) after transplantation. To avoid rejection, immunosuppressive drugs must be taken indefinitely. These drugs can be difficult to tolerate, leave the patient at increased risk for infectious disease and have also been linked to high blood pressure, kidney problems and liver disorders. The risks of transplantation and the extended use of immunosuppressive drug therapy are uniquely problematic for diabetic patients (i.e., compared to other organ transplant recipients), as drug therapy generally remains an option, however undesirable. A 2003 study found that for patients with functioning kidneys, survival rates of patients who receive pancreas-only transplants were worse than the survival rates of patients who manage their diabetes with conventional therapy (Venstrom et al. 2003; 290:2817-2823). As a result, pancreas transplantation is normally only performed on individuals with type 1 diabetes with end-stage renal disease.

Transplant of only the islet cells (versus the entire pancreas) provides a less invasive transplant-based alternative. Here, islets are isolated from the donor pancreas and injected into the patient via a catheter to the portal vein (i.e., no requirement for a major abdominal incision). The islets travel to the liver where they become fixed, taking over insulin production and essentially turning the liver into a replacement pancreas. Early islet transplants had very low success rates, however, and patients remained insulin-independent for only short periods of time. The major differences between the Edmonton Protocol and those early islet transplant procedures was the use of a particular combination of immunosuppressive drugs and transplant of islets from more than one pancreas. Specifically, the Edmonton protocol uses a combination of immunosuppressive drugs that includes daclizumab, sirolimus and tacrolimus Daclizumab is given intravenously immediate post-transplant and then discontinued. The patient is then given sirolimus and tacrolimus indefinitely.

Both whole pancreas and islet transplant procedures depend on a reliable supply of human pancreas donors, which doesn't currently exist. At present, only 3000 cadaver pancreases become available each year, far short of those needed for the 2 million plus patients with T1D.

Gene therapy presents another therapeutic alternative. The introduction and expression of transgenes in human pancreatic islets to prevent immune rejection and improve proliferation and survival of islet grafts has been the focus of much research (review by McCabe et al., Diabetes Metab Res Rev. 2006 May-June; 22(3):241-52; Chuang et al., 2008; Martin et al., Endocr Dev. 2007; 12:24-32; Faideau et al., Diabetes. 2005 December; 54 Suppl 2:S87-96). Transgene delivery via ex-vivo transduction of human islets has been investigated (Garcia-Ocana et al., Journal of Biol. Chem., 2003, 278:343-351; Li et al., Transplantation Proceedings, 39:3436-3437). However, the immunomodulatory gene expression in these systems was insufficient for long term diabetic control as adenovirally infected islet grafts were rejected in about one month (see Sakata et al., Diabetes Research and Clinical Practice, 2008, 80:352-359). In addition, adenoviral vectors used for gene therapy in humans are limited in their capacity to deliver certain genes and have triggered immune responses and even caused one death (Flotte, J. of Cellular Physiology, 2007, 213:301-305). The efficiency of alternative, non-viral gene delivery systems has been low and transient. Genetic modification of human pancreatic cells has therefore failed to effectively address the needs of T1D patients.

Xenotransplantation

Xenotransplantation (transplant of organs, tissues and cells from a donor of a different species) could effectively address the shortage of human donor pancreases. Xenotransplants are also advantageously (i) supplied on a predictable, non-emergency basis; (ii) produced in a controlled environment; and (iii) available for characterization and study prior to transplant.

Depending on the relationship between donor and recipient species, the xenotransplant can be described as concordant or discordant. Concordant species are phylogenetically closely related species (e.g., mouse to rat). Discordant species are not closely related (e.g., pig to human). Pigs have been the focus of most research in the xenotransplanation area, since the pig shares many anatomical and physiological characteristics with human. Pigs also have relatively short gestation periods, can be bred in pathogen-free environments and may not present the same ethical issues associated with animals not commonly used as food sources (e.g., primates).

Scientific knowledge and expertise in the field of pig-to-primate xenotransplantation has grown rapidly over the last decade, resulting in the considerably prolonged survival of primate recipients of lifesaving porcine xenografts. (Cozzi et al., Xenotransplantation, 16:203-214. 2009). Recently, significant achievements have been reported in the field of islet xenotransplantation (Hering B J, et al., Nat Med, 12:301-303. 2006; Cardona K, et al., Nat Med, 12:304-306. 2006; Gianello P and Dufrane D., Xenotransplantation, 14: 441. 2007), and this progress has prompted to may to suggest that islets, and not solid organs, may be the first type of transplant in future clinical xenotransplantation trials.

Genetic Modification

While advantageous in many ways, xenotransplantation also creates a more complex immunological scenario than allotransplantation. As such, considerable effort has been directed at addressing the immune barrier through genetic modification (van der Windt et al., Xenotransplantation. 2007 July; 14(4):288-97, Cowan and D'Apice, Curr Opin Organ Transplant. 2008 April; 13(2):178-83).

Xenograft rejection can be divided into three phases: hyperacute rejection, acute humoral xenograft rejection, and T cell-mediated cellular rejection. Hyperacute rejection (HAR) is a very rapid event that results in irreversible graft damage and loss within minutes to hours following graft reperfusion. It is triggered by the presence of xenoreactive natural antibodies present within the recipient at the time of transplantation. Humans have a naturally occurring antibody to the alpha 1,3-galactose (Gal) epitope found on pig cells. This antibody is produced in high quantity and, it is now believed, is the principle mediator of HAR. (Sandrin et al., Proc Natl Acad Sci USA. 1993 Dec. 1; 90(23):11391-5, 1993; review by Sandrin and McKenzie, Immunol Rev. 1994 October; 141:169-90). Initial efforts to genetically modify pigs have focused on removing the alpha 1,3-galactose (Gal) epitope from pig cells. In 2003, Phelps et al. (Science, 2003, 299:411-414) reported the production of the first live pigs lacking any functional expression of αGT (GTKO), which represented a major breakthrough in xenotransplantation (see also PCT publication No. WO 04/028243 to Revivicor, Inc. and PCT Publication No. WO 04/016742 to Immerge Biotherapeutics, Inc.). Subsequent studies have shown that organ grafts from GTKO pigs do not undergo HAR (Kuwaki et al., Nat. Med. 2005 January; 11(1):29-31, Yamada et al., Nat. Med. 2005 January; 11(1):32-4). Although Gal-mediated HAR is now known to be a significant factor in xenotransplantation of whole organs.

It is not clear if HAR is also a critical factor in adult islet xenotransplantation as pure populations of pancreatic beta cells from adult pigs do not express significant levels of the immunogenic Gal epitope. Indeed, in one study, it was found that GTKO pig pancreatic islets were no less susceptible to destruction than wild type islets (Rood, et al. (2007) Transplantation 83:202-210). However, unlike adult islets, fetal and neonatal islets do express Gal.

Expression of complement regulators in xenotransplant tissue has been suggested as a different strategy to combat HAR (Squinto, Curr Opin Biotechnol. 1996 December; 7(6): 641-5). European patent 0495852 to Imutran suggests associating xenograft tissues with recipient complement restriction factors to reduce complement activation in the recipient (see also Diamond, et al., Transpl Immunol. 1995 December; 3(4):305-12). Transgenic pigs expressing human DAF (hDAF) and/or human CD59 (hCD59) have been reported (Byrne et al., Transplant Proc., 1996 April; 28(2):758). CD46 has been expressed in pig cells using a minigene that was optimized for high ubiquitous expression and appears to protect porcine cells in a mouse transplantation model (Loveland et al., Xenotransplantation, 2004, 11:171:183; McKenzie et al., Xenotransplantation. 2003 November; 10(6):615-21). However, expression of these factors has been variable and generally very low in pancreatic cells (see Bennet et al., Transplantation, 2001, 72:312-319).

Even where HAR is avoided, the xenograft undergoes a delayed form of rejection, acute humoral xenograft rejection (AHXR)— also referred to as delayed xenograft rejection (DXR). It is generally thought to be initiated by xenoreactive antibodies, including non-Gal antibodies and subsequent activation of the graft endothelium, the complement and the coagulation systems (Miyagawa et al. Xenotransplantation, 2010, 1: 11-25).

Although the threats presented by the humoral response are critical with regard to the survival and function of vascularized grafts, the risk of graft damage by cellular mechanisms is also important. T-cell mediated acute responses play an important role in xenotransplant rejection, although their role in transplantation of pancreatic islet cells has not been fully elucidated. Of several T cell costimulatory pathways identified to date, the most prominent is the CD28 pathway and the related cytoxic T-lymphocyte associated protein (CTLA4) pathway.

To date, much of the research on CTLA4-Ig as an immunosuppressive agent has focused on administering soluble forms of CTLA4-Ig to a patient (see U.S. Pat. No. 7,304,033; PCT Publication No. WO 99/57266; and Lui et al. J Immunol Methods 2003 277:171-183). To reduce the overall immunosuppressive burden on a patient, transgenic expression of such a protein has been suggested. Transgenic mice expressing CTLA4-Ig have been developed (Ronchese et al. J Exp Med (1994) 179:809; Lane et al. J Exp Med. (1994) March 1; 179(3):819; Sutherland et al. Transplantation. 2000 69(9): 1806-12). In addition, PCT Publication No. WO 01/30966 to Alexion Pharmaceuticals, Inc. and PCT Publication No. WO 07/035,213 to Revivicor discloses transgenic pigs expressing only the CTLA4-Ig transgene. See also Phelps et al., Xenotransplantation, 16(6):477-485. 2009. Pigs expressing CTLA4-Ig in brain tissue were produced, but high plasma expression was shown to cause negative effects (Martin, et al. (2005) Transg. Rsch. 14:373-84). There remains doubt as to whether long term expression of immunosuppressive transgenes in ungulates raises safety concerns either for the ungulate or for the recipient of any tissues from such an animal.

In addition to the cellular and humoral immune responses, a significant challenge associated with islet transplantation is the significant early loss of islet mass immediately after infusion of the transplanted islets and contact with recipient blood, a phenomenon known as the immediate blood-mediated inflammatory response (IBMIR) (Bennet et al., Ups J Med Sci 2000, 105:125-133). The addition of an anti-coagulant transgene has been suggested to prevent coagulation responses to xenografts (reviewed by Cowan, Xenotransplantation, 2007; 14:7-12). However, these reports have focused on the reduction of coagulation associated with organ transplantation. In addition, production of anticoagulant-expressing animals suitable for xenotransplantation has proven difficult due to bleeding phenotypes seen even in small mammals such as mice (see Dwyer et al. (2004) J Clin Invest 113: 1440-46). Furthermore, there is doubt as to whether anticoagulation is useful for preventing IBMIR. It has been found that, in xenotransplant models, the use of complement depletion or anticoagulation was insufficient to prevent IBMIR (Rood et al. 2007 Transplantation 83:202-210). Cabric, et al. (2006) Cell Transpl 15:759-67 and (2007) Diabetes 56:2008-15) suggest that gene therapy approaches are not appropriate for avoiding IBMIR in pancreatic islets because they introduce new DNA into islets and are associated with a risk of inducing inflammatory or even adaptive immune responses, and transduced islets showed an impaired glucose-stimulated insulin release. They instead suggest pretreatment of islet cells with agents such as heparin.

Although xenotransplantation of islets, particularly from porcine donors, is an appealing alternative to the use of allografts because of the limited supply and quality of human pancreatic islets, major obstacles remain. Both immediate and delayed immune responses and islet destruction require potentially toxic cocktails of immunosuppressant therapies. The production of genetically modified animals to address certain immune responses has been suggested, however this production has met with limited success because of toxicity associated with expression of immunosuppressant in situ. There remains a need for improved animals and tissues suitable for xenotransplantation therapies. In particular, there remains a need for improved animals and tissues to produce insulin producing xenografts that will reduce diabetes in a patient without requiring significant or long term immunosuppressive therapies.

SUMMARY OF THE INVENTION

The present invention provides genetically modified donor animals, tissues and cells that are particularly useful for xenotransplantation therapies. More specifically, the genetically modified donor animals serve as a source of tissues and cells that overcome significant humoral (HAR and AHXR/DXR) and cellular immune responses (ACXR) as well as limit the immediate blood-mediated inflammatory reaction (IBMIR), making them particular useful for xenotransplantation therapy for diabetes, and in particular type I diabetes, using a clinically relevant immunosuppressant regimen, and with a reduced need for long term immunosuppressant or anti-coagulant therapy.

The viable, genetically modified porcine animals of the present invention are characterized by globally reduced immune reactivity (i.e., due to the lack of expression of functional alpha 1,3 galactosyl transferase ($\alpha$GT)) as well as the expression of transgenes critical to overcome transplant rejection, selected from the group including anti-coagulants, immunomodulators and cytoprotectants. Prior to the present invention, it was unknown whether these types of transgenes, which can cause the animal to be immuno-compromised and hemophilic, could be expressed in a single animal that would be able to be a suitable transplantation donor because it was expected that the animals' viability would be severely curtailed. The present inventors have found that such donor animals, tissues and cells can be obtained, in particular when globally reduce immune reactivity due to lack of expression of functional alpha 1,3 galactosyltransferase (GTKO) is combined with tissue-specific expression of certain transgenes.

In one embodiment of the present invention, porcine animals, tissues and cells are provided that lack any expression of functional alpha 1,3 galactosyltransferase (GTKO) and that specifically express at least one transgene in pancreatic tissue.

In a particular embodiment, the transgene specifically expressed in pancreatic tissue is at least one anti-coagulant. In another particular embodiment, the transgene specifically expressed in pancreatic tissue is at least one immunomodulator. In specific embodiment, the transgene specifically expressed in pancreatic tissue is at least one immunosuppressant. In a further particular embodiment, the transgene specifically expressed in pancreatic tissue is at least one cytoprotective transgene.

In another embodiment of the present invention, GTKO animals, tissues and cells are provided that specifically express multiple transgenes in pancreatic tissue. In a particular embodiment, the multiple transgenes are selected from the group that includes anticoagulants, immunomodulators and cytoprotective transgenes.

In a particular embodiment, GTKO animals, tissues and cells are provided that specifically express at least two transgenes in pancreatic tissue. In a specific embodiment, the at least two transgenes are both anti-coagulants.

In a particular embodiment, GTKO animals, tissues and cells are provided specifically express at least three transgenes in pancreatic tissue. In a specific embodiment, the at least three transgenes include two anti-coagulant transgenes and an immunosuppressant transgene.

In a further specific embodiment, GTKO animals, tissues and cells are provided that lack any expression of functional alpha 1,3 galactosyltransferase (GTKO) and that specifically express TFPI, CD39 and CTLA4 in pancreatic tissue.

In a further embodiment of the present invention, porcine animals, tissues and cells are provided that lack any expression of functional alpha 1,3 galactosyltransferase (GTKO) and that express at least one first transgene and at least one second transgene, wherein the second transgene is specifically expressed in pancreatic tissue.

In one embodiment, the at least one first transgene is an immunomodulator. In a particular embodiment, the at least one first transgene is a compliment inhibitor.

In another embodiment, the at least one first transgene is a compliment inhibitor and the at least one second transgene specifically expressed in pancreatic tissue is selected from the group that includes (i) an anti-coagulant; (ii) an immunosuppressive; and (iii) a cytoprotectant.

In one embodiment, porcine animals, tissues and cells are provided that lack any expression of functional alpha 1,3 galactosyltransferase (GTKO) and expresses at least one compliment inhibitor and at least one additional transgene selected from the group consisting of anti-coagulants, immunosuppressants and cytoprotectants.

In a specific embodiment, porcine animals, tissues and cells are provide that lack any expression of functional alpha 1,3 galactosyltransferase (GTKO) and expresses at least one compliment inhibitor and at least one anti-coagulant. In a particular embodiment, the compliment inhibitor is CD46 and the at least one anti-coagulant is selected from the group that consists of TFPI, CD39, hirudin, thrombomodulin and EPCR. In a further particular embodiment, the at least one compliment inhibitor is CD46 and the at least one additional transgene is an immunosuppressant, e.g., CTLA4.

In a specific embodiment, procine animals, tissues and cells are provided that lack any expression of functional alpha 1,3 galactosyltransferase (GTKO) and further express at least one compliment inhibitor, at least one anticoagulant and at least one immunosuppressant. Optionally, the porcine animals, tissues and cells also express at least one cytoprotective transgene.

In one embodiment, the transgene is specifically expressed in pancreatic cells. In a particular embodiment, the transgene is specifically expressed in pancreatic islet cells. In a specific embodiment, the transgene is specifically expressed in a beta cell. The expression can be at any level, but in a specific embodiment, the expression is at a high level. In a particular embodiment, the cells are encapsulated.

An anticoagulant according to the present invention can be selected from the group that includes tissue factor pathway inhibitor (TFPI), hirudin, thrombomodulin, endothelial protein C receptor (EPCR), and CD39. In a particular embodiment, the anticoagulant is TFPI. In another embodiment, the anticoagulant is CD39.

An immunomodulator according to the present invention can be a complement inhibitor or an immunosuppressant. In specific embodiments, the immunomodulator is a complement inhibitor. The complement inhibitor can be CD46 (or MCP), CD55, CD59 or CR1. In another specific embodiment, the immunomodulator is an immunosuppressant. The immunosuppressor can be CTLA4-Ig. Other immunomodulators can be class II transactivator (CIITA) and mutants thereof, PDL1, PDL2, or tumor necrosis factor-α-related apoptosis-inducing ligand (TRAIL), Fas ligand (FasL, CD95L) CD47, known as integrin-associated protein (CD47), HLA-E, HLA-DP, HLA-DQ, HLA-DR.

The cytoprotective transgene according to the present invention can be an anti-apoptotic, an anti-oxidant or an anti-inflammatory transgene. In certain embodiments, the cytoprotective transgene is selected from the group that includes A20, HO-1, FAT-1, and soluble TNF-alpha receptor (sTNFR1).

In a specific embodiment, the present invention provides porcine animals, tissues and cells are provided with at least the following genetic modifications: lack of expression of GT, expression of CD46 and pancreatic-specific expression of TFPI. In a particular embodiment, CD46 is ubiquitously expressed.

In another specific embodiment, the present invention provides porcine animals, tissues and cells are provided with at least the following genetic modifications: lack of expression of GT, expression of CD46, pancreatic-specific expression of TFPI, and pancreatic-specific expression of CD39. In a particular embodiment, CD46 is ubiquitously expressed.

In another specific embodiment, the present invention provides porcine animals, tissues and cells are provided with at least the following genetic modifications: lack of expression of GT, expression of CD46, pancreatic-specific expression of TFPI, and pancreatic-specific expression of CTLA4-Ig. In a particular embodiment, CD46 is ubiquitously expressed.

In a further specific embodiment, the present invention provides porcine animals, tissues and cells are provided with at least the following genetic modifications: lack of expression of GT, expression of CD46, pancreatic-specific expression of TFPI, pancreatic-specific expression of CD39, and pancreatic-specific expression of CTLA4-Ig. In a particular embodiment, CD46 is ubiquitously expressed.

In another specific embodiment, the present invention provides porcine animals, tissues and cells are provided with at least the following genetic modifications: lack of expression of GT, expression of CD46, expression of an cytoprotective transgene, pancreatic-specific expression of TFPI, pancreatic-specific expression of CD39, and pancreatic-specific expression of CTLA4-Ig. In a particular embodiment, CD46 is ubiquitously expressed.

In another specific embodiment, the present invention provides porcine animals, tissues and cells are provided with at least the following genetic modifications: lack of expression of GT, expression of CD46, expression of an cytoprotective transgene, pancreatic-specific expression of TFPI and pancreatic-specific expression of CD39. In a particular embodiment, CD46 is ubiquitously expressed.

In one embodiment, a method is provided for treatment or prophylaxis of diabetes including administering the tissues or cells of the present invention to a host in need thereof. In a particular embodiment, the host is a diabetic host.

In one embodiment, the diabetic host is a diabetic primate. In a particular embodiment, the host is a diabetic human. In a specific embodiment, the host is a human suffering from Type 1 diabetes (T1B).

In one embodiment, the tissue is porcine pancreas tissue. In another embodiment, the cells are pancreas-derived cells, whole islets, or isolated pancreatic islet cells. In a particular embodiment, the cells are islets. In another particular embodiment, the pancreatic cells are beta cells. In one embodiment, the pancreatic cells are adult cells. In another embodiment, the pancreatic cells are fetal or neonatal cells.

In one embodiment, a method is provided to treating or preventing diabetes that includes administering islet cells isolated from porcine animals of the present invention.

In an alternative embodiment, a method is provided to reduce the amount of insulin required by a diabetic host by administering the tissues or cells of the present invention to a diabetic host. In a particular embodiment, the host requires reduced or no exogenous insulin after treatment. In one embodiment, the host requires from about 5% to about 25% less insulin after treatment. In another embodiment, the host requires from about 25% to about 50% less insulin after treatment. In yet another embodiment, the host requires from about 50% to about 75% less insulin after treatment. In a still further embodiment, the host requires from about 75% to about 100% less insulin after treatment.

In a particular embodiment, after treatment, the host requires less than 4 units of insulin/day, less than 3 units of insulin/day, less than 2, less than 2 units of insulin/day, or less than 1 unit of insulin/day. In one embodiment, after treatment, the host requires no exogenous insulin.

In other embodiments, tissues or cells provided herein can be used in re-transplant procedures, such procedures may be necessary, for example, in certain embodiments, to maintain sufficient levels of islets to control glycemia long-term.

In one embodiment of the present invention, a method is provided for treatment or prophylaxis of diabetes including administering the tissues or cells of the present invention to a host suffering from diabetes, wherein the host requires no or reduced immunosuppressive therapy after the treatment.

In one embodiment, the dose of immunosuppressive drug(s)/agent(s) is/are reduced compared to other methods. In a specific embodiment, the dosage of one or more of daclizumab, tacrolimus, and/or sirolimus is reduced compared to dosages used in other methods of transplantation.

In another embodiment, the number of types of immunosuppressive drug(s)/agent(s) is/are reduced compared to other methods.

In one embodiment, the duration of immunosuppression is shortened compared to other methods.

In another embodiment, lower or no maintenance immunosuppression is used compared to other methods.

In one embodiment, a method is provided for treatment or prophylaxis of diabetes including administering the tissues or cells of the present invention to a host suffering from diabetes, wherein the IEQ/kg (pancreatic islet equivalents per kg) requirements are reduced compared to other methods. In another embodiment, the IEQ/kg is below 100,000. In a further embodiment, the IEQ/kg is below 50,000. In one embodiment, the IEQ/kg is below 25,000. In another embodiment, the IEQ/kg is below 10,000.

In a further embodiment, a method is provided for treatment or prophylaxis of diabetes including administering the pancreatic cells or islets of the present invention to a host suffering from diabetes, wherein the tissues or cells are administered by intraportal infusion. In a particular embodiment, islets are administered by intraportal infusion. In one embodiment, the islets are administered into the intraperitoneal space, renal subcapsule, renal capsule, omentum, or via pancreatic bed infusion.

In another embodiment, a method is provided for treatment or prophylaxis of diabetes including administering the pancreatic cells or islets of the present invention to a host suffering from diabetes, wherein the tissues or cells are encapsulated. In one embodiment, the cells are microencapsulated. In an alternate embodiment, the cells are macroencapsulated. In another embodiment, the cells are not encapsulated. In a particular embodiment, the cells are provided in the form of a thin planar sheet containing purified alginate and cells. In a specific embodiment, the islets are microencapsulated, macroencapsulated or provided as a thin planar sheet of containing purified alginate and islets.

In further embodiments, a method is provided for treatment or prophylaxis of diabetes including administering the tissues or cells of the present invention to a diabetic host, wherein after the transplant the host has some or all functional transplanted cells. In one embodiment, the host has more functional transplanted islets compared to the number of functional transplanted islets present after performing other methods. In one embodiment, islet functionality is defined as basal or stimulated porcine C-peptide greater than 0.3 ng/dl. In one embodiment, islet functionality is defined as detectable porcine C-peptide in combination with a greater than 50% reduction of exogenous insulin needs, wherein the C-peptide is produced from the transplanted material. In a particular embodiment, 10, 20, 30, 40, 50, 60, 70, 80, 90, 100% of the transplanted islets are functional.

In other embodiments, a method is provided for treatment or prophylaxis of diabetes including administering the tissues or cells of the present invention to a diabetic, wherein after the transplant the host can maintain normoglycemia. In one embodiment, normoglycemia is maintained for at least 3 months. In another embodiment, normoglycemia is maintained for at least 6 or at least 12 months.

In other embodiments, a method is provided for treatment or prophylaxis of diabetes including administering the tissues or cells of the present invention to a diabetic, wherein after the transplant the fasting and non-fasting blood glucose levels (FBG and NFBG, respectively) of the host are maintained at normal levels. In one embodiment, the normal levels should be maintained for at least 3 months. In another embodiment, the normal levels should be maintained for at least 6 months. In another embodiment, the normal levels should be maintained for at least 12 months. In a particular embodiment, FBG can be maintained from about 70 to about 100 mg/dL (3.9 to 5.5 mmol/L). In another embodiment, the FBG can be maintain from about 70 to about 130 mg/DL. In another particular embodiment, NFBG can be maintained at less than about 200 mg/dL.

In one embodiment, after treatment, the host has a glycated hemoglobin level of less than about 8.0%. In another embodiment, after treatment, the host has a glycated hemoglobin level of less than about 6.5%.

In one embodiment, a method is provided for treatment or prophylaxis of diabetes including administering the tissues or cells of the present invention to a diabetic host, wherein the host successfully passes an intravenous glucose tolerance test post-transplant. In one embodiment, the test can be performed at 1, 3, 6 and/or 12 months post transplant. In another embodiment, the results of the test are successful if significant response to glucose in the form of porcine C-peptide is demonstrated in the absence of a significant response of non-human primate C-peptide.

In another embodiment, a method is provided for treatment or prophylaxis of diabetes including administering the tissues or cells of the present invention to a diabetic host suffering from diabetes, wherein the host successfully passes an arginine stimulation test post-transplant. In one embodiment, the test can be performed at 1, 3, 6 and/or 12 months post transplant. In another embodiment, the results of the test are successful if significant response to glucose in the form of porcine C-peptide is demonstrated in the absence of a significant response of non-human primate C-peptide.

In one embodiment, a method is provided for treatment or prophylaxis of diabetes including administering the tissues or cells of the present invention to a diabetic host, wherein after the transplant donor C-peptide levels are detectable. In another embodiment, porcine C-peptide levels are about between about 0.3 and about 0.96. In one specific embodiment, porcine C-peptide levels are about between about 0.21 and about 0.63 (ng/ml).

In another embodiment, a method is provided for treatment or prophylaxis of diabetes including administering the tissues or cells of the present invention to a diabetic host, wherein post-transplant histological analysis of the host is conducted. In one embodiment, the histological analysis of the native pancreas after necropsy indicates reduced, in one non-limiting example, none, insulin-positive beta cells. In a further embodiment, the histological examination of the liver or other site of islet transplant indicates multiple viable insulin-positive cells.

In a further embodiment, a method is provided for treatment or prophylaxis of diabetes including administering the tissues or cells of the present invention to a diabetic host, wherein post-transplant there are not numerous, or serious life-threatening, complications associated with one or more of the transplant procedure, the immunosuppressive regime, tolerance inducing regime or the encapsulation of the islets.

Other embodiments of the present invention will be apparent to one of ordinary skill in light of the following description of the invention, the claims and what is known in the art.

DESCRIPTION OF FIGURES

The patent or application file contains at least one drawing executed in color. Copies of this patent or patent application publication with color drawing(s) will be provided by the Office upon request and payment of the necessary fee.

DETAILED DESCRIPTION OF THE INVENTION

Figure 1:
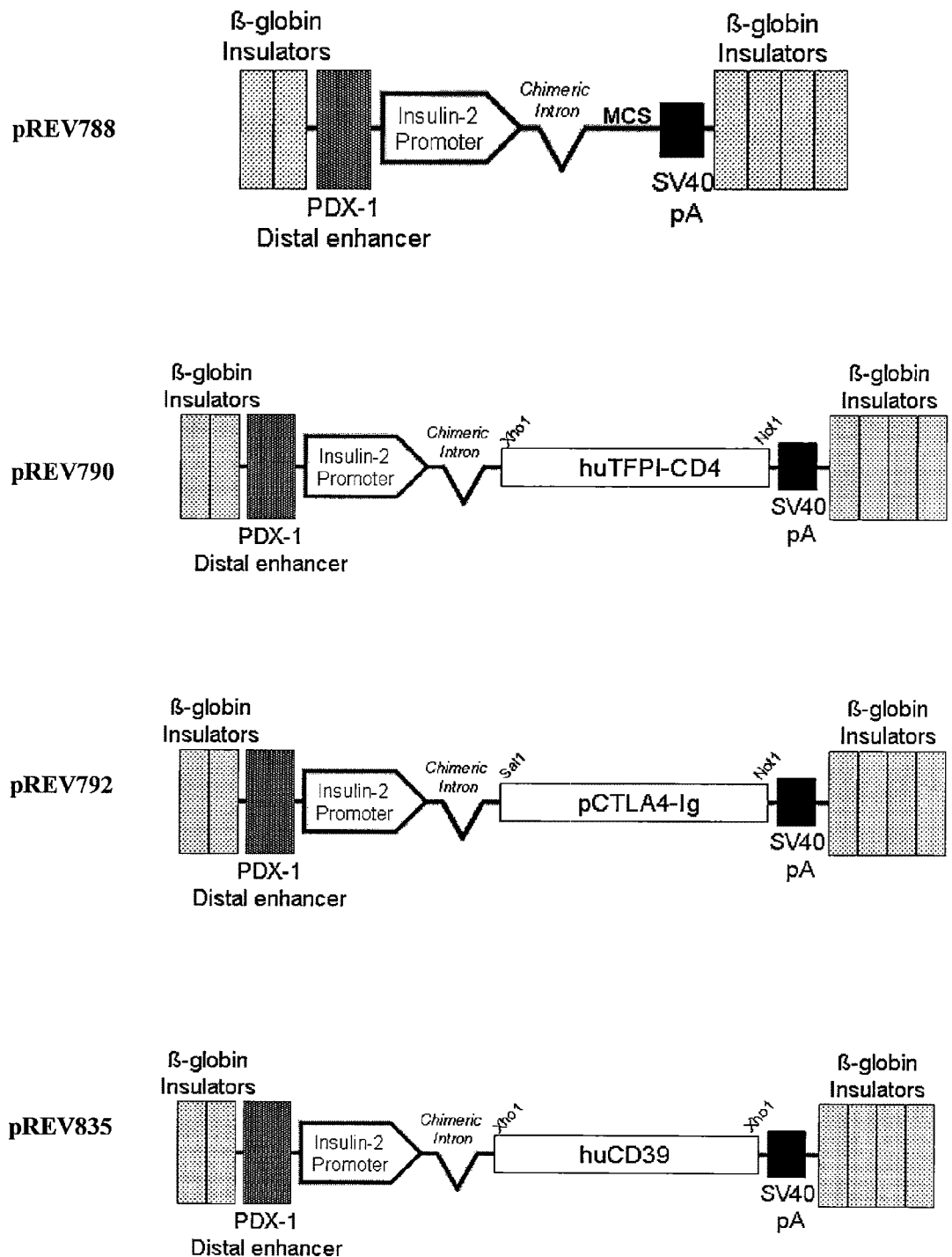
FIG. 1 is a representative figure of the vectors used in the invention. "pREV788" is the base vector; pREV790 is the base vector with a TFPI-CD4 transgene; pREV792 is the base vector with a pCTLA4-Ig transgene; and pREV835 is the base vector with a CD39 transgene.

There is increasing evidence that donor vascular endothelial cells, present in the islet grafts, play an important role in the formation of new blood vessels involved in revascularization of the islet tissue in the recipients post-transplant (Linn et al., FASEB, (2003)17:881-883; Brissova et al., Diabetes (2004) 53:1318-1325; Johansson U, et al., Am J. Transplant. (2005) 5:2632-2639; Nyqvist, et al., Diabetes, (2005) 54:2287-2293). Some new vessels are lined with donor endothelial cells, while other vessels may be reconstituted as chimeras of donor and recipient cells (Brissova et al., Diabetes (2004) 53:1318-1325). Without the presence of viable donor endothelial cells, revascularization is delayed and incomplete, resulting in ischemic injury and death of many of the islets. Therefore, the present invention comprises pigs with the GTKO genetic background plus other transgenes towards improved outcomes in islet transplantation. Islets from GTKO pigs expressing other transgenes specifically in pancreas, will provide significant protection of the donor endothelial cells, and therefore of the islets.

A "transgene" is a gene or genetic material that has been transferred from one organism to another. Typically, the term describes a segment of DNA containing a gene sequence that has been isolated from one organism and is introduced into a different organism. This non-native segment of DNA may retain the ability to produce RNA or protein in the transgenic organism, or it may alter the normal function of the transgenic organism's genetic code. In general, the DNA is incorporated into the organisms germ line. For example, in higher vertebrates this can be accomplished by injecting the foreign DNA into the nucleus of a fertilized ovum. When inserted into a cell, a transgene can be either a cDNA (complementary DNA) segment, which is a copy of mRNA (messenger RNA), or the gene itself residing in its original region of genomic DNA. The transgene can be a genome sequence, in particular when introduced as large clones in BACs (bacterial artificial chromosomes) or cosmid. Transgene "expression" in the context of the present specification, unless otherwise specified, means that a peptide sequence from a non-native nucleic acid is expressed in at least one cell in a host. The peptide can be expressed from a transgene that is incorporated in the host genome.

A "donor" is meant to include any non-human organism that may serve as a source of donor tissue or cells for xenotransplantation including, but not limited to, mammals, birds, chickens, reptiles, fish, and insects. The donor may be in any stage of development, including, but not limited to fetal, neonatal, young and adult. An "animal" is typically a mammal. A "mammal" is meant to include any non-human mammal, including but not limited to pigs, sheep, goats, cattle (bovine), deer, mules, horses, monkeys, dogs, cats, rats, and mice. In one embodiment of the invention, genetically altered pigs and methods of production thereof are provided. The animals of the invention are "genetically modified" or "transgenic," which means that they have a transgene, or other foreign DNA, added or incorporated, or an endogenous gene modified, including, targeted, recombined, interrupted, deleted, disrupted, replaced, suppressed, enhanced, or otherwise altered, to mediate a genotypic or phenotypic effect in at least one cell of the animal, and typically into at least one germ line cell of the animal. In some embodiments, animals may have the transgene integrated on one allele of its genome (heterozygous transgenic). In other embodiments, animals may have the transgene on two alleles (homozygous transgenic).

The term "ungulate" refers to hoofed mammals. Artiodactyls are even-toed (cloven-hooved) ungulates, including antelopes, camels, cows, deer, goats, pigs, and sheep. Perissodactyls are odd toes ungulates, which include horses, zebras, rhinoceroses, and tapirs. The term ungulate as used herein refers to an adult, embryonic or fetal ungulate animal.

The terms "porcine", "porcine animal", "pig" and "swine" are generic terms referring to the same type of animal without regard to gender, size, or breed.

The "cells" of the invention are derived from an animal. Although the cells can be derived from a mature animal, in some embodiments the cell is derived from a fetal or neonatal tissue. In particular embodiments of the invention, the cells, and especially the pancreatic islet cells, are derived from a transgenic porcine animal and in particular, a transgenic porcine that has grown to a sufficient size to be useful as an adult islet donor. In certain embodiments, the animals survive past weaning age. In specific embodiments, the animals are at least six months old. In certain embodiments, the animal survives to reach breeding age. In certain embodiments, the animal is a porcine animal of at least 300 pounds. In specific embodiments, the animal is a porcine sow and has given birth at least one time.

"High" levels of expression are considered sufficient to provide a phenotype (detectable expression or therapeutic benefit). Typically a 'high' level of expression is sufficient to be capable of reducing graft rejection including hyperacute rejection (HAR), acute humoral xenograft rejection (AHXR), T cell-mediated cellular rejection and immediate blood-mediated inflammatory response (IBMIR). It was previously unknown whether anticoagulant and immunosuppressive transgenes could be expressed in pancreatic islet cells at levels capable of reducing these types of rejection.

Transgenic Animals

In one embodiment, porcine animals, tissues and cells are provided that have at least four genetic modifications. Such genetic modifications can include, without limitation, additions and/or deletions of genes, including knock-outs and knock-ins, as well as re-arrangements. In a particular embodiment, porcine animals, tissues and cells are provided that have at least four genetic modifications, wherein at least one, at least two, at least three or four of the genetic modifications are transgenes and at least one, at least two, at least three or four of the transgenes are ubiquitously expressed. In a particular embodiment, porcine animals, tissues and cells are provided that have at least four genetic modifications, wherein at least one genetic modification is a knock-out.

In a particular embodiment, porcine animals, tissues and cells are provided that have at least one gene knocked out and express at least three transgenes. In a specific embodiment, the at least one gene is knocked out by homologous recombination.

In one embodiment, porcine animals, tissues and cells are provided that have at least five genetic modifications. Such genetic modifications can include, for example, additions and/or deletions of other genes, including knock-outs and knock-ins, as well as rearrangements. In a particular embodiment, porcine animals, tissues and cells are provided that have at least five genetic modifications, wherein at least one, at least two, at least three, at least four or five of the genetic modifications are transgenes and at least one, at least two, at least three, at least four or five of the transgenes are ubiquitously expressed. In a particular embodiment, porcine animals, tissues and cells are provided that have at least five genetic modifications, wherein at least one genetic modification is a knock-out.

In a particular embodiment, porcine animals, tissues and cells are provided that have at least one gene knocked out and express at least four transgenes. In a specific embodiment, the at least one gene is knocked out by homologous recombination.

In one embodiment, porcine animals, tissues and cells are provided that lack any expression of functional alpha 1,3 galactosyltransferase (GTKO) and express at least one transgene in pancreatic tissue. In other embodiments, GTKO animals, tissues and cells are provided which express multiple transgenes in pancreatic tissue. In particular subembodiments, the animals, tissues and cells express at least one immunomodulator. In certain embodiments, the animals, tissues and cells express more than one immunomodulator. In particular embodiments, GTKO animals, tissues and cells are provided that express at least one immunomodulator and at least one anti-coagulant transgene. In one embodiment, the immunomodulator is an immunosuppressant. In an alternate embodiment, the immunomodulator is a complement inhibitor. In a particular embodiment, expression of the immunomodulator is specific to the pancreas. In a further particular embodiment, expression of the immunosuppressant is specific to the pancreas. In a still further specific embodiment, expression of the compliment inhibitor is specific to the pancreas. In other subembodiments, the animals, tissues and cells express at least one anticoagulant. In certain embodiments, the animals, tissues and cells express more than one anticoagulant. In a particular embodiment, the expression of the anticoagulant is specific to the pancreas. In one subembodiment, the animals, tissues and cells express at least one cytoprotective transgene. In another embodiment, the animals, tissues and cells express more than one cytoprotective transgene. In one embodiment, the transgene is specifically expressed in islets, in a particular embodiment, specific expression in beta cells is provided.

In one embodiment, the present invention includes GTKO animals, tissue and cells that lack any expression of functional alpha 1,3 galactosyltransferase (GTKO) and expresses at least one compliment inhibitor and at least one additional transgene selected from the group consisting of anti-coagulants, immunosuppressants and cytoprotectants. In a particular embodiment, the expression of the at least one additional transgene is specific to the pancreas.

In a specific embodiment, GTKO animals, tissues and cells are provided that express at least one compliment inhibitor (e.g., CD46) and at least one anti-coagulant (e.g., TFPI).

In another specific embodiment, GTKO animals, tissue and cells are provided that express at least one compliment inhibitor (e.g., CD46) and at least two anti-coagulants (e.g., TFIP and CD39).

In another specific embodiment, GTKO animals, tissues and cells are provided that express at least one compliment inhibitor (e.g., CD46) and at least one immunosuppressant (e.g., CTLA4).

In a still further specific embodiment, GTKO animals, tissues and cells are provided that express at least one compliment inhibitor (e.g., CD46) and a cytoprotective trans gene (e.g., A20).

In certain embodiments, GTKO animals, tissues and cells are provided that express at least one immunosuppressant, at least one complement inhibitor and at least one anticoagulant transgene. In an further particular embodiment, GTKO animals, tissues and cells are provided that express at least one immunosuppressant, at least one complement inhibitor and at least two anticoagulant transgenes. In a specific embodiment, GTKO animals, tissues and cells are provided that express at least one immunosuppressant, at least one complement inhibitor and at least one anticoagulant transgenes, wherein expression of the at least one immunosuppressant and the at least one anticoagulant transgenes is specific to the pancreas. In yet another specific embodiment, GTKO animals, tissues and cells are provided that express at least one immunosuppressant, at least one complement inhibitor and at least two anticoagulant transgenes, wherein expression of the at least one immunosuppressant and the at least two anticoagulant transgenes is specific to the pancreas. In one embodiment, the transgene is specifically expressed in islets, in a particular embodiment, specific expression in beta cells is provided.

In one embodiment, GTKO animals, tissues and cells are provided that express at least one immunomodulator, at least one anticoagulant and at least one cytoprotective transgene. In a further embodiment, GTKO animals, tissues and cells are provided that express at least one immunosuppressant, at least one complement inhibitor, at least one anticoagulant transgene and at least one cytoprotective transgene. In a further particular embodiment, GTKO animals, tissues and cells are provided that express at least one immunosuppressant, at least one complement inhibitor, at least two anticoagulant transgenes and at least one anti-cytoprotective transgene. In a particular embodiment, GTKO animals, tissues and cells are provided that express at least one immunosuppressant, at least one complement inhibitor, at least one anticoagulant transgene and at least one cytoprotective transgene, wherein the expression of the at least one immunosuppressant and the at least one anticoagulant transgenes is specific to the pancreas. In a particular embodiment, GTKO animals, tissues and cells are provided that express at least one immunosuppressant, at least one complement inhibitor, at least two anticoagulant transgenes and at least one cytoprotective transgene, wherein the expression of the at least one immunosuppressant and the at least two anticoagulant transgenes is specific to the pancreas. In a specific embodiment, the expression of the anti-apoptotic transgene is specific to the pancreas. In one embodiment, the transgene is specifically expressed in islets, in a particular embodiment, specific expression in beta cells is provided.

In one embodiment, the transgenic porcine animals described herein are viable. In another embodiment, the animals described herein are fertile. In further embodiments, the animals described herein can stably transmit some of its genetic modifications to its offspring. In still further embodiments, the animals described herein can stably transmit all of its genetic modifications to its offspring. In certain embodiments, the animals can stably transmit all of its genetic modifications to its offspring when the animals are bred naturally. In other embodiments, the multiple transgenes exhibit co-segregation to offspring. In particular embodiments, the cells are derived from a pancreas of a viable animal. In particular embodiments, the cells are pancreatic islets. In more particular embodiments, the cells are pancreatic beta cells. In certain embodiments, the cells are insulin-producing. In some further embodiments, the cells include islet cell clusters. In still further embodiments, the cells are islet-like cells.

In a particular embodiment, porcine animal, tissues and cells are provided with at least the following genetic modifications: lack of expression of GT, expression of a complement inhibitor, pancreatic-specific expression of an anticoagulant transgene, and pancreatic-specific expression of an immunosuppressant transgene. In a particular embodiment, porcine animal, tissues and cells are provided with at least the following genetic modifications: lack of expression of GT, expression of a complement inhibitor, pancreatic-specific expression of two anticoagulant transgenes, and pancreatic-specific expression of an immunosuppressant transgene. In one embodiment, the transgene is specifically expressed in an islet cell, in a particular embodiment, specific expression in beta cells is provided.

In another embodiment, porcine animal, tissues and cells are provided with at least the following genetic modifications: lack of expression of GT, expression of a complement inhibitor, expression of a cytoprotective transgene, pancreatic-specific expression of an anticoagulant transgene, and pancreatic-specific expression of an immunosuppressant transgene. In a particular embodiment, porcine animal, tissues and cells are provided with at least the following genetic modifications: lack of expression of GT, expression of a complement inhibitor, expression of a cytoprotective transgene, pancreatic-specific expression of two anticoagulant transgenes, and pancreatic-specific expression of an immunosuppressant transgene. In a specific embodiment, the expression of the cytoprotective transgene is also pancreas-specific. In one embodiment, the transgene is specifically expressed in an islet, in a particular embodiment, specific expression in beta cells is provided.

An immunomodulator can be a complement inhibitor or an immunosuppressant. In specific embodiments, the immunomodulator is a complement inhibitor. The complement inhibitor can be CD46 (or MCP). In other embodiments, the complement inhibitor is CD55, CD59 or CR1. In certain embodiments, the transgene is expressed from a ubiquitous promoter. In certain other embodiments, the transgene is expressed from a promoter active primarily in pancreatic cells. The expression can be at any level, but in specific embodiments, the expression is at high levels.

An immunomodulator can also be an immunosuppressant. The immunosuppressant can be capable of down-regulating a T-cell mediated response. In particular, the immunosuppressant can be CTLA4-Ig or mutants thereof. In other embodiments, the immunosuppressant transgene is a ligand that interferes with CD28 activity, such as a B7 receptor peptide or mutant thereof. In certain embodiments, the transgene is expressed from a promoter active primarily in pancreatic cells. The expression can be at any level, but in specific embodiments, the expression is at high levels.

In other embodiments, the immunomodulator can be selected from the group that includes class II transactivators (CIITA) and mutants thereof, PDL1, PDL2, tumor necrosis factor-α-related apoptosis-inducing ligand (TRAIL), Fas ligand (FasL, CD95L) integrin-associated protein (CD47), HLA-E, HLA-DP, HLA-DQ, or HLA-DR. In certain other embodiments, the transgene is expressed from a promoter active primarily in pancreatic cells. The expression can be at any level, but in specific embodiments, the expression is at high levels.

In one embodiments, the anticoagulant is selected from the group that includes tissue factor pathway inhibitor (TFPI), hirudin, thrombomodulin, endothelial protein C receptor (EPCR), and CD39. In a particular embodiment, the anticoagulant is TFPI. In another particular embodiment, the anticoagulant is CD39. In certain other embodiments, the transgene is expressed from a promoter active primarily in pancreatic cells. The expression can be at any level, but in specific embodiments, the expression is at high levels.

The cytoprotective transgene can be an anti-apoptotic, anti-oxidant or anti-inflammatory transgene. In certain embodiments, the cytoprotective transgene is selected from the group that includes A20, HO-1, FAT-1, and soluble TNF-alpha receptor (sTNFR1). In certain other embodiments, the transgene is expressed from a promoter active primarily in pancreatic cells. The expression can be at any level, but in specific embodiments, the expression is at high levels.

In certain embodiments, the one or more immunosuppressant or anticoagulant transgenes is expressed in pancreatic tissues of GTKO porcine animals which express high levels of CD46. In particular embodiments, porcine animals, tissues and cells are provided derived from GTKO animals that express high levels of CD46 and express TFPI and CTLA4-Ig in pancreatic tissues, and in particular in pancreatic islet cells. In a separate embodiment, porcine animals, tissues and cells derived from GTKO animals are provided that express high levels of CD46 and express CD39 and CTLA4-Ig in pancreatic tissues and in particular in pancreatic islet cells.

In some embodiments, the immunomodulator has the sequence of a human protein. In other embodiments, the immunomodulator has the sequence of a porcine protein. In some embodiments, the anticoagulant has the sequence of a human protein. In other embodiments, the anticoagulant has the sequence of a porcine protein. In some embodiments, the cytoprotective transgene has the sequence of a porcine protein. In another embodiment, the cytoprotective transgene has the sequence of a human protein. In particular embodiments, the porcine animal, tissue or cell expresses a human CD46 transgene. In particular embodiments, the porcine animal, tissue or cell expresses a human CTLA4-Ig transgene. In certain embodiments, the porcine animal, tissue or cell expresses a human TFPI. In certain embodiments, the porcine animal, tissue or cell expresses a human CD39. In particular embodiments, the porcine animal, tissue or cell expresses a porcine CD46 transgene. In particular embodiments, the porcine animal, tissue or cell expresses a porcine CTLA4 transgene. In certain embodiments, the porcine animal, tissue or cell expresses a porcine TFPI. In certain embodiments, the porcine animal, tissue or cell expresses a porcine CD39.

In a particular embodiment, porcine animal, tissues and cells are provided with at least the following genetic modifications: lack of expression of GT, expression of CD46, pancreatic-specific expression of TFPI, and pancreatic-specific expression of CTLA4-Ig. In another particular embodiment, porcine animal, tissues and cells are provided with at least the following genetic modifications: lack of expression of GT, expression of CD46, pancreatic-specific expression of TFPI, pancreatic-specific expression of CD39, and pancreatic-specific expression of CTLA4-Ig. In one embodiment, the transgene is specifically expressed in an islet cell, in a particular embodiment, specific expression in beta cells is provided. In a particular embodiment, the CD46 can be a human CD46. In another particular embodiment, the human CD46 can be expressed at high levels.

In another particular embodiment, porcine animal, tissues and cells are provided with at least the following genetic modifications: lack of expression of GT, expression of CD46, expression of a cytoprotective transgene, pancreatic-specific expression of TFPI, and pancreatic-specific expression of CTLA4-Ig. In another particular embodiment, porcine animal, tissues and cells are provided with at least the following genetic modifications: lack of expression of GT, expression of CD46, expression of a cytoprotective transgene, pancreatic-specific expression of TFPI, pancreatic-specific expression of CD39, and pancreatic-specific expression of CTLA4-Ig.

In certain embodiments, the transgene is expressed from a promoter active primarily in pancreatic cells. In certain embodiments the promoter is a pancreas or islet specific promoter such as the insulin promoter from a vertebrate animal, including but not limited to fish or mammalian promoters such as tilapia, human, pig, rat, or mouse. In specific embodiments, the promoter is a rat-insulin promoter (RIP). In certain embodiments additional regulatory elements would be incorporated into the transgene expression system, including enhancer elements. The enhancer can be, for example, a pdx-1 enhancer or a chicken actin enhancer, or can be an insulator element for example, a chicken beta-globin insulator, for enhanced expression of the transgene (Chung J H, Bell A C, Felsenfeld G., Proc Natl Acad Sci USA. 1997 Jan. 21; 94(2):575-80).

In certain embodiments, the expression is only in pancreatic tissue and is not in other porcine tissues. In addition, expression can be present in fetal, neonatal, and mature tissues, each of which can be a source of donor islets. In particular embodiments of the invention, the cells, and especially the pancreatic islet cells, are derived from a transgenic porcine animal and in particular, a transgenic porcine that has grown to a sufficient size to be useful as an adult islet donor. In certain embodiments, the animals survive past weaning age. In specific embodiments, the animals are at least six months old. In certain embodiments, the animal survives to reach breeding age. In certain embodiments, the animal is a porcine animal of at least 300 pounds. In a particular embodiment, encapsulated islets can be transplanted.

In one embodiment, a method is provided for treatment or prophylaxis of diabetes including administering a porcine pancreas tissue, pancreas-derived cells, whole islets, or isolated pancreatic islet cell to a host suffering from diabetes (a diabetic host or diabetic patient), wherein the cell exhibits expresses at least one immunosuppressant and at least one anticoagulant transgene. In another embodiment, islet cells isolated from porcine animals provided herein are used to treat or reverse diabetes.

In one embodiment, islet cells provided herein can be used to reduce the amount of insulin required by a diabetic host. After the transplant, the patient may require 5%, 10%, 20%, 30%, 40%, 50%, 60%, 70%, 80%, 90% or 100% less insulin than that required prior to the transplant. After the transplant, the host may require about 5% to about 25% less insulin than that required prior to the transplant. After the transplant, the host may require about 25% to about 50% less insulin than that required prior to the transplant. After the transplant, the host may require about 50% to about 75% less insulin than that required prior to the transplant. After the transplant, the host may require about 75% to about 100% less insulin than that required prior to the transplant.

In a particular embodiment, after the transplant, the host may require less than 0.6, 0.5, 0.4, 0.3, 0.2, 0.1, 0.05, or 0.01 exogenous units of insulin per kilogram (kg) per day. In one embodiment, the host after the transplant requires any number less than about 0.01 to about 0.1 exogenous units of insulin per kilogram (kg) per day. In one embodiment, the patient after the transplant requires any number less than about 0.1 to about 0.25 exogenous units of insulin per kilogram (kg) per day. In one embodiment, the patient after the transplant requires any number less than about 0.25 to about 0.5 exogenous units of insulin per kilogram (kg) per day. In one embodiment, the patient after the transplant requires any number less than about 0.5 to about 0.6 exogenous units of insulin per kilogram (kg) per day.

In one particular embodiment, after the transplant, the patient requires less than 4 units of insulin/day. In one embodiment, after transplant, the patient requires less than 2 units of insulin/day. In one embodiment, after the transplant, the patient requires less than 2 units of insulin/day. In another embodiment, after transplant, the patient requires less than 1 unit of insulin per day. In one embodiment, after the transplant, the patient requires no exogenous insulin.

In other embodiments, islets provided herein can be used in re-transplant procedures, such procedures may be necessary, for example, in certain embodiments, to maintain sufficient levels of islets to control glycemia long-term.

In certain embodiments of the present invention, methods of treating or preventing diabetes in primates are provided involving administration of the tissues or cells of the present invention to primates in need thereof. In one embodiment, the primate is a non-human primate, in one non-limiting example, a monkey. In another embodiment, the primate is a human. In one embodiment, the pancreatic cells are adult cells. In another embodiment, the pancreatic cells are fetal or neonatal cells.

In additional embodiments, the animals can also contain genetic modifications to express an immunomodulator. The immunomodulator can be a complement pathway inhibitor gene and in particular embodiments is selected from CD55, CD59, CR1 and CD46 (MCP). The complement inhibitor can be human CD46 (hCD46) wherein expression is through a mini-gene construct (See Loveland et al., Xenotransplantation, 11(2):171-183. 2004). The immunomodulator can also be an immunosuppressor gene that has a T-cell modulating effect—such as CTLA4-Ig, or a dominant negative inhibitor of class II MHC(CIITA), or other genes that modulate the expression of B-cell or T cell mediated immune function. In further embodiments, such animals can be further modified to eliminate the expression of genes which affect immune function.

In additional embodiments, the animals can also contain genetic modifications to express an anticoagulant. The anticoagulant may include, but is not limited to, TFPI, hirudin, thrombomodulin, EPCR and CD39. In addition, the animals can be genetically modified to inhibit the expression of a the CMP-Neu5Ac hydroxylase gene (see, for example, U.S. Patent Publication. 2005-0223418), the iGb3 synthase gene (see, for example, U.S. Patent Publication 2005-0155095), and/or the Forssman synthase gene (see, for example, U.S. Patent Publication 2006-0068479). In addition, the animals can be genetically modified to reduce expression of a procoagulant. In particular, in one embodiment, the animals are genetically modified to reduce or eliminate expression of a procoagulant gene such as the FGL2 (fibrinogen-like protein 2) (see, for example, Marsden, et al. (2003) J din Invest. 112:58-66; Ghanekar, et al. (2004) J. Immunol. 172:5693-701; Mendicino, et al. (2005) Circulation. 112:248-56; Mu, et al. (2007) Physiol Genomics. 31(1):53-62).

In embodiments wherein a transgene is expressed, this expression may be via a ubiquitous or tissue-specific promoter and may include additional regulatory elements such as enhancers, insulators, matrix attachment regions (MAR) and the like.

To achieve these additional genetic modifications, in one embodiment, cells isolated from a genetically modified pig can be further modified to contain multiple genetic modifications. In some embodiments these cells can be used as donors to produce pigs with multiple genetic modifications via nuclear transfer. In other embodiments, genetically modified animals can be bred together to achieve multiple genetic modifications.

Transgenes to Target Acute Humoral Rejection

Xenografting is currently hindered by the severe and well-documented problems of rejection. This process can be divided into distinct stages, the first of which occurs within minutes of transplantation and is called "hyperacute rejection" (HAR). HAR is defined by the ubiquitous presence of high titers of pre-formed natural antibodies binding to the foreign tissue. The binding of these natural antibodies to target epitopes on the donor tissue endothelium is believed to be the initiating event in HAR. This binding, within minutes of perfusion of the donor tissue with the recipient blood, is followed by complement activation, platelet and fibrin deposition, and ultimately by interstitial edema and hemorrhage in the donor organ, all of which cause rejection of the tissue in the recipient (Strahan et al. (1996) Frontiers in Bioscience 1, e34-41). The primary course of HAR in humans is the natural anti-Gal antibody, which comprises approximately 1% of antibodies in humans and monkeys.

This initial hyperacute rejection is then reinforced by the delayed vascular response (also known as acute humoral xenograft rejection (AHXR), acute vascular rejection (AVR) or delayed xenograft rejection (DXR)). The lysis and death of endothelial cells during the hyperacute response is accompanied by edema and the exposure of adventitial cells, which constitutively express tissue factor (TF) on their surface. Tissue factor is thought to be pivotal in the initiation of the in vivo coagulation cascade, and its exposure to plasma triggers the clotting reactions. Thrombin and TNF-alpha become localized around the damaged tissue and this induces further synthesis and expression of TF by endothelial cells.

The environment around resting endothelial cells does not favor coagulation. Several natural coagulation inhibitors are associated with the extracellular proteoglycans of endothelial cells, such as tissue factor pathway inhibitor, antithrombin III, and thrombomodulin. The recognition of the foreign tissue by xenoreactive natural antibodies (XNAs), however, causes the loss of these molecules.

Together with the exposure and induction of tissue factor, the anticoagulant environment around endothelial cells thus becomes pro-coagulant. The vascularised regions of the xenograft thus become sites of blood clots, a characteristic of damaged tissue. Blood flow is impaired and the transplanted organ becomes ischemic. A fuller account of delayed vascular rejection can be found in Bach et al. (1996) Immunol Today. 1996 August; 17(8):379-84.

The present invention provides for animals, tissues or cells that may be used in xenotransplantation to produce low to no levels of one or more of the following: HAR, AHXR/DXR and/or ACXR. In one embodiment, the animals, tissues or cells may be used in xenotransplantation to produce low to no levels of HAR and AHXR. In another embodiment, the animals, tissues or cells may be used in xenotransplantation to produce low to no levels of HAR, AHXR and ACXR. As will be discussed in detail in the following sections, embodiments of the present invention include various combinations of complement regulator expression, immunosuppressor expression, anticoagulant expression, and/or partially or fully depleted functional αGT expression in donor tissue.

In one embodiment, islet cells isolated from the porcine animals provided herein are shown to express one or more transgenes. In further embodiments, islet cells from the porcine animals provided herein can elicit a decreased immune response by human lymphocytes (MLR assay) to said porcine cells. In another embodiment, islet cells expressing transgenes are shown to inhibit clotting and thrombosis which occurs in the xenograft environment.

Alpha 1,3 Galactosyltransferase (αGT)

As noted previously, the primary course of HAR in humans is the natural anti-galactose alpha 1,3-galactose (Gal) antibody, which comprises approximately 1% of IgG antibodies in humans and monkeys. Except for Old World monkeys, apes and humans, most mammals carry glycoproteins on their cell surfaces that contain the Gal epitope (Galili et al., J. Biol. Chem. 263: 17755-17762, 1988). Humans, apes and old world monkeys do not express Gal, but rather produce in high quantities a naturally occurring anti-Gal antibody that causes an immediate hyperacute reaction upon xenotransplantation into humans of tissues from animals carrying the Gal epitope (Sandrin et al., Proc Natl Acad Sci USA. 1993 Dec. 1; 90(23): 11391-5, 1993; review by Sandrin and McKenzie, Immunol Rev. 1994 October; 141:169-90).

A variety of strategies have been implemented to eliminate or modulate the anti-Gal humoral response caused by xenotransplantation, including enzymatic removal of the epitope with alpha-galactosidases (Stone et al., Transplantation 63: 640-645, 1997), specific anti-gal antibody removal (Ye et al., Transplantation 58: 330-337, 1994), capping of the epitope with other carbohydrate moieties, which failed to eliminate αGT expression (Tanemura et al., J. Biol. Chem. 27321: 16421-16425, 1998 and Koike et al., Xenotransplantation 4: 147-153, 1997) and the introduction of complement inhibitory proteins (Dalmasso et al., Clin. Exp. Immunol. 86:31-35, 1991, Dalmasso et al. Transplantation 52:530-533 (1991)). C. Costa et al. (FASEB J 13, 1762 (1999)) reported that competitive inhibition of αGT in transgenic pigs results in only partial reduction in epitope numbers. Similarly, S. Miyagawa et al. (J. Biol. Chem. 276, 39310 (2000)) reported that attempts to block expression of gal epitopes in N-acetyl-glucosaminyltransferase III transgenic pigs also resulted in only partial reduction of gal epitopes numbers and failed to significantly extend graft survival in primate recipients.

Single allele knockouts of the αGT locus in porcine cells and live animals have been reported. Denning et al. (Nature Biotechnology 19: 559-562, 2001) reported the targeted gene deletion of one allele of the αGT gene in sheep. Harrison et al. (Transgenics Research 11: 143-150, 2002) reported the production of heterozygous αGT knock out somatic porcine fetal fibroblasts cells. In 2002, Lai et al. (Science 295: 1089-1092, 2002) and Dai et al. (Nature Biotechnology 20: 251-255, 2002) reported the production of pigs, in which one allele of the αGT gene was successfully rendered inactive. Ramsoondar et al. (Biol of Reproduc 69, 437-445 (2003)) reported the generation of heterozygous αGT knockout pigs that also express human alpha-1,2-fucosyltransferase (HT), which expressed both the HT and αGT epitopes. PCT publication No. WO 03/055302 to The Curators of the University of Missouri confirms the production of heterozygous αGT knockout miniature swine for use in xenotransplantation in which expression of functional αGT in the knockout swine is decreased as compared to the wildtype.

PCT publication No. WO 94/21799 and U.S. Pat. No. 5,821,117 to the Austin Research Institute; PCT publication No. WO 95/20661 to Bresatec; and PCT publication No. WO 95/28412, U.S. Pat. No. 6,153,428, U.S. Pat. No. 6,413,769 and US publication No. 2003/0014770 to BioTransplant, Inc. and The General Hospital Corporation provide a discussion of the production of αGT negative porcine cells based on the cDNA of the αGT gene.

A recent, major breakthrough in the field of xenotransplantation was the production of the first live pigs lacking any functional expression of αGT (Phelps et al. Science 299:411-414 (2003); see also PCT publication No. WO 04/028243 by Revivicor, Inc. and PCT Publication No. WO 04/016742 by Immerge Biotherapeutics, Inc.).

In one embodiment, animals, tissues and cells are provided that lack any expression of functional αGT (GTKO) and express at least one additional transgene in pancreatic tissues. The additional transgene is typically selected from: 1) an immunomodulator including a complement inhibitor (i.e. CD46 (MCP), CD55, CD59, CR1 and the like) or an immunosuppressor (i.e. CTLA-4, B7 and the like) or 2) an anticoagulant (i.e. TFPI, hirudin, thrombomodulin, EPCR, CD39 and the like). In other embodiments, animals, tissue and cells are provided that lack any expression of functional αGT and express both at least one immunomodulator and at least one anticoagulant in pancreatic tissues. In some embodiments, the pancreatic tissue is porcine. In further embodiments, the pancreatic tissue comprises pancreatic islet cells, or islets, or islet-cell clusters. In particular embodiments, the cells are pancreatic islets. In more particular embodiments, the cells are pancreatic beta cells. In certain embodiments, the cells are insulin producing. In still further embodiments, the cells are islet-like cells. Islet cell clusters can include any one or more of alpha, beta, delta, PP or epsilon cells. Generally, alpha cells producing glucagons make up about 15-20% of total islet cells in native pancreas, bbeta cells producing insulin and amylin make up between about 65-80% of islet cells in native pancreas, delta cells producing somatostatin make up about 3-10% of total islet cells in native pancreas, PP cells producing pancreatic polypeptide make up about 3-5% of total islet cells in native pancreas and epsilon cells producing ghrelin make up <1% of total islet cells in native pancreas (see Elayat et al. (1995). J. Anat. 186: 629-37).

Animals, tissues and cells with a reduced level of expression of functional αGT that concurrently express at least one of the following in pancreatic tissues: 1) an immunomodulator including a complement inhibitor (i.e. CD46, CD55, CD59, CR1 and the like) or an immunosuppressor (i.e. CTLA-4, B7 and the like) or 2) an anticoagulant (i.e. TFPI, hirudin, thrombomodulin, EPCR, CD39 and the like) are also included in this invention. In some embodiments, animals, tissue and cells are provided that have a reduced level of expression of functional αGT and express both at least one immunomodulator and at least one anticoagulant in pancreatic tissues. In some embodiments, the pancreatic tissue is porcine. In further embodiments, the pancreatic tissue comprises pancreatic islet cells. The expression of functional αGT may be reduced by, for example, by at least about 5%, about 10%, about 20%, about 30%, about 40%, about 50%, about 60%, about 70%, about 80%, about 90% or about 95%.

The complete or reduced level of expression of functional αGT may be achieved by any means known to one of skill in the art. In one aspect of the present invention, porcine animals are provided in which one allele of the αGT gene is inactivated via a genetic targeting event. In another aspect of the present invention, porcine animals are provided in which both alleles of the αGT gene are inactivated via a genetic targeting event. In one embodiment, the gene can be targeted via homologous recombination. In other embodiments, the gene can be disrupted, i.e. a portion of the genetic code can be altered, thereby affecting transcription and/or translation of that segment of the gene. For example, disruption of a gene can occur through substitution, deletion ("knock-out") or insertion ("knock-in") techniques. Additional genes for a desired protein or regulatory sequence that modulate transcription of an existing sequence can be inserted.

In embodiments of the present invention, the alleles of the αGT gene are rendered inactive, such that the resultant αGT enzyme can no longer generate Gal on the cell surface. In one embodiment, the αGT gene can be transcribed into RNA, but not translated into protein. In another embodiment, the αGT gene can be transcribed in a truncated form. Such a truncated RNA can either not be translated or can be translated into a nonfunctional protein. In an alternative embodiment, the αGT gene can be inactivated in such a way that no transcription of the gene occurs. In a further embodiment, the αGT gene can be transcribed and then translated into a nonfunctional protein. In some embodiments, the expression of active αGT can be reduced by use of alternative methods, such as those targeting transcription or translation of the gene. For example, the expression can be reduced by use of antisense RNA or siRNA targeting the native αGT gene or an mRNA thereof. In other embodiments, site specific recombinases are used to target a region of the genome for recombination. Examples of such systems are the CRE-lox system and the Flp-Frt systems.

Pigs that possess two inactive alleles of the αGT gene are not naturally occurring. It was previously discovered that while attempting to knockout the second allele of the αGT gene through a genetic targeting event, a point mutation was identified, which prevented the second allele from producing functional αGT enzyme.

Thus, in another aspect of the present invention, the αGT gene can be rendered inactive through at least one point mutation. In one embodiment, one allele of the αGT gene can be rendered inactive through at least one point mutation. In another embodiment, both alleles of the αGT gene can be rendered inactive through at least one point mutation. In one embodiment, this point mutation can occur via a genetic targeting event. In another embodiment, this point mutation can be naturally occurring. In a further embodiment, mutations can be induced in the αGT gene via a mutagenic agent.

In one specific embodiment the point mutation can be a T-to-G mutation at the second base of exon 9 of the αGT gene. Pigs carrying a naturally occurring point mutation in the αGT gene allow for the production of αGT-deficient pigs free of antibiotic-resistance genes and thus have the potential to make a safer product for human use. In other embodiments, at least two, at least three, at least four, at least five, at least ten or at least twenty point mutations can exist to render the αGT gene inactive. In other embodiments, pigs are provided in which both alleles of the αGT gene contain point mutations that prevent any expression of functional αGT enzyme. In a specific embodiment, pigs are provided that contain the T-to-G mutation at the second base of exon 9 in both alleles of the αGT gene.

Another aspect of the present invention provides a porcine animal, in which both alleles of the αGT gene are inactivated, whereby one allele is inactivated by a genetic targeting event and the other allele is inactivated via a mutation. In one embodiment, a porcine animal is provided, in which both alleles of the αGT gene are inactivated, whereby one allele is inactivated by a genetic targeting event and the other allele is inactivated due to presence of a T-to-G point mutation at the second base of exon 9. In a specific embodiment, a porcine animal is provided, in which both alleles of the αGT gene are inactivated, whereby one allele is inactivated via a targeting construct directed to Exon 9 and the other allele is inactivated due to presence of a T-to-G point mutation at the second base of exon 9.

Immunomodulators

Immunomodulators include complement regulators and immunosuppressants.

(i) Complement Regulators

Complement is the collective term for a series of blood proteins and is a major effector mechanism of the immune system. Complement activation and its deposition on target structures can lead to direct complement-mediated cell lysis or can lead indirectly to cell or tissue destruction due to the generation of powerful modulators of inflammation and the recruitment and activation of immune effector cells. Complement activation products that mediate tissue injury are generated at various points in the complement pathway. Inappropriate complement activation on host tissue plays an important role in the pathology of many autoimmune and inflammatory diseases, and is also responsible for many disease states associated with bioincompatibility, e.g. post-cardiopulmonary inflammation and transplant rejection. Complement deposition on host cell membranes is prevented by complement inhibitory proteins expressed at the cell surface.

The complement system comprises a collection of about 30 proteins and is one of the major effector mechanisms of the immune system. The complement cascade is activated principally via either the classical (usually antibody-dependent) or alternative (usually antibody-independent) pathways. Activation via either pathway leads to the generation of C3 convertase, which is the central enzymatic complex of the cascade. C3 convertase cleaves serum C3 into C3a and C3b, the latter of which binds covalently to the site of activation and leads to the further generation of C3 convertase (amplification loop). The activation product C3b (and also C4b generated only via the classical pathway) and its breakdown products are important opsonins and are involved in promoting cell-mediated lysis of target cells (by phagocytes and NK cells) as well as immune complex transport and solubilization. C3/C4 activation products and their receptors on various cells of the immune system are also important in modulating the cellular immune response. C3 convertases participate in the formation of C5 convertase, a complex that cleaves C5 to yield C5a and C5b. C5a has powerful proinflammatory and chemotactic properties and can recruit and activate immune effector cells. Formation of C5b initiates the terminal complement pathway resulting in the sequential assembly of complement proteins C6, C7, C8 and (C9)n to form the membrane attack complex (MAC or C5b-9). Formation of MAC in a target cell membrane can result in direct cell lysis, but can also cause cell activation and the expression/release of various inflammatory modulators.

There are two broad classes of membrane complement inhibitor: inhibitors of the complement activation pathway (inhibit C3 convertase formation), and inhibitors of the terminal complement pathway (inhibit MAC formation). Membrane inhibitors of complement activation include complement receptor 1 (CR1), decay-accelerating factor (DAF or CD55) and membrane cofactor protein (MCP or CD46). They all have a protein structure that consists of varying numbers of repeating units of about 60-70 amino acids termed short consensus repeats (SCR) that are a common feature of C3/C4 binding proteins. Rodent homologues of human complement activation inhibitors have been identified. The rodent protein Cr1 is a widely distributed inhibitor of complement activation that functions similar to both DAF and MCP. Rodents also express DAF and MCP, although Cr1 appears to be functionally the most important regulator of complement activation in rodents. Although there is no homolog of Cr1 found in humans, the study of Cr1 and its use in animal models is clinically relevant.

Control of the terminal complement pathway and MAC formation in host cell membranes occurs principally through the activity of CD59, a widely distributed 20 kD glycoprotein attached to plasma membranes by a glucosylphosphatidylinositol (GPI) anchor. CD59 binds to C8 and C9 in the assembling MAC and prevents membrane insertion.

Host cells are protected from their own complement by membrane-bound complement regulatory proteins like DAF, MCP and CD59. When an organ is transplanted into another species, natural antibodies in the recipient bind the endothelium of the donor organ and activate complement, thereby initiating rapid rejection. It has previously been suggested that, in contrast to human cells, those of the pig are very susceptible to human complement, and it was thought that this was because pig cell-surface complement regulatory proteins are ineffective against human complement. When an organ is transplanted into another species, natural antibodies in the recipient bind the endothelium of the donor organ and activate complement, thereby initiating rapid rejection. Several strategies have been shown to prevent or delay rejection, including removal of IgM natural antibodies and systemic decomplementation or inhibition of complement using sCR1, heparin or C1 inhibitor.

An alternative approach to the problem of rejection is to express human, membrane-bound, complement-regulatory molecules in transgenic pigs. Transgenic pigs expressing decay accelaration factor DAF (CD55), membrane co-factor protein MCP (CD46) and membrane inhibitor of reactive lysis, MIRL (CD59) have been generated. (see Klymium et al. Mol Reprod Dev (2010)77:209-221). These human inhibitors have been shown to be abundantly expressed on porcine vascular endothelium. Ex vivo perfusion of hearts from control animals with human blood caused complement-mediated destruction of the organ within minutes, whereas hearts obtained from transgenic animals were refractory to complement and survived for hours.

The rationale for expressing human complement regulatory proteins in pig organs to "humanize" them as outlined above is based on the assumption that endogenous pig regulatory proteins are inefficient at inhibiting human complement and thus will contribute little to organ survival in the context of xenotransplantation. Studies involving pig islet xenotransplantation in non-human primates have shown the importance of complement activation, including deposition of complement components (C3, C5, C9, SC5b-9), and significant binding of IgM observed in the islet grafts within 12-24 hours post-transplant. The complement activation can play an important role in the inflammatory response associated with IBMIR which prevents a major portion of infused islets from engrafting (Cantarovich et al., Xenotransplantation 9:25, 2002; Kirchhof et al., Xenotransplantation 11(5), 396, 2004; Tjernberg, et al., Transplantation. 2008 Apr. 27; 85(8): 1193-9). In addition, soluble complement inhibitors can prevent complement-mediated lysis of islets in vitro (Bennet, et al., Transplantation 69(5):711, 2000).

U.S. Pat. No. 7,462,466 to Morgan et al. describes the isolation and characterization of porcine analogues of several of the human complement regulatory proteins (CRP). The studies illustrated that pig organs expressing human complement regulatory protein molecules were resistant to complement damage not because they expressed human CRP molecules, but because they expressed greatly increased amounts of functional CRP molecules. Morgan et al. found that increased expression of porcine CRP could be equally effective in protecting the donor organ from complement damage leading to hyperacute rejection as donor organs expressing human complement regulatory proteins.

CD46 has been characterized as a protein with regulatory properties able to protect the host cell against complement mediated attacks activated via both classical and alternative pathways (Barilla-LaBarca, M. L. et al., J. Immunol. 168, 6298-6304 (2002)). hCD46 may offer protection against complement lysis during inflammation and humoral rejection mediated by low levels of natural or induced anti-Gal or anti-nonGal antibodies. As a result, more islets are able to engraft and be subsequently better protected against rejection, thus reducing immunosuppression needs.

In one embodiment of the present invention, animals, tissues and cells are provided that express at least one complement regulator and either lack any expression of functional αGT or express at least one of the following in pancreatic tissues: 1) an immunosuppressor (i.e. CTLA-4, B7 and the like) or 2) an anticoagulant (i.e. TFPI, hirudin, thrombomodulin, EPCR, CD39 and the like).

In other embodiments, animals, tissue and cells are provided that express at least one complement regulator, lack any expression of functional αGT and express at least one of the following in pancreatic tissues: 1) an immunosuppressor (i.e. CTLA-4, B7 and the like) or 2) an anticoagulant (i.e. TFPI, hirudin, thrombomodulin, EPCR, CD39 and the like).

In still further embodiments, animals, tissue and cells are provided that express at least one complement regulator, lack any expression of functional αGT, express at least one immunosuppressor (i.e. CTLA-4, B7 and the like), and express at least one anticoagulant (i.e. TFPI, hirudin, thrombomodulin, EPCR, CD39 and the like) in pancreatic tissue. In some embodiments, the pancreatic tissue is porcine. In further embodiments, the pancreatic tissue comprises pancreatic islet cells.

In some embodiments, the complement regulator may be a complement inhibitor. In further embodiments, the complement inhibitor may be a membrane complement inhibitor. The membrane complement inhibitor may be either an inhibitor of the complement activation pathway (inhibit C3 convertase formation) or an inhibitor of the terminal complement pathway (inhibit MAC formation). Membrane inhibitors of complement activation include complement receptor 1 (CR1), decay-accelerating factor (DAF or CD55), membrane cofactor protein (MCP or CD46) and the like. Membrane inhibitors of the terminal complement pathway may include CD59 and the like. In instances where complement regulators are expressed, two or more different complement regulators may be expressed.

In some embodiments of the present invention, the complement regulators are human complement regulators. In other embodiments, the complement regulators are porcine complement regulators.

In a particular embodiment, the compliment inhibitor (e.g., CD46 or DAF) is expressed in every cell where it would normally be expressed. In another embodiment, the compliment inhibitor is expressed ubiquitously.

In one embodiment, the animals, tissues or cells according to the present invention, can be modified to transgenically express the one or more complement regulators. The animals, tissues or cells can be modified to express a complement regulator peptide, a biologically active fragment or derivative thereof. In one embodiment, the complement regulator peptide is the full length complement regulator. In a further embodiment, the complement regulator peptide can contain less than the full length complement regulator protein.

Any human or porcine complement regulator sequences or biologically active portion or fragment thereof known to one skilled in the art can be according to the compositions and methods of the present invention. In additional embodiments, any consensus complement regulator peptide can be used according to the present invention. In another embodiment, nucleic acid and/or peptide sequences at least 80%, 85%, 90% or 95% homologous to the complement regulator peptides and nucleotide sequences described herein. In further embodiments, any fragment or homologous sequence that exhibits similar activity as complement regulator can be used.

(ii) Immunosuppressants

An "immunosuppressant" transgene is capable of down-regulating an immune response. For any type of transplantation procedure, a balance between efficacy and toxicity is a key factor for its clinical acceptance. With respect to islet transplantation, a further concern is that many of the current immunosuppressive agents in particular glucocortecoids or a calcineurin inhibitor, such as Tarcolimus, damage beta cells or induce peripheral insulin resistance (Zeng et al. Surgery (1993) 113: 98-102). A steroid-free immunosuppressive protocol ("Edmonton protocol") that includes sirolimus, low dose Tarcolimus, and a monoclonal antibody (mAb) against IL-2 receptor has been used in a trial of islet transplantation alone for patients with type-1 diabetes (Shapiro, A. M. J. et al, (2000), N. Eng. J. Med., 343: 230-238). The recent success using the "Edmonton protocol" has renewed enthusiasm for the use of islet transplantation to treat diabetes. However, concerns regarding toxicity of the Tacrolimus may limit the application of this therapy in humans.

Biological agents that block key T cell costimulatory signals, in particular the CD28 pathway, are potential alternatives to protect islets. Examples of agents that block the CD28 pathway include but are not limited to soluble CTLA4 including mutant CTLA4 molecules.

T-cell activation is involved in the pathogenesis of transplant rejection. Activation of T-cells requires at least two sets of signaling events. The first is initiated by the specific recognition through the T-cell receptor of an antigenic peptide combined with major histocompatibility complex (MHC)

molecules on antigen presenting cells (APC5). The second set of signals is antigen nonspecific and is delivered by T-cell costimulatory receptors interacting with their ligands on APCs. In the absence of costimulation, T-cell activation is impaired or aborted, which may result in an antigen specific unresponsive state of clonal anergy, or in deletion by apoptotic death. Hence, the blockade of T-cell costimulation may provide an approach for suppressing unwanted immune responses in an antigen specific manner while preserving normal immune functions. (Dumont, F. J. 2004 Therapy 1, 289-304).

Of several T cell costimulatory pathways identified to date, the most prominent is the CD28 pathway. CD28, a cell surface molecule expressed on T-cells, and its counter receptors, the B7.1 (CD8O) and B7.2 (CD86) molecules, present on dendritic cells, macrophages, and B-cells, have been characterized and identified as attractive targets for interrupting T-cell costimulatory signals. A second T-cell surface molecule homologous to CD28 is known as cytoxic T-lymphocyte associated protein (CTLA4). CTLA4 is a cell surface signaling molecule, but contrary to the actions of CD28, CTLA4 negatively regulates T cell function. CTLA4 has 20-fold higher affinity for the B7 ligands than CD28. The gene for human CTLA4 was cloned in 1988 and chromosomally mapped in 1990 (Dariavach et al., Eur. J. Immunol. 18:1901-1905 (1988); Lafage-Pochitaloff et al., Immunogenetics 31:198-201 (1990); U.S. Pat. No. 5,977,318).

The CD28/B7 pathway has become an attractive target for interrupting T cell costimulatory signals. The design of a CD28/B7 inhibitor has exploited the endogenous negative regulator of this system, CTLA4. A CTLA4-immunoglobulin (CTLA4-Ig) fusion protein has been studied extensively as a means to inhibit T cell costimulation. A difficult balance must be reached with any immunosuppressive therapy; one must provide enough suppression to overcome the disease or rejection, but excessive immunosuppression will inhibit the entire immune system. The immunosuppressive activity of CTLA4-Ig has been demonstrated in preclinical studies of animal models of organ transplantation and autoimmune disease. Soluble CTLA4 has recently been tested in human patients with kidney failure, psoriasis and rheumatoid arthritis and has been formulated as a drug developed by Bristol-Myers Squibb (Abatacept, soluble CTLA4-Ig) that has been approved for the treatment of rheumatoid arthritis. This drug is the first in the new class of selective T cell costimulation modulators. Bristol-Myers Squibb is also conducting Phase II clinical trials with Belatacept (LEA29Y) for allograft kidney transplants. LEA29Y is a mutated form of CTLA4, which has been engineered to have a higher affinity for the B7 receptors than wild-type CTLA4, fused to immunoglobulin. Repligen Corporation is also conducting clinical trials with its CTLA4-Ig for idiopathic thrombocytopenic purpura. U.S. Pat. No. 5,730,403 entitled "Methods for protecting allogeneic islet transplant using soluble CTLA4 mutant molecules", describes the use of soluble CTLA4-Ig and CTLA4 mutant molecules to protect allogeneic islet transplants.

Although CTLA-4 from one organism is able to bind to B7 from another organism, the highest avidity is found for allogeneic B7. Thus, while soluble CTLA-4 from the donor organism can thus bind to both recipient B7 (on normal cells) and donor B7 (on xenotransplanted cells), it preferentially binds B7 on the xenograft. Thus in the embodiments of the invention comprising porcine animals or cells for xenotransplantation, porcine CTLA4 is typical. PCT Publication No. WO 99/5 7266 by Imperial College describes a porcine CTLA4 sequence and the administration of soluble CTLA4-Ig for xenotransplantation therapy. Vaughn A. et al., J Immunol (2000) 3175-3181, describes binding and function of soluble porcine CTLA4-Ig. Porcine CTLA4-Ig binds porcine (but not human) B7, blocking CD28 on recipient Tcells and rendering these local T cells anergic without causing global T cell immunosuppression (see Mirenda et. al., Diabetes 54:1048-1055, 2005).

To date, much of the research on CTLA4-Ig as an immunosuppressive agent has focused on administering soluble forms of CTLA4-Ig to the patient. Transgenic mice engineered to express CTLA4-Ig have been created and subject to several lines of experimentation. Ronchese et al. examined immune system function generally after expression of CTLA4 in mice (Ronchese et al. J Exp Med (1994) 179: 809; Lane et al. J Exp Med. (1994) March 1; 179(3):819). Sutherland et al. (Transplantation. 2000 69(9):1806-12) described the protective effect of CTLA4-Ig secreted by transgenic fetal pancreas allografts in mice to test the effects of transgenically expressed CTLA4-Ig on allogenic islet transplantation. Lui et al. (J Immunol Methods 2003 277: 171-183) reported the production of transgenic mice that expressed CTLA4-Ig under control of a mammary specific promoter to induce expression of soluble CTLA4-Ig in the milk of transgenic animals for use as a bioreactor.

PCT Publication No. WO 01/30966 by Alexion Phamaceuticals Inc. describes chimeric DNA constructs containing the T cell inhibitor CTLA-4 attached to the complement protein CD59, as well as transgenic porcine cells, tissues, and organs containing the same. PCT Publication No. WO2007035213 (Revivicor) describes transgenic porcine animals that have been genetically modified to express CTLA4-Ig.

Although the development of CTLA4-Ig expressing animals has been suggested, these animals are severely immunocompromised. Recently, pigs produced by Revivicor, Inc. expressing CTLA4-Ig ubiquitously using a CAG enhancer/promoter were found to have an immunocompromised phenotype and were not viable in a typical husbandry environment (see Example 11).

In the current invention, the islet lineage specific enhancer from the Pdx-1 gene, known to direct gene expression in both fetal and adult islets (Lomedico et al., 1979), in combination with the promoter from the rat Ins2 gene (Gerrish et al., 2004) was utilized to construct a vector for driving expression of an immunosuppressant transgene, locally and specifically, in the islets of the resulting transgenic animals.

Additional immunomodulators, and in particular immunosuppressors can be expressed in the animals, tissues or cells. For example, genes which have been inactivated in mice to produce an immuno compromised phenotype, can be cloned and disrupted by gene targeting in pigs. Some genes which have been targeted in mice and may be targeted to produce immuno compromised pigs include beta 2-microglobulin (MHC class I deficiency, Koller et al., Science, 248:1227-1230), TCR alpha, TCR beta (Mombaerts et al., Nature, 360: 225-231), RAG-1 and RAG-2 (Mombaerts et al., (1992) Cell 68, 869-877, Shinkai, et al., (1992) Cell 68, 855-867, U.S. Pat. No. 5,859,307).

In one embodiment, the animals or cells according to the present invention, can be modified to transgenically express a cytoxic T-lymphocyte associated protein 4-immunoglobin (CTLA4). The animals or cells can be modified to express CTLA4 peptide or a biologically active fragment (e.g., extracellular domain, truncated form of the peptide in which at least the transmembrane domain has been removed) or derivative thereof. The peptide may be, e.g., human or porcine. The CTLA4 peptide can be mutated. Mutated peptides may have higher affinity than wildtype for porcine and/or human B7 molecules. In one specific embodiment, the mutated CTLA4 can be CTLA4 (Glu104, Tyr29). The CTLA4 peptide can be modified such that it is expressed intracellularly. Other modifications of the CTLA4 peptide include addition of a endoplasmic reticulum retention signal to the N or C terminus The endoplasmic reticiulum retention signal may be, e.g., the sequence KDEL. The CTLA4 peptide can be fused to a peptide dimerization domain or an immunoglobulin (Ig) molecule. The CTLA4 fusion peptides can include a linker sequence that can join the two peptides. In another embodiment, animals lacking expression of functional immunoglobulin, produced according to the present invention, can be administered a CTLA4 peptide or a variant thereof (pCTLA4-Ig, or hCTLA4-Ig (Abatacept/Orencia, or Belatacept) as a drug to suppress their T-cell response. As used herein, CTLA4 is used to refer to any of these variants or those known in the art, e.g., CTLA4-Ig.

In one embodiment, the CTLA4 peptide is the full length CTLA4. In a further embodiment, the CTLA4 peptide can contain less than the full length CTLA4 protein. In one embodiment, the CTLA4 peptide can contain the extracellular domain of a CTLA-4 peptide. In a particular embodiment, the CTLA4 peptide is the extracellular domain of CTLA4. In still further embodiments, the present invention provides mutated forms of CTLA4. In one embodiment, the mutated form of CTLA4 can have higher affinity than wild type for porcine and/or human B7. In one specific embodiment, the mutated CTLA4 can be human CTLA4 (Glu104, Tyr29).

In one embodiment, the CTLA4 can be a truncated form of CTLA4, in which at least the transmembrane domain of the protein has been removed. In another embodiment, the CTLA4 peptide can be modified such that it is expressed intracellularly. In one embodiment, a golgi retention signal can be added to the N or C terminus of the CTLA4 peptide. In one embodiment, the golgi retention signal can be the sequence KDEL, which can be added to the C or N terminal of the CTLA4 peptide. In further embodiments, the CTLA4 peptide can be fused to a peptide dimerization domain. In one embodiment, the CTLA4 peptide can be fused to an immunoglobulin (Ig). In another embodiment, the CTLA4 fusion peptides can include a linker sequence that can join the two peptides.

Any human CTLA4 sequences or biologically active portion or fragment thereof known to one skilled in the art can be according to the compositions and methods of the present invention. Non-limiting examples include, but are not limited to the following Genbank accession numbers that describe human CTLA4 sequences: NM005214.2; BC074893.2; BC074842.2; AF414120.1; AF414120; AY402333; AY209009.1; BC070162.1; BC069566.1; L15006.1; AF486806.1; AC010138.6; AJ535718.1; AF225900.1; AF225900; AF411058.1; M37243.1; U90273.1; and/or AF316875.1. Further nucleotide sequences encoding CTLA4 peptides can be selected from those including, but not limited to the following Genbank accession numbers from the EST database: CD639535.1; AI733018.1; BM997840.1; BG536887.1; BG236211.1; BG058720.1; AI860i99.1; AW207094.1; AA210929.1; AI791416.1; BX113243.1; AW515943.1; BE837454.1; AA210902.1; BF329809.1; AI819438.1; BE837501.1; BE837537.1; and/or AA873138.1.

In additional embodiments, any consensus CTLA4 peptide can be used according to the present invention. In another embodiment, nucleic acid and/or peptide sequences at least 80%, 85%, 90% or 95% homologous to the native CTLA4 peptides and nucleotide sequences. In further embodiments, any fragment or homologous sequence that exhibits similar activity as CTLA4 can be used.

In other embodiments, the amino acid sequence which exhibits T cell inhibitory activity can be amino acids 38 to 162 of the porcine CTLA4 sequence or amino acids 38 to 161 of the human CTLA4 sequence (see, for example, PCT Publication No. WO 01/30966). In one embodiment, the portion used should have at least about 25% and preferably at least about 50% of the activity of the parent molecule.

In other embodiments, the CTLA4 nucleic acids and peptides of the present invention can be fused to immunoglobulin genes and molecules or fragments or regions thereof. Reference to the CTLA4 sequences of the present invention include those sequences fused to immunoglobulins.

In one embodiment, the Ig can be a human Ig. In another embodiment, the Ig can be IgG, in particular, IgG1. In another embodiment, the Ig can be the constant region of IgG. In a particular embodiment, the constant region can be the Cγ1 chain of IgG1. In one particular embodiment of the present invention, the extracelluar domain of porcine CTLA4 can be fused to human Cγ1 Ig. In another particular embodiment, the extracellular domain of human CTLA4 can be fused to IgG1 or IgG4. In a further particular embodiment, the extracellular domain of mutated CTLA4 (Glu 104, Tyr 29) can be fused to IgG1.

(iii) Other Immunomodulators

Other immunodulators that can be used include class II transactivators (CIITA) and mutants thereof PDL1, PDL2, tumor necrosis factor-α-related apoptosis-inducing ligand (TRAIL), Fas ligand (FasL, CD95L) integrin-associated protein (CD47), HLA-E, HLA-DP, HLA-DQ, or HLA-DR.

(a) CIITA: The class II transactivator (CIITA) is a bi- or multifunctional domain protein that acts as a transcriptional activator and plays a critical role in the expression of MHC class II genes. It has been previously demonstrated that a mutated form of the human CIITA gene, coding for a protein lacking the amino terminal 151 amino acids, acts as a potent dominant-negative suppressor of HLA class II expression (Yun et al., Int Immunol. 1997 October; 9(10):1545-53). Porcine MHC class II antigens are potent stimulators of direct T-cell recognition by human CD4+ T cells and are, therefore, likely to play an important role in the rejection responses to transgenic pig donors in clinical xenotransplantation. It was reported that one mutated human CIITA construct was effective in pig cells, markedly suppressing IFN[gamma]-induced as well as constitutive porcine MHC class II expression. Moreover, stably transfected porcine vascular endothelial cell lines carrying mutated human CIITA constructs failed to stimulate direct T-cell xenorecognition by purified human CD4+ T cells (Yun et al., Transplantation. 2000 Mar. 15; 69(5):940-4). Organs, tissues and cells from CIITA-DN transgenic animals could induce a much reduced T-cell rejection responses in human recipients. In combination with other transgenes, transgenic expression of a mutated CIITA might enable long-term xenograft survival with clinically acceptable levels of immunosuppression.

(b) PDL1, PDL2: Typical costimulatory molecules for T-cell activation are CD80/86 or CD40. In addition to these positive costimulatory pathways over the past several years, new costimulatory pathways that mediate negative signals and are important for the regulation of T-cell activation have been found. One of these newer pathways is the pathway consisting of Programmed death 1 (PD-1) receptor and its ligands, PD-L1 and PD-L2. The PD-1 receptor is not expressed in resting cells but is upregulated after T and B cell activation. PD-1 contains a cytoplasmatic immunoreceptor tyrosine-based switch motif and binding of PD-L1 or PD-L2 to PD-1 leads to inhibitory signals in T cells. Recent data suggest that PD1/PDLigand pathways may play a role in the control of T-cell subsets exhibiting regulatory activity. In mice, PD-1 signals have been shown to be required for the suppressive activity of regulatory T cells (Treg) and the generation of adaptive Treg. These observations suggest that PD-1/PDLig and interactions do not only inhibit T-cell responses but may also provoke immunoregulation. Several lines of evidence demonstrate that PD-1/PDLigand pathways can control engraftment and rejection of allografts implying that these molecules are interesting targets for immunomodulation after organ transplantation. Indeed, prolongation of allograft survival could be obtained by PDL1Ig gene transfer to donor hearts in a rat transplantation model. Moreover, enhancing PD-1 signaling by injection of PD-L1Ig has also been reported to protect grafts from rejection in mice. Recent data also show that overexpression of PD-L1IG on islet grafts in mice can partially prolong islet graft survival. Transgenic expression of human PD-L1 or PD-L2 in pig cells and tissues should reduce early human anti-pig T-cell responses initiated via the direct route of sensitization (Plege et al., Transplantation. 2009 Apr. 15; 87(7):975-82). By the induction of Treg it might also be possible to control T cells sensitized to the xenograft through the indirect route that is required to achieve long-lasting tolerance.

(c) TRAIL/Fas L:

Expression of apoptosis inducing ligands, such as Fas ligand (FasL, CD95L) or tumor necrosis factor-α-related apoptosis-inducing ligand (TRAIL, Apo-2L) may eliminate T cells attacking a xenograft. TRAIL is a type II membrane protein with an extracellular domain homologous to that of other tumor necrosis factor family members showing the highest amino acid identity to FasL (28%). TRAIL exerts its apoptosis-inducing action preferentially on tumor cells. In normal cells, binding of TRAIL receptors does not lead to cell death. Recent studies have shown that the cytotoxic effects of immune cells, including T cells, natural killer cells, macrophages, and dendritic cells, are mediated at least partly by TRAIL. Expression of human TRAIL in transgenic pigs may provide a reasonable strategy for protecting pig tissues against cell-mediated rejection after xenotransplantation to primates. Stable expression of human TRAIL has been achieved in transgenic pigs and TRAIL expressed has been shown to be biologically functional in vitro (Klose et al., Transplantation. 2005 Jul. 27; 80(2):222-30). (d) CD47: CD47, known as integrin-associated protein, is a ubiquitously expressed 50-kDa cell surface glycoprotein that serves as a ligand for signal regulatory protein (SIRP)α (also known as CD172a, SHPS-1), an immune inhibitory receptor on macrophages. CD47 and SIRPα constitute a cell-cell communication system (the CD47-SIRPα system) that plays important roles in a variety of cellular processes including cell migration, adhesion of B cells, and T cell activation. In addition, the CD47-SIRPα system is implicated in negative regulation of phagocytosis by macrophages. CD47 on the surface of several cell types (i.e., erythrocytes, platelets, or leukocytes) can protect against phagocytosis by macrophages by binding to the inhibitory macrophage receptor SIRPα. The role of CD47-SIRPα interactions in the recognition of self and inhibition of phagocytosis has been illustrated by the observation that primary, wild-type mouse macrophages rapidly phagocytose unopsonized RBCs obtained from CD47-deficient mice but not those from wild-type mice. It has also been reported that through its SIRPα receptors, CD47 inhibits both Fcγ and complement receptor-mediated phagocytosis. It has been demonstrated that porcine CD47 does not induce SIRPα tyrosine phosphorylation in human macrophage-like cell line, and soluble human CD47-Fc fusion protein inhibits the phagocytic activity of human macrophages toward porcine cells. It was also indicated that manipulation of porcine cells for expression of human CD47 radically reduces the susceptibility of the cells to phagocytosis by human macrophages (Ide et al., Proc Natl Acad Sci USA. 2007 Mar. 20; 104(12): 5062-6). Expression of human CD47 on porcine cells could provide inhibitory signaling to SIRPα on human macrophages, providing an approach to preventing macrophage-mediated xenograft rejection.

(e) NK Cell Response. HLA-E/Beta 2 Microglobulin and HLA-DP, HLA-DQ, HLA-DR:

Human natural killer (NK) cells represent a potential hurdle to successful pig-to-human xenotransplantation because they infiltrate pig organs perfused with human blood ex vivo and lyse porcine cells in vitro both directly and, in the presence of human serum, by antibody-dependent cell-mediated cytotoxicity. NK cell autoreactivity is prevented by the expression of major histocompatibility complex (MHC) class I ligands of inhibitory NK receptors on normal autologous cells. The inhibitory receptor CD94/NKG2A that is expressed on a majority of activated humanNK cells binds specifically to human leukocyte antigen (HLA)-E. The non-classical human MHC molecule HLA-E is a potent inhibitory ligand for CD94/NKG2A-bearing NK cells and, unlike classical MHC molecules, does not induce allogeneic T-cell responses. HLA-E is assembled in the endoplasmic reticulum and transported to the cell surface as a stable trimeric complex consisting of the HLA-E heavy chain, β2-microglobulin (β2 m), and a peptide derived from the leader sequence of some MHC class 1 molecules. The expression of HLA-E has been shown to provide partial protection against xenogeneic human NK cell cytotoxicity (Weiss et al., Transplantation. 2009 Jan. 15; 87(1):35-43). Transgenic expression of HLA-E on pig organs has the potential to substantially alleviate human NK cell-mediated rejection of porcine xenografts without the risk of allogeneic responses. In addition, transgenic pigs carrying other HLA genes have been successfully generated with the goal of "humanizing" porcine organs, tissues, and cells (Huang et al., Proteomics. 2006 November; 6(21):5815-25, see also U.S. Pat. No. 6,639,122).

Anti-Coagulants

The islet-blood reaction is characterized by accelerated clotting and platelet consumption, resulting in loss of 80-90% of the islet mass in the first 48 hours, and has been shown to be associated with activation of the complement lysis system, and upregulation of tissue factor on the islets (Johansson et al. Diabetes, 2005, 54:1755; Moberg et al, Lancet, 2002, 360: 1999-2000; Berman et al., Transplantion 2007, 84:308-313). Previously, these anticoagulant transgenes have been introduced into animals with the goal of expressing them in the porcine endothelium for organ xenotransplantation. In the current invention, the islet lineage specific enhancer from the Pdx-1 gene, known to direct gene expression in both fetal and adult islets (Lomedico P et al., Cell, 1979, 18:545), in combination with the promoter from the rat Ins2 gene (Gerrish K et al., Mol. Endocrinol., 2004, 18(3): 533) was utilized to construct a vector for driving expression of an anticoagulant, locally and specifically, in the islets of the resulting transgenic animals.

Tissue factor pathway inhibitor (TFPI) is a single-chain polypeptide which can reversibly inhibit Factor Xa (Xa) and Thrombin (Factor IIa) and thus inhibits TF dependent coagulation. For a review of TFPI, please see Crawley and Lane (Arterioscler Thromb Vasc Biol. 2008, 28(2):233-42). Dorling and colleagues generated transgenic mice expressing a fusion protein consisting of the three Kunitz domains of human TFPI linked to the transmembrane/cytoplasmic domains of human CD4, with a P-selectin tail for targeting to Weibel-Palade intracellular storage granules (Chen D, et al. Am J Transplant 2004; 4: 1958-1963). The resulting activation-dependent display of TFPI on the endothelium was sufficient to completely inhibit thrombosis-mediated acute humoral rejection of mouse cardiac xenografts by cyclosporine-treated rats. There was also a suggestion that effective regulation of coagulation may prevent chronic rejection. Similar results were obtained with transgenic mouse hearts expressing a hirudin/CD4/P-selectin fusion protein, indicating that inhibition of thrombin generation or activity was the key to protection in this model.

Hirudin is a naturally occurring peptide in the salivary glands of medicinal leeches (such as Hirudo medicinalis) and is a potent inhibitor of thrombin. Dorling and coworkers (Chen et al., J Transplant. 2004 December; 4(12):1958-63) also generated transgenic mice expressing membrane-tethered hirudin fusion proteins, and transplanted their hearts into rats (mouse-rat Xeno-Tx). In contrast to control non-transgenic mouse hearts, which were all rejected within 3 days, 100% of the organs from both strains of transgenic mice were completely resistant to humoral rejection and survived for more than 100 days when T-cell-mediated rejection was inhibited by administration of ciclosporin A. Riesbeck et al., (Circulation. 1998 Dec. 15; 98(24):2744-52) also explored the expression of hirudin fusion proteins in mammalian cells as a strategy for prevention of intravascular thrombosis. Expression in cells reduced local thrombin levels and inhibited fibrin formation. Therefore, hirudin is another anticoagulant transgene of interest for preventing the thrombotic effects present in xenotransplantation.

Thrombomodulin (TM) functions as a cofactor in the thrombin-induced activation of protein C in the anticoagulant pathway by forming a 1:1 stoichiometric complex with thrombin. Endothelial cell protein C receptor (EPCR) is an N-glycosylated type I membrane protein that enhances the activation of protein C. The role of these proteins in the protein C anticoagulant system is reviewed by Van de Wouwer et al., Arterioscler Thromb Vasc Biol. 2004 August; 24(8):1374-83. Expression of these and other anticoagulant transgenes has been explored by various groups to potentially address the coagulation barriers to xenotransplantation (reviewed by Cowan and D'Apice, Cur Opin Organ Transplant. 2008 April; 13(2):178-83). Esmon and coworkers (Li et al., J Thromb Haemost. 2005 July; 3(7):1351-9 over-expressed EPCR on the endothelium of transgenic mice and showed that such expression protected the mice from thrombotic challenge. Iino et al., (J Thromb Haemost. 2004 May; 2(5):833-4), suggested ex-vivo over expression of TM in donor islets via gene therapy as a means to prevent thrombotic complications in islet transplantation.

CD39 is a major vascular nucleoside triphosphate diphosphohydrolase (NTPDase), and converts ATP, and ADP to AMP and ultimately adenosine. Extracellular adenosine plays an important role in thrombosis and inflammation, and thus has been studied for its beneficial role in transplantation (reviewed by Robson et al. Semin Thromb Hemost. 2005 April; 31(2):217-33). Recent studies have shown that CD39 has a major effect in reducing the inflammatory response (Beldi et al., Front Biosci, 2008, 13:2588-2603). Transgenic mice expressing hCD39 exhibited impaired platelet aggregation, prolonged bleeding times, and resistance to systemic thromboembolism in a heart transplant model (Dwyer et al., J Clin Invest. 2004 May; 113(10): 1440-6). They were also shown to express CD39 on pancreatic islets and when incubated with human blood, these islets significantly delayed clotting time compared to wild type islets (Dwyer et al., Transplantation. 2006 Aug. 15; 82(3):428-32). Preliminary efforts at expressing hCD39 at high levels from a constitutive promoter system in transgenic pigs, showed high post-natal lethality (Revivicor, Inc., unpublished data). Thus there is a need to express anticoagulant transgenes in pigs in a manner that does not compromise the animal's well being, yet still provides adequate levels of expression for utility in clinical xenotransplantation.

Cytoprotective Transgenes

The present invention includes cytoprotective transgenes ("cytoprotectants'). Cytoprotective transgenes are considered to include anti-apoptotics, anti-oxidants and anti-inflammatories. Examples include:

(a) A20:

A20 provides anti-inflammatory and anti-apoptotic activity. Vascularized transplanted organs may be protected against endothelial cell activation and cellular damage by anti-inflammatory, anticoagulant and/or anti-apoptotic molecules. Among genes with great potential for modulation of acute vascular rejection (AVR) is the human A20 gene (hA20) that was first identified as a tumor necrosis factor (TNF)-α inducible factor in human umbilical vein endothelial cells. Human A20 has a double cytoprotective function by protecting endothelial cells from TNF-mediated apoptosis and inflammation, via blockade of several caspases, and the transcription factor nuclear factor-κB, respectively. Viable A20 transgenic piglets have been produced and in these animals expression of hA20 was restricted to skeletal muscle, heart and PAECs which were protected against TNF mediated apoptosis by hA20 expression and at least partly against CD95 (Fas)L-mediated cell death. In addition, cardiomyocytes from hA20-transgenic-cloned pigs were partially protected against cardiac insults (Oropeza et al., Xenotransplantation. 2009 November; 16(6):522-34).

(b) HO-1:

HO provides anti-inflammatory, anti-apoptotic, and anti-oxidant activity. Heme oxygenases (HOs), rate-limiting enzymes in heme catabolism, also named HSP32, belong to members of heat shock proteins, wherein the heme ring is cleaved into ferrous iron, carbon monoxide (CO) and biliverdin that is then converted to bilirubin by biliverdin reductase. Three isoforms of HOs, including HO-1, HO-2 and HO-3, have been cloned. The expression of HO-1 is highly inducible, whereas HO-2 and HO-3 are constitutively expressed (Maines M D et al., Annual Review of Pharmacology & Toxicology 1997; 37:517-554, and Choi A M et al., American Journal of Respiratory Cell & Molecular Biology 1996; 15:9-19). An analysis of HO-1−/− mice suggests that the gene encoding HO-1 regulates iron homeostasis and acts as a cytoprotective gene having potent antioxidant, anti-inflammatory and anti-apoptotic effects (Poss K D et al., Proceedings of the National Academy of Sciences of the United States of America 1997; 94:10925-10930, Poss K D et al., Proceedings of the National Academy of Sciences of the United States of America 1997; 94:10919-10924, and Soares M P et al., Nature Medicine 1998; 4:1073-1077). Similar findings were recently described in a case report of HO-1 deficiency in humans (Yachie A et al., Journal of Clinical Investigation 1999; 103:129-135). The molecular mechanisms responsible for the cytoprotective effects of HO-1, including anti-inflammation, anti-oxidation and anti-apoptosis, are mediated by its' reaction products. HO-1 expression can be modulated in vitro and in vivo by protoporphyrins with different metals. Cobalt protoporphyrins (CoPP) and iron protoporphyrins (FePP) can up-regulate the expression of HO-1. In contrast, tin protoporphyrins (SnPP) and zinc protoporphyrins (ZnPP) inhibit the activity of HO-1 at the protein level. Recently, it has been proved that the expression of HO-1 suppresses the rejection of mouse-to-rat cardiac transplants (Sato K et al., J. Immunol. 2001; 166:4185-4194), protects islet cells from apoptosis, and improves the in vivo function of islet cells after transplantation (Pileggi A et al., Diabetes 2001; 50: 1983-1991). It has also been proved that administration of HO-1 by gene transfer provides protection against hyperoxia-induced lung injury (Otterbein L E et al., J Clin Invest 1999; 103: 1047-1054), upregulation of HO-1 protects genetically fat Zucker rat livers from ischemia/reperfusion injury (Amersi F et al., J Clin Invest 1999; 104: 1631-1639), and ablation or expression of HO-1 gene modulates cisplatin-induced renal tubular apoptosis (Shiraishi F et al., Am J Physiol Renal Physiol 2000; 278:F726-F736). In transgenic animal models, it was shown that over-expression of HO-1 prevents the pulmonary inflammatory and vascular responses to hypoxia (Minamino T et al., Proc. Natl. Acad. Sci. USA 2001; 98:8798-8803) and protects heart against ischemia and reperfusion injury (Yet S F, et al., Cir Res 2001; 89:168-173). Pigs carrying a HO-1 transgene have been produced however clinical effects related to their use in xenotransplantation were not reported (U.S. Pat. No. 7,378,569).

(c) FAT-1:

FAT-1 provides anti-inflammatory activity. Polyunsaturated fatty acids (PUFAs) play a role in inhibiting (n-3 class) inflammation. Mammalian cells are devoid of desaturase that converts n-6 to n-3 PUFAs. Consequently, essential n-3 fatty acids must be supplied with the diet. Unlike mammals, however, the free-living nematode *Caenorhabditis elegans* expresses a n-3 fatty acid desaturase that introduces a double bond into n-6-fatty acids at the n-3 position of the hydrocarbon chains to form n-3 PUFAs. Transgenic mice have been generated that express the *C. elegans* fat-1 gene and, consequently, are able to efficiently convert dietary PUFAs of the 6 series to PUFAs of 3-series, such as EPA (20:5 n-3) and DHA (22-6 n-3). (Kang et al., Nature. 2004 Feb. 5; 427(6974):504). Another group produced a transgenic mouse model wherein the codons of fat-1 cDNA were further optimized for efficient translation in mammalian systems; endogenous production of n-3 PUFAs was achieved through overexpressing a *C. elegans* n-3 fatty acid desaturase gene, mfat-1. This group showed that cellular increase of n-3 PUFAs and reduction of n-6 PUFAs through transgenic expression of mfat-1 enhanced glucose-, amino acid-, and GLP-1-stimulated insulin secretion in isolated pancreatic islets of the mice, and rendered the islets strongly resistant to cytokine-induced cell death (Wei et al., Diabetes. 2010 February; 59(2):471-8).

(d) Soluble TNF-Alpha Receptor (sTNFR1):

Tumor necrosis factor (TNF, cachexin or cachectin and formally known as tumor necrosis factor-alpha) is a cytokine involved in systemic inflammation and is a member of a group of cytokines that stimulate the acute phase reaction. The primary role of TNF is in the regulation of immune cells. TNF is able to induce apoptotic cell death, to induce inflammation. Soluble TNF-alpha receptor 1 (sTNFR1) is an extracellular domain of TNFR1 and an antagonist to TNF-alpha (Su et al., 1998. Arthritis Rheum. 41, 139-149). Transgenic expression of sTNFR1 in xenografts may have beneficial anti-inflammatory effects.

Other cytoprotectives with relevant anti-oxidant properties include, without limitation, SOD and Catalyse. Oxygen is the essential molecule for all aerobic organisms, and plays predominant role in ATP generation, namely, oxidative phosphorylation. During this process, reactive oxygen species (ROS) including superoxide anion ($O_2(-)$) and hydrogen peroxide ($H_2O_2$) are produced as by-products. In man, an antioxidant defense system balances the generation of ROS. Superoxide dismutase (SOD) and catalase are two enzymes with anti-oxidant properties. SOD catalyses the dismutation of superoxide radicals to hydrogen peroxide, the latter being converted to water by catalase and glutathione peroxidase. Cellular damage resulting from generation of ROS can occur in a transplant setting. Because of reduced antioxidant defenses, pancreatic beta-cells are especially vulnerable to free radical and inflammatory damage. Commonly used anti-rejection drugs are excellent at inhibiting the adaptive immune response; however, most are harmful to islets and do not protect well from reactive oxygen species and inflammation resulting from islet isolation and ischemia-reperfusion injury. Therefore there is an interest in treating islets ex-vivo with anti-oxidants, or expressing anti-oxidant genes via gene therapy or transgenic expression in donor tissues. Ex vivo gene transfer of EC-SOD and catalase were anti-inflammatory in a rat model of antigen induced arthritis (Dai et al., Gene Ther. 2003 April; 10(7):550-8). In addition, delivery of EC-SOD and/or catalase genes through the portal vein markedly attenuated hepatic I/R injury in a mouse model (He et al., Liver Transpl. 2006 December; 12(12):1869-79). In a recent mouse study, pancreatic islets treated with catalytic antioxidant before syngeneic, suboptimal syngeneic, or xenogeneic transplant exhibited superior function compared with untreated controls. In this same study, diabetic murine recipients of catalytic antioxidant-treated allogeneic islets exhibited improved glycemic control post-transplant and demonstrated a delay in allograft rejection (Sklavos et al., Diabetes. 2010 July; 59(7):1731-8. Epub 2010 Apr. 22). In another mouse study, islet grafts overexpressing MnSOD functioned approximately 50% longer than control grafts (Bertera et al., Diabetes. 2003 February; 52(2):387-93).

Moreover, certain anti-coagulants also provide anti-inflammatory activity including thrombomodulin, EPCR and CD39.

Production of Genetically Modified Animals

Genetically modified animals can be produced by any method known to one of skill in the art including, but not limited to, selective breeding, nuclear transfer, introduction of DNA into oocytes, sperm, zygotes, or blastomeres, or via the use of embryonic stem cells.

In some embodiments, genetic modifications may be identified in animals that are then bred together to form a herd of animals with a desired set of genetic modifications (or a single genetic modification). These progeny may be further bred to produce different or the same set of genetic modifications (or single genetic modification) in their progeny. This cycle of breeding for animals with desired genetic modification(s) may continue for as long as one desires. "Herd" in this context may comprise multiple generations of animals produced over time with the same or different genetic modification(s). "Herd" may also refer to a single generation of animals with the same or different genetic modification(s).

Cells useful for genetic modification (via, for example, but not limited to, homologous recombination) include, by way of example, epithelial cells, neural cells, epidermal cells, keratinocytes, hematopoietic cells, melanocytes, chondrocytes, lymphocytes (B and T lymphocytes), erythrocytes, macrophages, monocytes, mononuclear cells, fibroblasts, cardiac muscle cells, and other muscle cells, etc. Moreover, the cells used for producing the genetically modified animal (via, for example, but not limited to, nuclear transfer) can be obtained from different organs, e.g., skin, lung, pancreas, liver, stomach, intestine, heart, reproductive organs, bladder, kidney, urethra and other urinary organs, etc. Cells can be obtained from any cell or organ of the body, including all somatic or germ cells.

Additionally, animal cells that can be genetically modified can be obtained from a variety of different organs and tissues such as, but not limited to, skin, mesenchyme, lung, pancreas, heart, intestine, stomach, bladder, blood vessels, kidney, urethra, reproductive organs, and a disaggregated preparation of a whole or part of an embryo, fetus, or adult animal. In one embodiment of the invention, cells can be selected from the group consisting of, but not limited to, epithelial cells, fibroblast cells, neural cells, keratinocytes, hematopoietic cells, melanocytes, chondrocytes, lymphocytes (B and T), macrophages, monocytes, mononuclear cells, cardiac muscle cells, other muscle cells, granulosa cells, cumulus cells, epidermal cells, endothelial cells, Islets of Langerhans cells, blood cells, blood precursor cells, bone cells, bone precursor cells, neuronal stem cells, primordial stem cells, adult stem cells, mesenchymal stem cells, hepatocytes, keratinocytes, umbilical vein endothelial cells, aortic endothelial cells, microvascular endothelial cells, fibroblasts, liver stellate cells, aortic smooth muscle cells, cardiac myocytes, neurons, Kupffer cells, smooth muscle cells, Schwann cells, and epithelial cells, erythrocytes, platelets, neutrophils, lymphocytes, monocytes, eosinophils, basophils, adipocytes, chondrocytes, pancreatic islet cells, thyroid cells, parathyroid cells, parotid cells, tumor cells, glial cells, astrocytes, red blood cells, white blood cells, macrophages, epithelial cells, somatic cells, pituitary cells, adrenal cells, hair cells, bladder cells, kidney cells, retinal cells, rod cells, cone cells, heart cells, pacemaker cells, spleen cells, antigen presenting cells, memory cells, T cells, B-cells, plasma cells, muscle cells, ovarian cells, uterine cells, prostate cells, vaginal epithelial cells, sperm cells, testicular cells, germ cells, egg cells, leydig cells, peritubular cells, sertoli cells, lutein cells, cervical cells, endometrial cells, mammary cells, follicle cells, mucous cells, ciliated cells, nonkeratinized epithelial cells, keratinized epithelial cells, lung cells, goblet cells, columnar epithelial cells, squamous epithelial cells, osteocytes, osteoblasts, and osteoclasts. In one alternative embodiment, embryonic stem cells can be used. An embryonic stem cell line can be employed or embryonic stem cells can be obtained freshly from a host, such as a porcine animal. The cells can be grown on an appropriate fibroblast-feeder layer or grown in the presence of leukemia inhibiting factor (LIF).

Embryonic stem cells are a preferred germ cell type, an embryonic stem cell line can be employed or embryonic stem cells can be obtained freshly from a host, such as a porcine animal. The cells can be grown on an appropriate fibroblast-feeder layer or grown in the presence of leukemia inhibiting factor (LIF).

Cells of particular interest include, among other lineages, stem cells, e.g. hematopoietic stem cells, embryonic stem cells, mesenchymal stem cells, etc., the islets of Langerhans, adrenal medulla cells which can secrete dopamine, osteoblasts, osteoclasts, epithelial cells, endothelial cells, leukocytes, e.g. B- and T-lymphocytes, myelomonocytic cells, etc., neurons, glial cells, ganglion cells, retinal cells, liver cells, e.g. hepatocytes, bone marrow cells, keratinocytes, hair follicle cells, and myoblast (muscle) cells.

In a particular embodiment, the cells can be fibroblasts or fibroblast-like cells having a morphology or a phenotype that is not distinguishable from fibroblasts, or a lifespan before senescense of at least 10 or at least 12 or at least 14 or at least 18 or at least 20 days, or a lifespan sufficient to allow homologous recombination and nuclear transfer of a non-senescent nucleus; in one specific embodiment, the cells can be fetal fibroblasts. Fibroblast cells are a suitable somatic cell type because they can be obtained from developing fetuses and adult animals in large quantities. These cells can be easily propagated in vitro with a rapid doubling time and can be clonally propagated for use in gene targeting procedures. The cells to be used can be from a fetal animal, or can be neonatal or from an adult animal in origin. The cells can be mature or immature and either differentiated or non-differentiated.

Homologous Recombination

Homologous recombination permits site-specific modifications in endogenous genes and thus novel alterations can be engineered into the genome. A primary step in homologous recombination is DNA strand exchange, which involves a pairing of a DNA duplex with at least one DNA strand containing a complementary sequence to form an intermediate recombination structure containing heteroduplex DNA (see, for example Radding, C. M. (1982) Ann. Rev. Genet. 16: 405; U.S. Pat. No. 4,888,274). The heteroduplex DNA can take several forms, including a three DNA strand containing triplex form wherein a single complementary strand invades the DNA duplex (Hsieh et al. (1990) Genes and Development 4: 1951; Rao et al., (1991) PNAS 88:2984)) and, when two complementary DNA strands pair with a DNA duplex, a classical Holliday recombination joint or chi structure (Holliday, R. (1964) Genet. Res. 5: 282) can form, or a double-D loop ("Diagnostic Applications of Double-D Loop Formation" U.S. Ser. No. 07/755,462, filed Sep. 4, 1991). Once formed, a heteroduplex structure can be resolved by strand breakage and exchange, so that all or a portion of an invading DNA strand is spliced into a recipient DNA duplex, adding or replacing a segment of the recipient DNA duplex. Alternatively, a heteroduplex structure can result in gene conversion, wherein a sequence of an invading strand is transferred to a recipient DNA duplex by repair of mismatched bases using the invading strand as a template (Genes, 3rd Ed. (1987) Lewin, B., John Wiley, New York, N.Y.; Lopez et al. (1987) Nucleic Acids Res. 15: 5643). Whether by the mechanism of breakage and rejoining or by the mechanism(s) of gene conversion, formation of heteroduplex DNA at homologously paired joints can serve to transfer genetic sequence information from one DNA molecule to another.

The ability of homologous recombination (gene conversion and classical strand breakage/rejoining) to transfer genetic sequence information between DNA molecules renders targeted homologous recombination a powerful method in genetic engineering and gene manipulation.

In homologous recombination, the incoming DNA interacts with and integrates into a site in the genome that contains a substantially homologous DNA sequence. In non-homologous ("random" or "illicit") integration, the incoming DNA is not found at a homologous sequence in the genome but integrates elsewhere, at one of a large number of potential locations. In general, studies with higher eukaryotic cells have revealed that the frequency of homologous recombination is far less than the frequency of random integration. The ratio of these frequencies has direct implications for "gene targeting" which depends on integration via homologous recombination (i.e. recombination between the exogenous "targeting DNA" and the corresponding "target DNA" in the genome). The present invention can use homologous recombination to inactivate a gene or insert and upregulate or activate a gene in cells, such as the cells described above. The DNA can comprise at least a portion of the gene(s) at the particular locus with introduction of an alteration into at least one, optionally both copies, of the native gene(s), so as to prevent expression of functional gene product. The alteration can be an insertion, deletion, replacement, mutation or combination thereof. When the alteration is introduced into only one copy of the gene being inactivated, the cells having a single unmutated copy of the target gene are amplified and can be subjected to a second targeting step, where the alteration can be the same or different from the first alteration, usually different, and where a deletion, or replacement is involved, can be overlapping at least a portion of the alteration originally introduced. In this second targeting step, a targeting vector with the same arms of homology, but containing a different mammalian selectable markers can be used. The resulting transformants are screened for the absence of a functional target antigen and the DNA of the cell can be further screened to ensure the absence of a wild-type target gene. Alternatively, homozygosity as to a phenotype can be achieved by breeding hosts heterozygous for the mutation.

A number of papers describe the use of homologous recombination in mammalian cells. Illustrative of these papers are Kucherlapati et al. (1984) Proc. Natl. Acad. Sci. USA 81:3153-3157; Kucherlapati et al. (1985) Mol. Cell. Bio. 5:714-720; Smithies et al. (1985) Nature 317:230-234; Wake et al. (1985) Mol. Cell. Bio. 8:2080-2089; Ayares et al. (1985) Genetics 111:375-388; Ayares et al. (1986) Mol. Cell. Bio. 7:1656-1662; Song et al. (1987) Proc. Natl. Acad. Sci. USA 84:6820-6824; Thomas et al. (1986) Cell 44:419-428; Thomas and Capecchi, (1987) Cell 51: 503-512; Nandi et al. (1988) Proc. Natl. Acad. Sci. USA 85:3845-3849; and Mansour et al. (1988) Nature 336:348-352; Evans and Kaufman, (1981) Nature 294:146-154; Doetschman et al. (1987) Nature 330:576-578; Thoma and Capecchi, (1987) Cell 51:503-512; Thompson et al. (1989) Cell 56:316-321.

Random Insertion

In one embodiment, the DNA encoding the transgene sequences can be randomly inserted into the chromosome of a cell. The random integration can result from any method of introducing DNA into the cell known to one of skill in the art. This may include, but is not limited to, electroporation, sonoporation, use of a gene gun, lipotransfection, calcium phosphate transfection, use of dendrimers, microinjection, the use of viral vectors including adenoviral, AAV, and retroviral vectors, and group II ribozymes. In one embodiment, the DNA encoding the can be designed to include a reporter gene so that the presence of the transgene or its expression product can be detected via the activation of the reporter gene. Any reporter gene known in the art can be used, such as those disclosed above. By selecting in cell culture those cells in which the reporter gene has been activated, cells can be selected that contain the transgene. In other embodiments, the DNA encoding the transgene can be introduced into a cell via electroporation. In other embodiments, the DNA can be introduced into a cell via lipofection, infection, or transformation. In one embodiment, the electroporation and/or lipofection can be used to transfect fibroblast cells. In a particular embodiment, the transfected fibroblast cells can be used as nuclear donors for nuclear transfer to generate transgenic animals as known in the art and described below.

Cells that have been stained for the presence of a reporter gene can then be sorted by FACS to enrich the cell population such that we have a higher percentage of cells that contain the DNA encoding the transgene of interest. In other embodiments, the FACS-sorted cells can then be cultured for a periods of time, such as 12, 24, 36, 48, 72, 96 or more hours or for such a time period to allow the DNA to integrate to yield a stable transfected cell population.

Vectors for Producing Transgenic Animals

Nucleic acid targeting vector constructs can be designed to accomplish homologous recombination in cells. In one embodiment, a targeting vector is designed using a "poly(A) trap". Unlike a promoter trap, a poly(A) trap vector captures a broader spectrum of genes including those not expressed in the target cell (i.e fibroblasts or ES cells). A polyA trap vector includes a constitutive promoter that drives expression of a selectable marker gene lacking a polyA signal. Replacing the polyA signal is a splice donor site designed to splice into downstream exons. In this strategy, the mRNA of the selectable marker gene can be stabilized upon trapping of a polyA signal of an endogenous gene regardless of its expression status in the target cells. In one embodiment, a targeting vector is constructed including a selectable marker that is deficient of signals for polyadenylation.

These targeting vectors can be introduced into mammalian cells by any suitable method including, but not limited to, transfection, transformation, virus-mediated transduction, or infection with a viral vector. In one embodiment, the targeting vectors can contain a 3' recombination arm and a 5' recombination arm (i.e. flanking sequence) that is homologous to the genomic sequence of interest. The 3' and 5' recombination arms can be designed such that they flank the 3' and 5' ends of at least one functional region of the genomic sequence. The targeting of a functional region can render it inactive, which results in the inability of the cell to produce functional protein. In another embodiment, the homologous DNA sequence can include one or more intron and/or exon sequences. In addition to the nucleic acid sequences, the expression vector can contain selectable marker sequences, such as, for example, enhanced Green Fluorescent Protein (eGFP) gene sequences, initiation and/or enhancer sequences, poly A-tail sequences, and/or nucleic acid sequences that provide for the expression of the construct in prokaryotic and/or eukaryotic host cells. The selectable marker can be located between the 5' and 3' recombination arm sequence.

Modification of a targeted locus of a cell can be produced by introducing DNA into the cells, where the DNA has homology to the target locus and includes a marker gene, allowing for selection of cells comprising the integrated construct. The homologous DNA in the target vector will recombine with the chromosomal DNA at the target locus. The marker gene can be flanked on both sides by homologous DNA sequences, a 3' recombination arm and a 5' recombination arm. Methods for the construction of targeting vectors have been described in the art, see, for example, Dai et al., Nature Biotechnology 20: 251-255, 2002; WO 00/51424.

A variety of enzymes can catalyze the insertion of foreign DNA into a host genome. Viral integrases, transposases and site-specific recombinases mediate the integration of virus genomes, transposons or bacteriophages into host genomes. An extensive collection of enzymes with these properties can be derived from a wide variety of sources. Retroviruses combine several useful features, including the relative simplicity of their genomes, ease of use and their ability to integrate into the host cell genome, permitting long-term transgene expression in the transduced cells or their progeny. They have, therefore, been used in a large number of gene-therapy protocols. Vectors based on Lentivirus vectors, have been attractive candidates for both gene therapy and transgenic applications as have sdeno-associated virus, which is a small DNA virus (parvovirus) that is co-replicated in mammalian cells together with helper viruses such as adenovirus, herpes simplex virus or human cytomegalovirus. The viral genome essentially consists of only two ORFs (rep, a non-structural protein, and cap, a structural protein) from which (at least) seven different polypeptides are derived by alternative splicing and alternative promoter usage. In the presence of a helper-virus, the rep proteins mediate replication of the AAV genome. Integration, and thus a latent virus infection, occurs in the absence of helper virus. Transposons are also of interest. These are segments of mobile DNA that can be found in a variety of organisms. Although active transposons are found in many prokaryotic systems and insects, no functional natural transposons exist in vertebrates. The *Drosophila* P element transposon has been used for many years as a genome engineering tool. The sleeping beauty transposon was established from nonfunctional transposon copies found in salmonid fish and is significantly more active in mammalian cells than prokaryotic or insect transposons. Site-specific recombinases are enzymes that catalyze DNA strand exchange between DNA segments that possess only a limited degree of sequence homology. They bind to recognition sequences that are between 30 and 200 nucleotides in length, cleave the DNA backbone, exchange the two DNA double helices involved and religate the DNA. In some site-specific recombination systems, a single polypeptide is sufficient to perform all of these reactions, whereas other recombinases require a varying number of accessory proteins to fulfill these tasks. Site-specific recombinases can be clustered into two protein families with distinct biochemical properties, namely tyrosine recombinases (in which the DNA is covalently attached to a tyrosine residue) and serine recombinases (where covalent attachment occurs at a serine residue). The most popular enzymes used for genome modification approaches are Cre (a tyrosine recombinase derived from *E. coli* bacteriophage P1) and fC31 integrase (a serine recombinase derived from the *Streptomyces* phage fC31). Several other bacteriophage derived site-specific recombinases (including Flp, lambda integrase, bacteriophage HK022 recombinase, bacteriophage R4 integrase and phage TP901-1 integrase) have been used successfully to mediate stable gene insertions into mammalian genomes. Recently, a site-specific recombinase has been purified from the *Streptomyces* bacteriophage. The fC31 recombinase is a member of the resolvase family and mediates phage integration. In this process the bacteriophage attP site recombines with the corresponding attB site in the bacterial genome. The crossover generates two sites, attL and attR, which are no longer a target for recombinase action, in the absence of accessory proteins. The reaction also takes place in mammalian cells and can therefore be used to mediate site-specific integration of therapeutic genes. The site-specificity of tyrosine-recombinases has been difficult to modify by direct protein engineering because the catalytic domain and the DNA recognition domain are closely interwoven. Therefore, changes in specificity are often accompanied by a loss in activity. Serine recombinases might be more amenable to engineering and a hyperactive derivative of Tn3 resolvase has been modified by exchange of the natural DBD for a zinc-finger domain of the human zinc-finger transcription factor Zif268. The DNA site-specificity of the resulting chimeric protein, termed Z-resolvase, had been switched to that of Zif268. Zinc-finger proteins can be modified by in vitro protein evolution to recognize any DNA sequence, therefore, this approach could enable development of chimeric recombinases that can integrate therapeutic genes into precise genomic locations. Methods for enhancing or mediating recombination include the combination of site-specific recombination and homologous recombination, AAV-vector mediated, and zinc-finger nuclease mediated recombination (ref: Geurts et. al., Science, 325: 433, 2009)

The term "vector," as used herein, refers to a nucleic acid molecule (preferably DNA) that provides a useful biological or biochemical property to an inserted nucleic acid. "Expression vectors" according to the invention include vectors that are capable of enhancing the expression of one or more molecules that have been inserted or cloned into the vector, upon transformation of the vector into a cell. Examples of such expression vectors include, phages, autonomously replicating sequences (ARS), centromeres, and other sequences which are able to replicate or be replicated in vitro or in a cell, or to convey a desired nucleic acid segment to a desired location within a cell of an animal. Expression vectors useful in the present invention include chromosomal-, episomal- and virus-derived vectors, e.g., vectors derived from bacterial plasmids or bacteriophages, and vectors derived from combinations thereof, such as cosmids and phagemids or virus-based vectors such as adenovirus, AAV, lentiviruses. A vector can have one or more restriction endonuclease recognition sites at which the sequences can be cut in a determinable fashion without loss of an essential biological function of the vector, and into which a nucleic acid fragment can be spliced in order to bring about its replication and cloning. Vectors can further provide primer sites, e.g., for PCR, transcriptional and/or translational initiation and/or regulation sites, recombinational signals, replicons, selectable markers, etc. Clearly, methods of inserting a desired nucleic acid fragment which do not require the use of homologous recombination, transpositions or restriction enzymes (such as, but not limited to, UDG cloning of PCR fragments (U.S. Pat. No. 5,334,575), TA Cloning® brand PCR cloning (Invitrogen Corp., Carlsbad, Calif.)) can also be applied to clone a nucleic acid into a vector to be used according to the present invention.

Cells homozygous at a targeted locus can be produced by introducing DNA into the cells, where the DNA has homology to the target locus and includes a marker gene, allowing for selection of cells comprising the integrated construct. The homologous DNA in the target vector will recombine with the chromosomal DNA at the target locus. The marker gene can be flanked on both sides by homologous DNA sequences, a 3' recombination arm and a 5' recombination arm. Methods for the construction of targeting vectors have been described in the art, see, for example, Dai et al. (2002) Nature Biotechnology 20: 251-255; WO 00/51424, FIG. 6; and Gene Targeting: A Practical Approach. Joyner, A. Oxford University Press, USA; $2^{nd}$ ed. Feb. 15, 2000.

Various constructs can be prepared for homologous recombination at a target locus. Usually, the construct can include at least 25 bp, 50 bp, 100 bp, 500 bp, 1 kbp, 2 kbp, 4 kbp, 5 kbp, 10 kbp, 15 kbp, 20 kbp, or 50 kbp of sequence homologous with the target locus.

Various considerations can be involved in determining the extent of homology of target DNA sequences, such as, for example, the size of the target locus, availability of sequences, relative efficiency of double cross-over events at the target locus and the similarity of the target sequence with other sequences. The targeting DNA can include a sequence in which DNA substantially isogenic flanks the desired sequence modifications with a corresponding target sequence in the genome to be modified. The substantially isogenic sequence can be at least about 95%, 97-98%, 99.0-99.5%, 99.6-99.9%, or 100% identical to the corresponding target sequence (except for the desired sequence modifications). The targeting DNA and the target DNA preferably can share stretches of DNA at least about 75, 150 or 500 base pairs that are 100% identical. Accordingly, targeting DNA can be derived from cells closely related to the cell line being targeted; or the targeting DNA can be derived from cells of the same cell line or animal as the cells being targeted.

Suitable selectable marker genes include, but are not limited to: genes conferring the ability to grow on certain media substrates, such as the tk gene (thymidine kinase) or the hprt gene (hypoxanthine phosphoribosyltransferase) which confer the ability to grow on HAT medium (hypoxanthine, aminopterin and thymidine); the bacterial gpt gene (guanine/xanthine phosphoribosyltransferase) which allows growth on MAX medium (mycophenolic acid, adenine, and xanthine).

See Song et al. (1987) Proc. Nat'l Acad. Sci. U.S.A. 84:6820-6824. See also Sambrook et al. (1989) Molecular Cloning—A Laboratory Manual, Cold Spring Harbor Laboratory, Cold Spring Harbor, N.Y., see chapter 16. Other examples of selectable markers include: genes conferring resistance to compounds such as antibiotics, genes conferring the ability to grow on selected substrates, genes encoding proteins that produce detectable signals such as luminescence, such as green fluorescent protein, enhanced green fluorescent protein (eGFP). A wide variety of such markers are known and available, including, for example, antibiotic resistance genes such as the neomycin resistance gene (neo) (Southern, P., and P. Berg, (1982) J. Mol. Appl. Genet. 1:327-341); and the hygromycin resistance gene (hyg) (Nucleic Acids Research 11:6895-6911 (1983), and Te Riele et al. (1990) Nature 348: 649-651). Additional reporter genes useful in the methods of the present invention include acetohydroxyacid synthase (AHAS), alkaline phosphatase (AP), beta galactosidase (LacZ), beta glucoronidase (GUS), chloramphenicol acetyltransferase (CAT), green fluorescent protein (GFP), red fluorescent protein (RFP), yellow fluorescent protein (YFP), cyan fluorescent protein (CFP), horseradish peroxidase (HRP), luciferase (Luc), nopaline synthase (NOS), octopine synthase (OCS), and derivatives thereof. Multiple selectable markers are available that confer resistance to ampicillin, bleomycin, chloramphenicol, gentamycin, hygromycin, kanamycin, lincomycin, blasticidin, zeocin, methotrexate, phosphinothricin, puromycin, and tetracycline. Methods to determine suppression of a reporter gene are well known in the art, and include, but are not limited to, fluorometric methods (e.g. fluorescence spectroscopy, Fluorescence Activated Cell Sorting (FACS), fluorescence microscopy), antibiotic resistance determination.

Combinations of selectable markers can also be used. To use a combination of markers, the HSV-tk gene can be cloned such that it is outside of the targeting DNA (another selectable marker could be placed on the opposite flank, if desired). After introducing the DNA construct into the cells to be targeted, the cells can be selected on the appropriate antibiotics. Selectable markers can also be used for negative selection. Negative selection markets generally kill the cells in which they are expressed either because the expression is per se toxic or produces a catalyst that leads to toxic metabolite, such as Herpes simplex virus Type I thymidine kinase (HSV-tk) or diphtheria toxin A. Generally, the negative selection marker is incorporated into the targeting vector so that it is lost following a precise recombination event. Similarly, conventional selectable markers such as GFP can be used for negative selection using, for example, FACS sorting.

Deletions can be at least about 50 bp, more usually at least about 100 bp, and generally not more than about 20 kbp, where the deletion can normally include at least a portion of the coding region including a portion of or one or more exons, a portion of or one or more introns, and can or can not include a portion of the flanking non-coding regions, particularly the 5-non-coding region (transcriptional regulatory region). Thus, the homologous region can extend beyond the coding region into the 5'-non-coding region or alternatively into the 3-non-coding region. Insertions can generally not exceed 10 kbp, usually not exceed 5 kbp, generally being at least 50 bp, more usually at least 200 bp.

The region(s) of homology can include mutations, where mutations can further inactivate the target gene, in providing for a frame shift, or changing a key amino acid, or the mutation can correct a dysfunctional allele, etc. Usually, the mutation can be a subtle change, not exceeding about 5% of the homologous flanking sequences or even a single nucleotide change such as a point mutation in an active site of an exon. Where mutation of a gene is desired, the marker gene can be inserted into an intron, so as to be excised from the target gene upon transcription.

Various considerations can be involved in determining the extent of homology of target DNA sequences, such as, for example, the size of the target locus, availability of sequences, relative efficiency of double cross-over events at the target locus and the similarity of the target sequence with other sequences. The targeting DNA can include a sequence in which DNA substantially isogenic flanks the desired sequence modifications with a corresponding target sequence in the genome to be modified. The substantially isogenic sequence can be at least about 95%, or at least about 97% or at least about 98% or at least about 99% or between 95 and 100%, 97-98%, 99.0-99.5%, 99.6-99.9%, or 100% identical to the corresponding target sequence (except for the desired sequence modifications). In a particular embodiment, the targeting DNA and the target DNA can share stretches of DNA at least about 75, 150 or 500 base pairs that are 100% identical. Accordingly, targeting DNA can be derived from cells closely related to the cell line being targeted; or the targeting DNA can be derived from cells of the same cell line or animal as the cells being targeted.

The construct can be prepared in accordance with methods known in the art, various fragments can be brought together, introduced into appropriate vectors, cloned, analyzed and then manipulated further until the desired construct has been achieved. Various modifications can be made to the sequence, to allow for restriction analysis, excision, identification of probes, etc. Silent mutations can be introduced, as desired. At various stages, restriction analysis, sequencing, amplification with the polymerase chain reaction, primer repair, in vitro mutagenesis, etc. can be employed.

The construct can be prepared using a bacterial vector, including a prokaryotic replication system, e.g. an origin recognizable by E. coli, at each stage the construct can be cloned and analyzed. A marker, the same as or different from the marker to be used for insertion, can be employed, which can be removed prior to introduction into the target cell. Once the vector containing the construct has been completed, it can be further manipulated, such as by deletion of the bacterial sequences, linearization, introducing a short deletion in the homologous sequence. After final manipulation, the construct can be introduced into the cell.

Techniques which can be used to allow the DNA or RNA construct entry into the host cell include calcium phosphate/DNA coprecipitation, microinjection of DNA into the nucleus, electroporation, bacterial protoplast fusion with intact cells, transfection, lipofection, infection, particle bombardment, sperm mediated gene transfer, or any other technique known by one skilled in the art. The DNA or RNA can be single or double stranded, linear or circular, relaxed or supercoiled DNA. For various techniques for transfecting mammalian cells, see, for example, Keown et al., Methods in Enzymology Vol. 185, pp. 527-537 (1990).

The following vectors are provided by way of example. Bacterial: pBs, pQE-9 (Qiagen), phagescript, PsiX174, pBluescript SK, pBsKS, pNH8a, pNH16a, pNH18a, pNH46a (Stratagene); pTrc99A, pKK223-3, pKK233-3, pDR54O, pRIT5 (Pharmacia). Eukaryotic: pWLneo, pSv2cat, pOG44, pXT1, pSG (Stratagene) pSVK3, pBPv, pMSG, pSVL (Pharmiacia). Also, any other plasmids and vectors can be used as long as they are replicable and viable in the host. Vectors known in the art and those commercially available (and variants or derivatives thereof) can in accordance with the invention be engineered to include one or more recombination sites for use in the methods of the invention. Such vectors can be obtained from, for example, Vector Laboratories Inc., Invitrogen, Promega, Novagen, NEB, Clontech, Boehringer Mannheim, Pharmacia, EpiCenter, OriGenes Technologies Inc., Stratagene, PerkinElmer, Pharmingen, and Research Genetics. Other vectors of interest include eukaryotic expression vectors such as pFastBac, pFastBacHT, pFastBacDUAL, pSFV, and pTet-Splice (Invitrogen), pEUK-C1, pPUR, pMAM, pMAMneo, pBI101, pBI121, pDR2, pCMVEBNA, and pYACneo (Clontech), pSVK3, pSVL, pMSG, pCH110, and pKK232-8 (Pharmacia, Inc.), p3'SS, pXT1, pSG5, pPbac, pMbac, pMC1neo, and pOG44 (Stratagene, Inc.), and pYES2, pAC360, pBlueBacHis A, B, and C, pVL1392, pBlueBacIII, pCDM8, pcDNA1, pZeoSV, pcDNA3 pREP4, pCEP4, and pEBVHis (Invitrogen, Corp.) and variants or derivatives thereof.

Other vectors include pUC18, pUC19, pBlueScript, pSPORT, cosmids, phagemids, YAC's (yeast artificial chromosomes), BAC's (bacterial artificial chromosomes), P1 (*Escherichia coli* phage), pQE70, pQE60, pQE9 (quagan), pBS vectors, PhageScript vectors, BlueScript vectors, pNH8A, pNH16A, pNH18A, pNH46A (Stratagene), pcDNA3 (Invitrogen), pGEX, pTrsfus, pTrc99A, pET-5, pET-9, pKK223-3, pKK233-3, pDR540, pRIT5 (Pharmacia), pSPORT1, pSPORT2, pCMVSPORT2.0 and pSY—SPORT1 (Invitrogen) and variants or derivatives thereof. Viral vectors can also be used, such as lentiviral vectors (see, for example, WO 03/059923; Tiscornia et al. PNAS 100:1844-1848 (2003)).

Additional vectors of interest include pTrxFus, pThioHis, pLEX, pTrcHis, pTrcHis2, pRSET, pBlueBacHis2, pcDNA3.1/His, pcDNA3.1(−)/Myc-His, pSecTag, pEBVHis, pPIC9K, pPIC3.5K, pAO81S, pPICZ, pPICZA, pPICZB, pPICZC, pGAPZA, pGAPZB, pGAPZC, pBlueBac4.5, pBlueBacHis2, pMelBac, pSinRep5, pSinHis, pIND, pIND(SP1), pVgRXR, pcDNA2.1, pYES2, pZErO1.1, pZErO-2.1, pCR-Blunt, pSE280, pSE380, pSE420, pVL1392, pVL1393, pCDM8, pcDNA1.1, pcDNA1.1/Amp, pcDNA3.1, pcDNA3.1/Zeo, pSe, SV2, pRc/CMV2, pRc/RSV, pREP4, pREP7, pREP8, pREP9, pREP 10, pCEP4, pEBVHis, pCR3.1, pCR2.1, pCR3.1-Uni, and pCRBac from Invitrogen; λ ExCell, λ gt11, pTrc99A, pKK223-3, pGEX-1λ T, pGEX-2T, pGEX-2TK, pGEX-4T-1, pGEX-4T-2, pGEX-4T-3, pGEX-3X, pGEX-5X-1, pGEX-5X-2, pGEX-5X-3, pEZZ18, pRIT2T, pMC1871, pSVK3, pSVL, pMSG, pCH110, pKK232-8, pSL1180, pNEO, and pUC4K from Pharmacia; pSCREEN-1b(+), pT7Blue(R), pT7Blue-2, pCITE-4-abc(+), pOCUS-2, pTAg, pET-32L1C, pET-30LIC, pBAC-2 cp LIC, pBACgus-2 cp LIC, pT7Blue-2 LIC, pT7Blue-2, λ SCREEN-1, λ BlueSTAR, pET-3abcd, pET-7abc, pET9abcd, pET11 abcd, pET12abc, pET-14b, pET-15b, pET-16b, pET-17b-pET-17xb, pET-19b, pET-20b(+), pET-21abcd(+), pET-22b(+), pET-23abcd(+), pET-24abcd (+), pET-25b(+), pET-26b(+), pET-27b(+), pET-28abc(+), pET-29abc(+), pET-30abc(+), pET-31b(+), pET-32abc(+), pET-33b(+), pBAC-1, pBACgus-1, pBAC4x-1, pBACgus4x-1, pBAC-3 cp, pBACgus-2 cp, pBACsurf-1, plg, Signal plg, pYX, Selecta Vecta-Neo, Selecta Vecta-Hyg, and Selecta Vecta-Gpt from Novagen; pLexA, pB42AD, pGBT9, pAS2-1, pGAD424, pACT2, pGAD GL, pGAD GH, pGAD10, pGilda, pEZM3, pEGFP, pEGFP-1, pEGFP-N, pEGFP-C, pEBFP, pGFPuv, pGFP, p6xHis-GFP, pSEAP2-Basic, pSEAP2-Contral, pSEAP2-Promoter, pSEAP2-Enhancer, pβgal-Basic, pβgal-Control, pβgal-Promoter, pβgal-Enhancer, pCMV, pTet-Off, pTet-On, pTK-Hyg, pRetro-Off, pRetro-On, pIRES1neo, pIRES1hyg, pLXSN, pLNCX, pLAPSN, pMAMneo, pMAMneo-CAT, pMAMneo-LUC, pPUR, pSV2neo, pYEX4T-1/2/3, pYEX-S1, pBacPAK-His, pBacPAK8/9, pAcUW31, BacPAK6, pTrip1Ex, 2λgt10, λgt11, pWE15, and λ Trip1Ex from Clontech; Lambda ZAP II, pBK-CMV, pBK-RSV, pBluescript II KS+/−, pBluescript II SK+/−, pAD-GAL4, pBD-GAL4 Cam, pSurfscript, Lambda FIX II, Lambda DASH, Lambda EMBL3, Lambda EMBL4, SuperCos, pCR-Scrigt Amp, pCR-Script Cam, pCR-Script Direct, pBS+/−, pBC KS+/−, pBC SK+/−, Phagescript, pCAL-n-EK, pCAL-n, pCAL-c, pCAL-kc, pET-3abcd, pET-11abcd, pSPUTK, pESP-1, pCMVLacI, pOPRSVI/MCS, pOPI3 CAT, pXT1, pSG5, pPbac, pMbac, pMC1neo, pMC1neo Poly A, pOG44, pOG45, pFRTβGAL, pNEOβGAL, pRS403, pRS404, pRS405, pRS406, pRS413, pRS414, pRS415, and pRS416 from Stratagene.

Additional vectors include, for example, pPC86, pDBLeu, pDBTrp, pPC97, p2.5, pGAD1-3, pGAD10, pACt, pACT2, pGADGL, pGADGH, pAS2-1, pGAD424, pGBT8, pGBT9, pGAD-GAL4, pLexA, pBD-GAL4, pHISi, pHISi-1, placZi, pB42AD, pDG202, pJK202, pJG4-5, pNLexA, pYESTrp and variants or derivatives thereof.

Promoters

Vector constructs used to produce the animals of the invention can include regulatory sequences, including, for example, a promoter, operably linked to the sequence. Large numbers of suitable vectors and promoters are known to those of skill in the art, and are commercially available.

In specific embodiments, the present invention provides animals, tissues and cells that express a transgene, and in particular an immunomodulator or anticoagulant transgene, in pancreatic tissue. To target expression to a particular tissue, the animal is developed using a vector that includes a promoter specific for pancreatic gene expression.

In one embodiment, the nucleic acid construct contains a regulatory sequence operably linked to the transgene sequence to be expressed. In one embodiment, the regulatory sequence can be a promoter sequence. In one embodiment, the promoter can be a regulateable promoter. In such systems, drugs, for example, can be used to regulate whether the peptide is expressed in the animal, tissue or organ. For example, expression can be prevented while the organ or tissue is part of the pig, but expression induced once the pig has been transplanted to the human for a period of time to overcome the cellular immune response. In addition, the level of expression can be controlled by a regulateable promoter system to ensure that immunosuppression of the recipient's immune system does not occur. The regulateable promoter system can be selected from, but not limited to, the following gene systems: a metallothionein promoter, inducible by metals such as copper (see Lichtlen and Schaffner, Swiss Med. Wkly., 2001, 131 (45-46):647-52); a tetracycline-regulated system (see Imhof et al., J Gene Med., 2000, 2(2):107-16); an ecdysone-regulated system (see Saez et al., Proc Natl Acad Sci USA., 2000, 97(26):14512-7); a cytochrome P450 inducible promoter, such as the CYP1A1 promoter (see Fujii-Kuriyama et al., FASEB J., 1992, 6(2):706-10); a mifepristone inducible system (see Sirin and Park, Gene., 2003, 323:67-77); a coumarin-activated system (see Zhao et al., Hum Gene Ther., 2003, 14(17): 1619-29); a macrolide inducible system (responsive to macrolide antibiotics such as rapamycin, erythromycin, clarithromycin, and roxitiromycin) (see Weber et al., Nat Biotechnol., 2002, 20(9):901-7; Wang et al., Mol Ther., 2003, 7(6):790-800); an ethanol induced system (see Garoosi et al., J Exp Bot., 2005, 56(416):163542; Roberts et al., Plant Physiol., 2005, 138(3):1259-67); a streptogramin inducible system (see Fussenegger et al., Nat Biotechnol., 2000 18(11):1203-8) an electrophile inducible system (see Zhu and Fahl, Biochem Biophys Res Commun., 2001, 289

(1):212-9); and a nicotine inducible system (see Malphettes et al., Nucleic Acids Res., 2005, 33(12):e107).

In particular embodiments, the promoter is a tissue specific promoter, in particular in expression of an anticoagulant or immunosuppressant. The tissue specific promoter is most preferably a pancreas-specific promoters (Edlund et al., Science, 1985, 230:912-916). In one embodiment, the tissue-specific promoter is ins2 (Lomedico P et al., Cell, 1979, 18:545; GenBank J00747 and J00748.

In other embodiments an enhancer element is used in the nucleic acid construct to facilitate increased expression of the transgene in a tissue-specific manner. Enhancers are outside elements that drastically alter the efficiency of gene transcription (Molecular Biology of the Gene, Fourth Edition, pp. 708-710, Benjamin Cummings Publishing Company, Menlo Park, Calif. ©1987). In a particular embodiment, the pdx-1 enhancer (also known as IPF-1, STF-1, and IDX1 (Gerrish K et al., Mol. Endocrinol., 2004, 18(3): 533; Ohlsson et al., EMBO J. 1993 November, 12(11):4251-9; Leonard et al., Mol. Endocrinol., 1993, 7(10):1275-83; Miller et al., EMBO J., 1994, 13(5):1145-56; Serup et al., Proc Natl Acad Sci USA., 1996, 93(17):9015-20; Melloul et al., Diabetes., 2002, 51 Suppl 3:S320-5; Glick et al., J Biol Chem., 2000, 275(3): 2199-204; GenBank AF334615.)) is used in combination with the ins2 promoter, for pancreas specific expression of the transgene(s). In certain embodiments, the animal expresses a transgene under the control of a promoter in combination with an enhancer element. In particular embodiments, the animal includes a pancreas specific promoter element, such as an insulin promoter, and further includes an enhancer element. In some embodiments, the enhancer element is PDX1. In specific embodiments, the animal, tissue or cell includes the RIP promoter in combination with a PDX1 enhancer. In other embodiments, the promoter can be a ubiquitous promoter. Ubiquitous promoters include, but are not limited to the following: viral promoters like CMV, SV40. Suitable promoters also include beta-Actin promoter, gamma-actin promoter, GAPDH promoters, $H_2K$, ubiquitin and the *rosa* promoter.

Selection of Transgenic Cells

In some cases, the transgenic cells have genetic modifications that are the result of targeted transgene insertion or integration (i.e. via homologous recombination) into the cellular genome. In some cases, the transgenic cells have genetic modification that are the result of non-targeted (random) integration into the cellular genome. The cells can be grown in appropriately-selected medium to identify cells providing the appropriate integration. Those cells which show the desired phenotype can then be further analyzed by restriction analysis, electrophoresis, Southern analysis, polymerase chain reaction, or another technique known in the art. By identifying fragments which show the appropriate insertion at the target gene site, (or, in non-targeted applications, where random integration techniques have produced the desired result) cells can be identified in which homologous recombination (or desired non-targeted integration events) has occurred to inactivate or otherwise modify the target gene.

The presence of the selectable marker gene establishes the integration of the target construct into the host genome. Those cells which show the desired phenotype can then be further analyzed by restriction analysis, electrophoresis, Southern analysis, polymerase chain reaction, etc to analyze the DNA in order to establish whether homologous or non-homologous recombination occurred. This can be determined by employing probes for the insert and then sequencing the 5' and 3' regions flanking the insert for the presence of the gene extending beyond the flanking regions of the construct or identifying the presence of a deletion, when such deletion is introduced. Primers can also be used which are complementary to a sequence within the construct and complementary to a sequence outside the construct and at the target locus. In this way, one can only obtain DNA duplexes having both of the primers present in the complementary chains if homologous recombination has occurred. For example, by demonstrating the presence of the primer sequences or the expected size sequence, the occurrence of homologous recombination is supported.

The polymerase chain reaction used for screening homologous recombination events is described in Kim and Smithies, (1988) Nucleic Acids Res. 16:8887-8903; and Joyner et al. (1989) Nature 338:153-156.

The cell lines obtained from the first round of targeting (or from non-targeted (random) integration into the genome) are likely to be heterozygous for the integrated allele. Homozygosity, in which both alleles are modified, can be achieved in a number of ways. One approach is to grow up a number of cells in which one copy has been modified and then to subject these cells to another round of targeting (or non-targeted (random) integration) using a different selectable marker. Alternatively, homozygotes can be obtained by breeding animals heterozygous for the modified allele. In some situations, it can be desirable to have two different modified alleles. This can be achieved by successive rounds of gene targeting (or random integration) or by breeding heterozygotes, each of which carries one of the desired modified alleles. In certain embodiments, at least one element of the animal is derived by selection of a spontaneously occurring mutation in an allele, in particular to develop a homozygous animal. In certain embodiments, a selection technique is used to obtain homologous knockout cells from heterozygous cells by exposure to very high levels of a selection agent. Such a selection can be, for example, by use of an antibiotic such as geneticin (G418).

Cells that have been transfected or otherwise received an appropriate vector can then be selected or identified via genotype or phenotype analysis. In one embodiment, cells are transfected, grown in appropriately-selected medium to identify cells containing the integrated vector. The presence of the selectable marker gene indicates the presence of the transgene construct in the transfected cells. Those cells which show the desired phenotype can then be further analyzed by restriction analysis, electrophoresis, Southern analysis, polymerase chain reaction, etc to analyze the DNA in order to verify integration of transgene(s) into the genome of the host cells. Primers can also be used which are complementary to transgene sequence(s). The polymerase chain reaction used for screening homologous recombination and random integration events is known in the art, see, for example, Kim and Smithies, Nucleic Acids Res. 16:8887-8903, 1988; and Joyner et al., Nature 338:153-156, 1989. The specific combination of a mutant polyoma enhancer and a thymidine kinase promoter to drive the neomycin gene has been shown to be active in both embryonic stem cells and EC cells by Thomas and Capecchi, supra, 1987; Nicholas and Berg (1983) in Teratocarcinoma Stem Cell, eds. Siver, Martin and Strikland (Cold Spring Harbor Lab., Cold Spring Harbor, N.Y. (pp. 469-497); and Linney and Donerly, Cell 35:693-699, 1983.

Cells that have undergone homologous recombination can be identified by a number of methods. In one embodiment, the selection method can detect the absence of an immune response against the cell, for example by a human anti-gal antibody. In other embodiments, the selection method can include assessing the level of clotting in human blood when exposed to a cell or tissue. Selection via antibiotic resistance has been used most commonly for screening. This method can detect the presence of the resistance gene on the targeting vector, but does not directly indicate whether integration was a targeted recombination event or a random integration. Alternatively, the marker can be a fluorescent marker gene such as GFP or RFP, or a gene that is detectable on the cell surface via cell sorting or FACs analysis. Certain technology, such as Poly A and promoter trap technology, increase the probability of targeted events, but again, do not give direct evidence that the desired phenotype has been achieved. In addition, negative forms of selection can be used to select for targeted integration; in these cases, the gene for a factor lethal to the cells (e.g. Tk or diptheria A toxin) is inserted in such a way that only targeted events allow the cell to avoid death. Cells selected by these methods can then be assayed for gene disruption, vector integration and, finally, gene depletion. In these cases, since the selection is based on detection of targeting vector integration and not at the altered phenotype, only targeted knockouts, not point mutations, gene rearrangements or truncations or other such modifications can be detected.

Characterization can be further accomplished by the following techniques, including, but not limited to: PCR analysis, Southern blot analysis, Northern blot analysis, specific lectin binding assays, and/or sequencing analysis. Phenotypic characterization can also be accomplished, including by binding of anti-mouse antibodies in various assays including immunofluoroescence, immunocytochemistry, ELISA assays, flow cytometry, western blotting, testing for transcription of RNA in cells such as by RT-PCR.

In other embodiments, GTKO animals or cells contain additional genetic modifications. Genetic modifications can include more than just homologous targeting, but can also include random integrations of exogenous genes, mutations, deletions and insertions of genes of any kind. The additional genetic modifications can be made by further genetically modifying cells obtained from the transgenic cells and animals described herein or by breeding the animals described herein with animals that have been further genetically modified. Such animals can be modified to eliminate the expression of at least one allele of αGT gene, the CMP-Neu5Ac hydroxylase gene (see, for example, U.S. Pat. No. 7,368,284), the iGb3 synthase gene (see, for example, U.S. Patent Publication No. 2005/0155095), and/or the Forssman synthase gene (see, for example, U.S. Patent Publication No. 2006/0068479). In additional embodiments, the animals described herein can also contain genetic modifications to express fucosyltransferase, sialyltransferase and/or any member of the family of glucosyltransferases. To achieve these additional genetic modifications, in one embodiment, cells can be modified to contain multiple genetic modifications. In other embodiments, animals can be bred together to achieve multiple genetic modifications. In one specific embodiment, animals, such as pigs, lacking expression of functional immunoglobulin, produced according to the process, sequences and/or constructs described herein, can be bred with animals, such as pigs, lacking expression of αGT (for example, as described in WO 04/028243).

In another embodiment, the expression of additional genes responsible for xenograft rejection can be eliminated or reduced. Such genes include, but are not limited to the CMP-NEUAc Hydroxylase Gene, the isoGloboside 3 Synthase gene, and the Forssman synthase gene.

In addition, genes or cDNA encoding complement related proteins, which are responsible for the suppression of complement mediated lysis can also be expressed in the animals and tissues of the present invention. Such genes include, but are not limited to CD59, DAF (CD55), and CD46 (see, for example, WO 99/53042; Chen et al. Xenotransplantation, Volume 6 Issue 3 Page 194-August 1999, which describes pigs that express CD59/DAF transgenes; Costa C et al, Xenotransplantation. 2002 January; 9(1):45-57, which describes transgenic pigs that express human CD59 and H-transferase; Zhao L et al.; Diamond L E et al. Transplantation. 2001 Jan. 15; 71(1):132-42, which describes a human CD46 transgenic pigs.)

Additional modifications can include expression of compounds, such as antibodies, which down-regulate the expression of a cell adhesion molecule by the cells, such as described in WO 00/31126, entitled "Suppression of xenograft rejection by down regulation of a cell adhesion molecules" and compounds in which costimulation by signal 2 is prevented, such as by administration to the organ recipient of a soluble form of CTLA-4 from the xenogeneic donor organism, for example as described in WO 99/57266, entitled "Immunosuppression by blocking T cell costimulation signal 2 (B7/CD28 interaction)".

Nuclear Transfer

Engineered transgenic animals such as ungulates or pigs described herein may be produced using any suitable techniques known in the art. These techniques include, but are not limited to, microinjection (e.g., of pronuclei), sperm-mediated gene transfer, electroporation of ova or zygotes, and/or nuclear transplantation.

In certain embodiments, sperm mediated gene transfer can be used to produce the genetically modified ungulates described herein. The methods and compositions described herein to insert transgenes can be used to genetically modify sperm cells via any technique described herein or known in the art. The genetically modified sperm can then be used to impregnate a female recipient via artificial insemination, intracytoplasmic sperm injection or any other known technique. In one embodiment, the sperm and/or sperm head can be incubated with the exogenous nucleic acid for a sufficient time period. Sufficient time periods include, for example, about 30 seconds to about 5 minutes, typically about 45 seconds to about 3 minutes, more typically about 1 minute to about 2 minutes.

The potential use of sperm cells as vectors for gene transfer was first suggested by Brackeff et al., Proc., Natl. Acad. Sci. USA 68:353-357 (1971). This was followed by reports of the production of transgenic mice and pigs after in vitro fertilization of oocytes with sperm that had been incubated by naked DNA (see, for example, Lavitrano et al., Cell 57:717-723 (1989) and Gandolfi et al. Journal of Reproduction and Fertility Abstract Series 4, 10 (1989)), although other laboratories were not able to repeat these experiments (see, for example, Brinster et al. Cell 59:239-241 (1989) and Gavora et al., Canadian Journal of Animal Science 71:287-291 (1991)). Since then, successful sperm mediated gene transfer has been achieved in chicken (see, for example, Nakanishi and Iritani, Mol. Reprod. Dev. 36:258-261 (1993)); mice (see, for example, Maione, Mol. Reprod. Dev. 59:406 (1998)); and pigs (see, for example, Lavitrano et al. Transplant. Proc. 29:3508-3509 (1997); Lavitrano et al., Proc. Natl. Acad. Sci. USA 99:14230-5 (2002); Lavitrano et al., Mol. Reprod. Dev. 64-284-91 (2003)). Similar techniques are also described in U.S. Pat. No. 6,376,743; issued Apr. 23, 2002; U.S. Patent Publication Nos. 20010044937, published Nov. 22, 2001, and 20020108132, published Aug. 8, 2002).

In some embodiments, intracytoplasmic sperm injection can be used to produce the genetically modified ungulates described herein. This can be accomplished by coinserting an exogenous nucleic acid and a sperm into the cytoplasm of an unfertilized oocyte to form a transgenic fertilized oocyte, and allowing the transgenic fertilized oocyte to develop into a transgenic embryo and, if desired, into a live offspring. The sperm can be a membrane-disrupted sperm head or a demembranated sperm head. The coinsertion step can include the substep of preincubating the sperm with the exogenous nucleic acid for a sufficient time period, for example, about 30 seconds to about 5 minutes, typically about 45 seconds to about 3 minutes, more typically about 1 minute to about 2 minutes. The coinsertion of the sperm and exogenous nucleic acid into the oocyte can be via microinjection. The exogenous nucleic acid mixed with the sperm can contain more than one transgene, to produce an embryo that is transgenic for more than one transgene as described herein. The intracytoplasmic sperm injection can be accomplished by any technique known in the art, see, for example, U.S. Pat. No. 6,376,743.

Any additional technique known in the art may be used to introduce the transgene into animals. Such techniques include, but are not limited to pronuclear microinjection (see, for example, Hoppe, P. C. and Wagner, T. E., 1989, U.S. Pat. No. 4,873,191); retrovirus mediated gene transfer into germ lines (see, for example, Van der Putten et al., 1985, Proc. Natl. Acad. Sci., USA 82:6148-6152); gene targeting in embryonic stem cells (see, for example, Thompson et al., 1989, Cell 56:313-321; Wheeler, M. B., 1994, WO 94/26884); electroporation of embryos (see, for example, Lo, 1983, Mol Cell. Biol. 3:1803-1814); cell gun; transfection; transduction; retroviral infection; adenoviral infection; adenoviral-associated infection; liposome-mediated gene transfer; naked DNA transfer; and sperm-mediated gene transfer (see, for example, Lavitrano et al., 1989, Cell 57:717-723); etc. For a review of such techniques, see, for example, Gordon, 1989, Transgenic Anithals, Intl. Rev. Cytol. 115:171-229. In particular embodiments, the expression of CTLA4 and/or CTLA4-Ig fusion genes in ungulates can be accomplished via these techniques.

In one embodiment, microinjection of the constructs encoding the transgene can be used to produce the transgenic animals. In one embodiment, the nucleic acid construct or vector can be microinjection into the pronuclei of a zygote. In one embodiment, the construct or vector can be injected into the male pronuclei of a zygote. In another embodiment, the construct or vector can be injected into the female pronuclei of a zygote. In a further embodiment, the construct or vector can be injected via sperm-mediated gene transfer.

Microinjection of the transgene construct or vector can include the following steps: superovulation of a donor female; surgical removal of the egg, fertilization of the egg; injection of the transgene transcription unit into the pronuclei of the embryo; and introduction of the transgenic embryo into the reproductive tract of a pseudopregnant host mother, usually of the same species. See for example U.S. Pat. No. 4,873, 191, Brinster, et al. 1985. PNAS 82:4438; Hogan, et al., in "Manipulating the Mouse Embryo: A Laboratory Manual". Cold Spring Harbor Laboratory, Cold Spring Harbor, N.Y., 1986. Robertson, 1987, in Robertson, ed. "Teratocarcinomas and Embryonic Stem Cells a Practical Approach" IRL Press, Evnsham. Oxford, England. Pedersen, et al., 1990. "Transgenic Techniques in Mice—A Video Guide", Cold Spring Harbor Laboratory, Cold Spring Harbor, N.Y. Transgenic pigs are routinely produced by the microinjection of a transgene construct or vector into pig embryos. In one embodiment, the presence of the transgene can be detected by isolating genomic DNA from tissue from the tail of each piglet and subjecting about 5 micrograms of this genomic DNA to nucleic acid hybridization analysis with a transgene specific probe. In a particular embodiment, transgenic animals can be produced according to any method known to one skilled in the art, for example, as disclosed in Bleck et al., J. Anim. Sci., 76:3072 [1998]; also described in U.S. Pat. Nos. 6,872,868; 6,066,725; 5,523,226; 5,453,457; 4,873,191; 4,736,866; and/or PCT Publication No. WO/9907829.

In one embodiment, the pronuclear microinjection method can include linking at least approximately 50, 100, 200, 300, 400 or 500 copies of the transgene-containing construct or vector of the present invention to a promoter of choice, for example, as disclosed herein, and then the foreign DNA can be injected through a fine glass needle into fertilized eggs. In one embodiment, the DNA can be injected into the male pronucleus of the zygote. Pig zygotes are opaque and visualization of nuclear structures can be difficult. In one embodiment, the pronuclei or nuclei of pig zygotes can be visualized after centrifugation, for example, at 15000 g for 3 mm. The injection of the pronucleus can be carried out under magnification and use of standard microinjection apparatus. The zygote can be held by a blunt holding pipette and the zona pellucida, plasma membrane and pronuclear envelope can be penetrated by an injection pipette. The blunt holding pipette can have a small diameter, for example, approximately 50 um. The injection pipette can have a smaller diameter than the holding pipette, for example, approximately 15 um. DNA integration occurs during replication as a repair function of the host DNA. These eggs, containing the foreign DNA, can then be implanted into surrogate mothers for gestation of the embryo according to any technique known to one skilled in the art.

In some embodiments, pronuclear microinjection can be performed on the zygote 12 hours post fertilization. Uptake of such genes can be delayed for several cell cycles. The consequence of this is that depending on the cell cycle of uptake, only some cell lineages may carry the transgene, resulting in mosaic offspring. If desired, mosaic animals can be bred to form true germline transgenic animals.

In other embodiments, ungulate cells such as porcine cells containing transgenes can be used as donor cells to provide the nucleus for nuclear transfer into enucleated oocytes to produce cloned, transgenic animals. In one embodiment, the ungulate cell need not express the transgene protein in order to be useful as a donor cell for nuclear transfer. In one embodiment, the porcine cell can be engineered to express a transgene from a nucleic acid construct or vector that contains a promoter. Alternatively, the porcine cells can be engineered to express transgene under control of an endogenous promoter through homologous recombination. In one embodiment, the transgene nucleic acid sequence can be inserted into the genome under the control of a tissue specific promoter, tissue specific enhancer or both. In another embodiment, the transgene nucleic acid sequence can be inserted into the genome under the control of a ubiquitous promoter. In certain embodiments, targeting vectors are provided, which are designed to allow targeted homologous recombination in somatic cells. These targeting vectors can be transformed into mammalian cells to target the endogenous genes of interest via homologous recombination. In one embodiment, the targeting construct inserts both the transgene nucleotide sequence and a selectable maker gene into the endogenous gene so as to be in reading frame with the upstream sequence and produce an active fusion protein. Cells can be transformed with the constructs using the methods of the invention and are selected by means of the selectable marker and then screened for the presence of recombinants.

The present invention provides a method for cloning an ungulate such as a pig containing certain transgenes via somatic cell nuclear transfer. In general, the pig can be produced by a nuclear transfer process comprising the following steps: obtaining desired differentiated pig cells to be used as a source of donor nuclei; obtaining oocytes from a pig; enucleating said oocytes; transferring the desired differentiated cell or cell nucleus into the enucleated oocyte, e.g., by fusion or injection, to form nuclear transfer (NT) units; activating the resultant NT unit; and transferring said cultured NT unit to a host pig such that the NT unit develops into a fetus.

Nuclear transfer techniques or nuclear transplantation techniques are known in the art (see, for example, Dai et al. Nature Biotechnology 20:251-255; Polejaeva et al Nature 407:86-90 (2000); Campbell, et al., *Theriogenology* 68 Suppl 1:S214-3 1 (2007); Vajta, et al., *Reprod Fertil Dev* 19(2): 403-23 (2007); Campbell et al. (1995) Theriogenology, 43:181; Collas et al. (1994) Mol. Report Dev., 38:264-267; Keefer et al. (1994) Biol. Reprod., 50:935-939; Sims et al. (1993) Proc. Natl. Acad. Sci., USA, 90:6143-6147; WO 94/26884; WO 94/24274, and WO 90/03432, U.S. Pat. Nos. 4,944,384, 5,057,420, WO 97/07669, WO 97/07668, WO 98/30683, WO 00/22098, WO 004217, WO 00/51424, WO 03/055302, WO 03/005810, U.S. Pat. Nos. 6,147,276, 6,215, 041, 6,235,969, 6,252,133, 6,258,998, 5,945,577, 6,525,243, 6,548,741, and Phelps et al. (Science 299:411-414 (2003)).

A donor cell nucleus, which has been modified to contain a transgene of the present invention, is transferred to a recipient porcine oocyte. The use of this method is not restricted to a particular donor cell type. The donor cell can be as described in Wilmut et al. (1997) Nature 385:810; Campbell et al. (1996) Nature 380:64-66; or Cibelli et al. (1998) Science 280:1256-1258. All cells of normal karyotype, including embryonic, fetal and adult somatic cells which can be used successfully in nuclear transfer can in principle be employed. Fetal fibroblasts are a particularly useful class of donor cells. Generally suitable methods of nuclear transfer are described in Campbell et al. (1995) Theriogenology 43:181, Collas et al. (1994) Mol. Reprod. Dev. 38:264-267, Keefer et al. (1994) Biol. Reprod. 50:935-939, Sims et al. (1993) Proc. Nat'l. Acad. Sci. USA 90:6143-6147, WO-A-9426884, WO-A-9424274, WO-A-9807841, WO-A-9003432, U.S. Pat. No. 4,994,384 and U.S. Pat. No. 5,057,420, Campbell et al., (2007) Theriogenology 68 Suppl 1, S214-231, Vatja et al., (2007) Reprod Fertil Dev 19, 403-423). Differentiated or at least partially differentiated donor cells can also be used. Donor cells can also be, but do not have to be, in culture and can be quiescent. Nuclear donor cells which are quiescent are cells which can be induced to enter quiescence or exist in a quiescent state in vivo. Prior art methods have also used embryonic cell types in cloning procedures (see, for example, Campbell et al. (1996) Nature, 380:64-68) and Stice et al. (1996) Biol. Reprod., 20 54:100-110). In a particular embodiment, fibroblast cells, such as porcine fibroblast cells can be genetically modified to contain the transgene of interest.

Methods for isolation of oocytes are well known in the art. Essentially, this can comprise isolating oocytes from the ovaries or reproductive tract of a pig. A readily available source of pig oocytes is slaughterhouse materials. For the combination of techniques such as genetic engineering, nuclear transfer and cloning, oocytes must generally be matured in vitro before these cells can be used as recipient cells for nuclear transfer, and before they can be fertilized by the sperm cell to develop into an embryo. This process generally requires collecting immature (prophase I) oocytes from mammalian ovaries, e.g., bovine ovaries obtained at a slaughterhouse, and maturing the oocytes in a maturation medium prior to fertilization or enucleation until the oocyte attains the metaphase II stage, which in the case of bovine oocytes generally occurs about 18-24 hours post-aspiration and in the case of porcine generally occurs at about 35-55 hours. This period of time is known as the maturation period."

A metaphase II stage oocyte can be the recipient oocyte, at this stage it is believed that the oocyte can be or is sufficiently "activated" to treat the introduced nucleus as it does a fertilizing sperm. Metaphase II stage oocytes, which have been matured in vivo have been successfully used in nuclear transfer techniques. Essentially, mature metaphase II oocytes can be collected surgically from either non-superovulated or superovulated porcine 35 to 48, or 39-41, hours past the onset of estrus or past the injection of human chorionic gonadotropin (hCG) or similar hormone.

After a fixed time maturation period, the oocytes can be enucleated. Prior to enucleation the oocytes can be removed and placed in appropriate medium, such as HECM or TCM199 containing 1 milligram per milliliter of hyaluronidase prior to removal of cumulus cells. The stripped oocytes can then be screened for polar bodies, and the selected metaphase II oocytes, as determined by the presence of polar bodies, are then used for nuclear transfer. Enucleation follows.

Enucleation can be performed by known methods, such as described in U.S. Pat. No. 4,994,384. For example, metaphase II oocytes can be placed in either HECM, optionally containing 7-10 micrograms per milliliter cytochalasin B, for immediate enucleation, or can be placed in a suitable medium, for example an embryo culture medium such as CR1aa, plus 10% estrus cow serum, and then enucleated later, for example not more than 24 hours later or 16-18 hours later.

Enucleation can be accomplished microsurgically using a micropipette to remove the polar body and the adjacent cytoplasm. The oocytes can then be screened to identify those of which have been successfully enucleated. One way to screen the oocytes is to stain the oocytes with 3-10 microgram per milliliter 33342 Hoechst dye in suitable holding medium, and then view the oocytes under ultraviolet irradiation for less than 10 seconds. The oocytes that have been successfully enucleated can then be placed in a suitable culture medium, for example, CR1aa plus 10% serum.

A single mammalian cell of the same species as the enucleated oocyte can then be transferred into the perivitelline space of the enucleated oocyte used to produce the NT unit. The mammalian cell and the enucleated oocyte can be used to produce NT units according to methods known in the art. For example, the cells can be fused by electrofusion. Electrofusion is accomplished by providing a pulse of electricity that is sufficient to cause a transient breakdown of the plasma membrane. This breakdown of the plasma membrane is very short because the membrane reforms rapidly. Thus, if two adjacent membranes are induced to breakdown and upon reformation the lipid bilayers intermingle, small channels can open between the two cells. Due to the thermodynamic instability of such a small opening, it enlarges until the two cells become one. See, for example, U.S. Pat. No. 4,997,384 by Prather et al. A variety of electrofusion media can be used including, for example, sucrose, mannitol, sorbitol and phosphate buffered solution. For example, the fusion media can comprise a 280 milli molar (mM) solution of mannitol, containing 0.05 mM $MgCl_2$ and 0.001 mM $CaCl_2$ (Walker et al., Cloning and Stem Cells. 2002; 4(2):105-12). Fusion can also be accomplished using Sendai virus as a fusogenic agent (Graham, Wister Inot. Symp. Monogr., 9, 19, 1969). Also, the nucleus can be injected directly into the oocyte rather than using electroporation fusion. See, for example, Collas and Barnes, (1994) Mol. Reprod. Dev., 38:264-267. After fusion, the resultant fused NT units are then placed in a suitable medium until activation, for example, CR1aa medium. Typically activation can be effected shortly thereafter, for example less than 24 hours later, or about 4-9 hours later for bovine NT and 1-4 hours later for porcine NT.

The NT unit can be activated by known methods. Such methods include, for example, culturing the NT unit at subphysiological temperature, in essence by applying a cold, or actually cool temperature shock to the NT unit. This can be most conveniently done by culturing the NT unit at room temperature, which is cold relative to the physiological temperature conditions to which embryos are normally exposed. Alternatively, activation can be achieved by application of known activation agents. For example, penetration of oocytes by sperm during fertilization has been shown to activate pre-lusion oocytes to yield greater numbers of viable pregnancies and multiple genetically identical calves after nuclear transfer. Also, treatments such as electrical and chemical shock can be used to activate NT embryos after fusion. See, for example, U.S. Pat. No. 5,496,720 to Susko-Parrish et al. Additionally, activation can be effected by simultaneously or sequentially by increasing levels of divalent cations in the oocyte, and reducing phosphorylation of cellular proteins in the oocyte. This can generally be effected by introducing divalent cations into the oocyte cytoplasm, e.g., magnesium, strontium, barium or calcium, e.g., in the form of an ionophore. Other methods of increasing divalent cation levels include the use of electric shock, treatment with ethanol and treatment with caged chelators. Phosphorylation can be reduced by known methods, for example, by the addition of kinase inhibitors, e.g., serine-threonine kinase inhibitors, such as 6-dimethyl-aminopurine, staurosporine, 2-aminopurine, and sphingosine. Alternatively, phosphorylation of cellular proteins can be inhibited by introduction of a phosphatase into the oocyte, e.g., phosphatase 2A and phosphatase 2B.

The activated NT units can then be cultured until they reach a suitable size for transferring to a recipient female, or alternately, they may be immediately transferred to a recipient female. Culture media suitable for culturing and maturation of embryos are well known in the art. Examples of known media, which can be used for embryo culture and maintenance, include Ham's F-10+10% fetal calf serum (FCS), Tissue Culture Medium-199 (TCM-199)+10% fetal calf serum, Tyrodes-Albumin-Lactate-Pyruvate (TALP), Dulbecco's Phosphate Buffered Saline (PBS), Eagle's Whitten's media, PZM, NCSU23 and NCSU37. See Yoshioka K, Suzuki C, Tanaka A, Anas I M, Iwamura S. Biol Reprod. (2002) January; 66(1):112-9 and Petters R M, Wells K D. J Reprod Fertil Suppl. 1993; 48:61-73.

Afterward, the cultured NT unit or units can be washed and then placed in a suitable media contained in well plates which can optionally contain a suitable confluent feeder layer. Suitable feeder layers include, by way of example, fibroblasts and epithelial cells. The NT units are cultured on the feeder layer until the NT units reach a size suitable for transferring to a recipient female, or for obtaining cells which can be used to produce cell colonies. NT units can be cultured until at least about 2 to 400 cells, about 4 to 128 cells, or at least about 50 cells. Alternatively, NT units may be immediately transferred to a recipient female.

The methods for embryo transfer and recipient animal management in the present invention are standard procedures used in the embryo transfer industry. Synchronous transfers are important for success of the present invention, i.e., the stage of the NT embryo is in synchrony with the estrus cycle of the recipient female. See, for example, Siedel, G. E., Jr. (1981) "Critical review of embryo transfer procedures with cattle in Fertilization and Embryonic Development in Vitro, L. Mastroianni, Jr. and J. D. Biggers, ed., Plenum Press, New York, N.Y., page 323. Porcine embryo transfer can be conducted according to methods known in the art. For reference, see Youngs et al. "Factors Influencing the Success of Embryo Transfer in the Pig," Theriogenology (2002) 56: 1311-1320.

Production of Islet Related Cells

The pancreas is a gland organ in the digestive and endocrine system of vertebrates. It is both an endocrine gland producing several important hormones, including insulin, glucagon, and somatostatin, as well as an exocrine gland, secreting pancreatic juice containing digestive enzymes that pass to the small intestine. The bulk of the pancreas is composed of pancreatic exocrine cells and their associated ducts. Embedded within this exocrine tissue are roughly one million small clusters of cells called the Islets of Langerhans, which are the endocrine cells of the pancreas and secrete insulin, glucagon and several other hormones.

The human pancreas contains approximately 1 million islets of Langerhans. They are small spheroid clusters of cells, distributed throughout the organ. They vary considerably in size, ranging from tens of cells to several 1000 cells. "Islet cells" include a collective group of cell types found in an Islet of Langerhans They comprise the A, B, C, D and PP cells, which can be relatively difficult to distinguish using standard staining techniques. $\alpha$ cells secrete glucagon (increase glucose in blood), $\beta$ cells secrete insulin (decrease glucose in blood), $\delta$ cells secrete somatostatin (regulates/stops $\alpha$ and $\beta$ cells), and PP cells secrete pancreatic polypeptide.

In one embodiment, genetically altered pigs are used as donors of pancreatic tissue, including pancreatic islets and/or islet cells. The pancreatic tissue or cells derived from such tissue can comprise pancreatic islet cells, or islets, or islet-cell clusters. In particular embodiments, the cells are pancreatic islets. In more particular embodiments, the cells are pancreatic beta cells. In certain embodiments, the cells are insulin-producing. In still further embodiments, the cells are islet-like cells. Islet cell clusters can include any one or more of alpha, beta, delta, PP or epsilon cells. Generally, alpha cells producing glucagons make up about 15-20% of total islet cells in native pancreas, beta cells producing insulin and amylin make up between about 65-80% of islet cells in native pancreas, delta cells producing somatostatin make up about 3-10% of total islet cells in native pancreas, PP cells producing pancreatic polypeptide make up about 3-5% of total islet cells in native pancreas and epsilon cells producing ghrelin make up <1% of total islet cells in native pancreas (see Elayat et al. (1995). J. Anat. 186: 629-37). http://www.ncbi.nlm.nih.gov/pmc/articles/PMC1167020/

The donor pigs may be at any stage of development including, but not limited to, fetal, neonatal, young and adult. In some embodiments, islet cells are isolated from adult porcine transgenic animals. In alternate embodiments, islet cells are isolated from fetal or neonatal porcine transgenic animals (see e.g. Mandel (1999) J. Mol. Med. 77:155-60; Cardona, et al. (2006) Nat. Med. 12:304-6). The donor pigs may be under the age of 10, 9, 8, 7, 6, 5, 4, 3, 2, or 1 year(s). In one embodiment, the islet cells are isolated from transgenic pigs under the age of 6 years. In another embodiment, the islet cells are isolated from transgenic pigs under the age of 3 years. The donor pigs may be any age between 0 to 2 years, 2 to 4 years, 4 to 6 years, 6 to 8 years, or 8 to 10 years. In some cases, the donor pigs is older than 10 years. In another embodiment, the islet cells are isolated from newborn to 2 year old transgenic pigs. In one embodiment, the islets cells are isolated from fetal to 2 year old transgenic pigs. In a particular embodiment, the islets cells are isolated from 6 months old to 2 year old transgenic pigs, and in a more particular embodiment, 7 months old to 1 year old transgenic pigs. In one embodiment, the islet cells are isolated from 2-3 year old transgenic pigs. In some cases, the donor pig is less than 0 year (i.e. a fetus or embryo). Neonatal islets are more hearty and consistent post-isolation than adult islets, are more resistant to oxidative stress, have significant growth potential (likely from a nascent islet stem cell subpopulation), such that they have the ability to proliferate post-transplantation and engraftment in the transplantation site. They have the disadvantage that it can take them up to 4-6 weeks to mature enough such that they are producing significant levels of insulin, but this is overcome by treatment with exogenous insulin for the period sufficient for the maturation of the neonatal islets. Survival and functional engraftment of neonatal islets can be determined by measuring porcine-specific c-peptide levels, which are easily distinguished from any potential endogenous c-peptide.

Adult porcine islets may be isolated according to a modification of the method described for human islets and further optimized for pigs (Toso, 2000; Yonekawa, 2005), as described previously (Bottino, 2002, 2004; Balamurugan, 2003, 2005). Purity can be evaluated after dithizone staining of islet samples, and expressed as percent of islets/whole tissue (Balamurugan, 2005). Islets can be cultured for 1-3 days prior to transplantation in order to deplete the preparation of contaminating exocrine tissue. Prior to Tx, pig islets can be counted, and viability assessed by double fluorescent calcein-AM and propidium iodide stain (Lorenzo, 1994). It is recommend that islet cell viability be >75% in all preparations, and purity be >80% islets/whole tissue. Functional properties of the islets, including dynamic perifusion and viability, can be determined in vitro prior to Tx (Balamurugan, 2006). In some embodiments, transgenic porcine islet cells are cultured in-vitro to expand, mature, and/or purify them so that they are suitable for grafting.

In certain embodiments, the donor transgenic pancreatic tissue is surgically removed. Following surgical removal, the donor pancreases are transferred to a cleanroom facility for further processing in a cold plastic container in 50 ml tubes containing cold Hanks' Balanced Salt Solution (HBSS) with 0.2% human serum albumin (HSA) added. Blood samples from each donor are sent for virology testing and *toxoplasma* serology. Samples from each organ are kept in a freezer at −80° C. for future testing if necessary.

The islet cells may be isolated by standard collagenase digestion of the minced pancreas via the procedure documented by Ricordi et al. (1990), though with some modifications. Using aseptic technique, the glands are distended with Liberase™ (a mixture of purified enzymes formulated for rapid dissociation of rodent pancreas and maximal recovery of healthy, intact, and functional islets of Langerhans, wherein the target substrates for these enzymes are not fully identified, but are presumed to be collagen and non-collagen proteins, which comprise the intercellular matrix of pancreatic acinar tissue). (1.5 mg/ml), trimmed of excess fat, blood vessels and connective tissue, minced, and digested at 37 degree C. in a shaking water bath for 15 minutes at 120 rpm. The digestion is achieved using lignocaine mixed with the Liberase™. solution to avoid cell damage during digestion. Following the digestion process, the cells are passed through a sterile 400 mm mesh into a sterile beaker. A second digestion process is used for any undigested tissue.

Alternatively, Vitacyte collagenase MA (7.5 Wunsch Units/gram of pancreatic tissue) and Vitacyte BP protease (0.13 mg/gram of pancreatic tissue) can be used.

In certain embodiments, Liberase™ (eg; sourced in New Zealand from Roche) is used rather than collagenase (see "Improved Pig Islet Yield and Post-Culture Recovery Using Liberase P1 Purified Enzyme Blend", T J Cavanagh et al. Transplantation Proceedings 30, 367 (1998) and in "Significant Progress In Porcine Islets Mass Isolation Utilizing Liberase™ HI For Enzymatic Low-Temperature Pancreas Digestion", H. Brandhorst et al. Transplantation Vol 68, 355-361 No. 3, Aug. 15, 1999). The digested tissue is washed three times, and seeded into cell culture media RPMI 1640 to which is added 2% human serum albumin (HSA), 10 mmol/L nicotinamide, and antibiotic (Ciproxin).

To exclude any contamination of the tissue, quality control procedures are undertaken on cell culture samples after isolation and before encapsulation. Three days after isolation, the cell culture is tested for microbiological contamination by accredited laboratories. Testing for porcine endogenous retrovirus (PERV) may be undertaken, for example, at the Virology Laboratory, Auckland Hospital.

The islet yield is determined via dithizone (DTZ) staining of the cells. Dithizone is a zinc-chelating agent and a supravital stain that selectively stains zinc in the islets of Langherhans, producing a distinctive red appearance.

The viability of the islet cells can be determined using acridin orange and propidium iodide. Acridin orange is a fluorescent stain that readily passes through all cell membranes to stain the cytoplasm and nucleus. Bright green fluorescence in both the nucleus and cytoplasm on exposure to ultraviolet (UV) light denotes intact live cells. Conversely, propidium iodide is a fluorescent stain that cannot pass through an intact membrane. It emits a bright red fluorescence when exposed to LIV light, and the presence of propidium iodide in a cell nucleus indicates severe damage or a dead cell.

Static glucose stimulation (SGS) is used to assess in vitro function of the porcine islets by exposing them to low and high concentrations of glucose and theophylline. Determination of the in vitro insulin secretory capacity is undertaken on both free islets (after 3 days in culture) and after their subsequent encapsulation.

When immature porcine islet are used, the IgF-1 (Human Insulin-like Growth Factor I) can be used in order to induce immature cells to mature to their insulin-producing form. IgF-1 is a potent mitogenic growth factor that mediates the growth promoting activities of growth hormone postnatally. Both IgF-1 and IgF-2 are expressed in many cell types and may have endocrine, autocrine and paracrine functions. The preferred form of IgF-1 is the amino-terminal tripeptide glycine-proline-glutamate of IgF-1 (GPE).

The processes by which islets are purified prior to transplantation are traumatic to these highly specialized tissues. Such trauma can induce necrosis or apoptosis. Any method to prepare and encapsulate the islets known in the state of the art may be used in this invention. These techniques include microencapsulation of individual islets, or macroencapsulation of multiple islets/pancreas tissue. Examples of these include the following:

U.S. Pat. No. 7,427,415 to Scharp et al., discloses a method of encapsulating a biological material which includes the steps of: adding a solution which includes a first buffer to the biological material; centrifuging the biological material to form a pelleted biological material; removing supernatant; adding a solution which includes a photoinitiator dye conjugated to a cell adsorbing material to the pelleted biological material; resuspending and incubating the pelleted biological material with the solution including the photoinitiator dye conjugated to the cell adsorbing material for an effective amount of time; centrifuging mixture; removing the solution including the photoinitiator dye conjugated to the cell adsorbing material; resuspending the pelleted biological material with a second solution including a second buffer; centrifuging and removing the second buffer; resuspending and mixing the biological material with a photoactive polymer solution; and irradiating the resuspended biological material with a photoactive polymer solution with an energy source to form an encapsulated biological material. Preferably, the encapsulated biological material is a PEG conformal coated islet allograft.

Other procedures have ensured zero warm ischemia (compared with hours with most human islet preparations), have involved the use of nicotinamide to enhance successful in vitro explantation, have involved minimal incubation time with collagenase or Liberase, have involved swift non-traumatic encapsulation technology, have involved the use of IgF-1 (or the GPE tripeptide thereof), the use of an anaesthetic such as lignocaine, and the use of an antibiotic such as ciproproxin etc.

U.S. Pat. No. 7,122,177 to Elliott et al. disclosed a method for encapsulating pancreatic islets. Sodium alginate used for this procedure is extracted from raw material sources (seaweed) and prepared in a powdered ultrapure form. The sterile sodium alginate solution (1.6%) is then utilized at the Diatranz Islet Transplant Centre to manufacture encapsulated islets. Generally each encapsulation involves presenting islets and a suitable alginate solution (usually sodium alginate) into a source of compatible cations thereby to entrap the islets in a cation-alginate gel (usually calcium-alginate gel).

The encapsulation procedure involves extruding a mixture of islets and sodium alginate solution (1.6% w/w) through a droplet generating needle into a bath of gelling cations (calcium chloride). The islets entrapped in the calcium-alginate gel are then coated with positively charged poly-L-ornithine followed by an outer coat of alginate (0.05%). The central core of alginate is then liquefied by the addition of sodium citrate. Most capsules contain 3 islets and have a diameter of 300 to 400 um.

After liquification of the alginate entrapping the islets, the "capsules" are washed, and again coated with alginate which neutralizes any residual change on the poly-L-ornithine coating and prevents direct contact of the poly-L-ornithine with tissues when the entire capsule is transplanted. The encapsulated islets are kept in cell culture, and then checked for contamination, insulin release and viability before transplantation. They are only released for transplantation if all quality control tests are negative.

U.S. Pat. No. 6,303,355 to Opara discloses a method of treating isolated living cells by first culturing the cells in a medium containing at least one of (or a combination of): an antioxidant, an anti-cytokine, an anti-endotoxin, or an antibiotic. The cells are then microencapsulated in a biocompatible microcapsule that contains a hydrogel core and a semipermeable outer membrane, to provide a microcapsule containing living cells therein.

U.S. Pat. No. 5,578,314 to Cochrum et al. discloses a method for production of functional cell and tissue transplants coated with multiple layer coatings of purified alginate gel with uniform minimum thickness. This method can withstand mechanical, chemical or immune destruction within the host, does not provoke fibrogenic reactions impairing the transplants function, and provides a uniform and controllable thickness of the coating to allow for free permeability of nutrients and secretory and waste products. The uniform coating has a thickness of between about 20-200 um which would eliminate fibrogenic and/or immune reactions destructive to the transplant's functionality and provide substantially complete coverage of the biological tissue core, thus allowing a successful long-term transplantation of these cells or tissues. Cochrum et al. state that their method is unique in that stabilization of the first and subsequent coat by polylysine or other polyamino acid or polycation is not required. The method allows optionally the formation of a halo layer, providing an intermediate layer between an inner and outer coating that uniformly covers an exposed area of biological tissue.

Further direction regarding islet cell isolation may be found in the following references: Qi, et al., Human pancreatic islet isolation: Part I: digestion and collection of pancreatic tissue and Part II: purification and culture of human islets, J Vis Exp, 27. May 2009.

Encapsulation of cellular grafts in an immunoisolation membrane device such as a TheraCyte macroencapsulation device can also be used (see Rafael, et al. (2000) Cell Transpl. 9:107-13). Another technique is the "Valdez capsules" as described in Valdes (1998) "Biological Encapsulation as a New Model for Preservation of Islets of Langerhans" Transplantation Proceed 30:481. Alginate sheets can also be used for encapsulation as can beta cell embedding. In technique involving the production of alginate sheets, an islet sheet is provided as a thin planar bioartificial endocrine pancreas fabricated by gelling highly purified alginate and islets of Langerhans. Acellular alginate layers form a uniform immunoprotective barrier to host rejection of the encapsulated cells, with the tissue nourished by passive diffusion from adjacent host tissue (see Stors, et al. (2006) Ann. NY Ac. Sci. 944:252-266).

The transgenic islets may also be co-transplanted with other cells types such as sertoli cells or stem cells, including in particular mesenchymal stem cells (see Osiris Inc. http://www.osiristx.com/).

Method of Treatment

The invention described herein encompasses methods of treatment or preventing diabetes or prediabetes. The methods include, but are not limited to, administering one or more pancreatic islet cell(s) from a donor animal described herein to a host in need thereof. The method may be transplantation or, in some cases, xenotranplantation. The donor animal may be a porcine. The host may be a primate, for example, a non-human primate including, but not limited to, a monkey. The host may be a human and in some cases, a human with diabetes or pre-diabetes.

One method of the invention is a method of xenotransplantation wherein the transgenic pancreatic tissues or cells provided herein are transplanted into a primate and, after the transplant, the primate requires reduced or no exogenous insulin. In another embodiment, the primate requires reduced levels or no exogenous insulin post-transplant. It is generally understood that post-transplant refers to the period of time after the development of a state of normoglycemia (which may take, for example, approximately 4 or 12 weeks). After the transplant, the primate may require 5%, 10%, 20%, 30%, 40%, 50%, 60%, 70%, 80%, 90% or 100% less insulin than that required prior to the transplant. After the transplant, the primate may require about 5% to about 25% less insulin than that required prior to the transplant. After the transplant, the primate may require about 25% to about 50% less insulin than that required prior to the transplant. After the transplant, the primate may require about 50% to about 75% less insulin than that required prior to the transplant. After the transplant, the primate may require about 75% to about 100% less insulin than that required prior to the transplant. After the transplant, the primate may require less than 0.6, 0.5, 0.4, 0.3, 0.2, 0.1, 0.05, or 0.01 exogenous units of insulin per kilogram (kg) per day. In one embodiment, the primate after the transplant requires any number less than about 0.01 to about 0.1 exogenous units of insulin per kilogram (kg) per day. In one embodiment, the primate after the transplant requires any number less than about 0.1 to about 0.25 exogenous units of insulin per kilogram (kg) per day. In one embodiment, the primate after the transplant requires any number less than about 0.25 to about 0.5 exogenous units of insulin per kilogram (kg) per day. In one embodiment, the primate after the transplant requires any number less than about 0.5 to about 0.6 exogenous units of insulin per kilogram (kg) per day. In one embodiment, after the transplant, the primate requires less than 4 units of insulin/day. In one embodiment, after the transplant, the primate requires less than 2 units of insulin/day. In one embodiment, after the transplant, the primate requires no exogenous insulin In one embodiment, after the transplant, the primate requires less than 1 IU per kg per day of insulin. In another particular embodiment, the primate requires less than 0.50 IU/kg per day.

The methods of the invention also include methods of xenotransplantation wherein the transgenic pancreatic tissues or cells provided herein are transplanted into a primate and, after the transplant, the primate requires minimal or no immunosuppressive therapy. Reduced or no immunosuppressive therapy includes, but is not limited to, a reduction (or complete elimination of) in dose of the immunosuppressive drug(s)/agent(s) compared to that required by other methods; a reduction (or complete elimination of) in the number of types of immunosuppressive drug(s)/agent(s) compared to that required by other methods; a reduction (or complete elimination of) in the duration of immunosuppression treatment compared to that required by other methods; and/or a reduction (or complete elimination of) in maintenance immunosuppression compared to that required by other methods.

The methods of the invention also include methods of xenotransplantation wherein the transgenic pancreatic tissues or cells provided herein are transplanted into a primate, wherein the IEQ/kg (pancreatic islet equivalents per kg) requirements are reduced compared to other methods. The IEQ/kg required by the novel invention described here may be, but is not limited to, below about 100,000; 90,000; 80,000; 70,000; 60,000; 50,000; 40,000; 30,000; 20,000; 10,000 or 5,000. The IEQ/kg required by the novel invention described here may be between about 5,000 to about 10,000; about 10,000 to about 15,000; about 15,000 to about 20,000; about 20,000 to about 25,000; about 25,000 to about 30,000; about 30,000 to about 35,000; about 35,000 to about 40,000; about 40,000 to about 45,000; about 45,000 to about 50,000; about 50,000 to about 55,000; about 55,000 to about 60,000; about 60,000 to about 65,000; about 65,000 to about 70,000; about 70,000 to about 75,000; about 75,000 to about 80,000; about 80,000 to about 85,000; about 85,000 to about 90,000; about 90,000 to about 95,000; about 95,000 to about 100,000. In one embodiment, the IEQ/kg is below 100,000. In one embodiment, the IEQ/kg is below 50,000. In one embodiment, the IEQ/kg is below 25,000. In one embodiment, the IEQ/kg is below 10,000.

The methods of the invention also include methods of treating or preventing diabetes wherein the transgenic pancreatic tissues or cells provided herein are transplanted into a primate and, after the transplant, the primate has some or all functional transplanted islets. The transplanted primate may have more functional transplanted islets when compared to the level prior to transplant or when compared to the level achieved using other methods. The islets may be characterized as functional using any definition known to one of skill in the art, including, but not limited to, the ability to produce insulin, the ability to reduce the host's exogenous insulin requirements, and/or the ability to produce donor type C-peptide. In one embodiment, islet functionality is defined as basal or stimulated porcine C-peptide greater than 0.3 ng/dl. In one embodiment, islet functionality is defined as detectable C-peptide in combination with a greater than 50% reduction of exogenous insulin needs, wherein the C-peptide is produced from the transplanted material.

The methods of the invention also include methods of treating or preventing diabetes wherein the transgenic pancreatic tissues or cells provided herein are transplanted into a primate and, after the transplant, the fasting and non-fasting blood glucose levels of the primate are maintained at normal levels/These normal levels may be maintained for any length of time, including, but not limited to, at least about 3, 6, 12, 24, or 36 months after the transplant. In one embodiment, the normal levels should be maintained for at least 3 months. In another embodiment, the normal levels should be maintained for at least 6 months. In another embodiment, the normal levels should be maintained for at least 12 months. Normal fasting and non-fasting blood glucose levels for primates, including but not limited to humans and monkeys, are known to one of skill in the art. In a particular embodiment, FBG can be maintained from about 70 to about 100 mg/dL (3.9 to 5.5 mmol/L). In another particular embodiment, NFBG can be maintained at less than about 200 mg/dL.

In some cases, normal levels of glucose are between about 70-130 mg/dl or 3.9-7.2 mmol/l when tested randomly (without regard to fasting or non-fasting state) and averaged. In some cases, normal levels of glucose are about between 65-70 mg/dl after fasting. In certain embodiments, the glucose levels after the transplant are maintained at approximately less than about 200 mg/dl, 175 mg/dl, 150 mg/dl, 125 mg/dl, 100 mg/dl, 75 mg/dl, or 50 mg/dl. In one embodiment, the glucose level after the transplant and after an overnight fast is below 140 mg/dl and this post-fast level is achieved at least 1 times per week for at least 1 month.

In one embodiment, the mean glucose levels (average of morning and evening levels) after the transplant are about between 2-5 mmol/l or about between 3-4 mmol/l.

In one embodiment, after the transplant, the primate has adequate glycemic control. In one embodiment, after the transplant, the glycated hemoglobin level is less than about 8%, 7%, 6%, 5%, 4% or 3%. In a particular embodiment, the glycated hemoglobin level after the transplant is less than 6.5%.

The methods of the invention also include methods of treating or preventing diabetes wherein the transgenic pancreatic tissues or cells provided herein are transplanted into a primate and, after the transplant, the primate successfully passes an intravenous glucose tolerance test. The test can be performed any time after the transplant, for example, but not limited to, at 1, 3, 6 and/or 12 months after the transplant. In some cases, the results of the test are successful if significant response to glucose in the form of donor (for example, porcine) C-peptide is demonstrated in the absence of a significant response of host (for example, primate) C-peptide.

The methods of the invention also include methods of treating or preventing diabetes wherein the transgenic pancreatic tissues or cells provided herein are transplanted into a primate and, after the transplant, the primate successfully passes an arginine stimulation test. The test can be performed any time after the transplant, for example, but not limited to, at 1, 3, 6 and/or 12 months after the transplant. In some cases, the results of the test are successful if significant response to glucose in the form of donor (for example, porcine) C-peptide is demonstrated in the absence of a significant response of host (for example, primate) C-peptide.

The methods of the invention also include methods of xenotransplantation wherein the transgenic pancreatic tissues or cells provided herein are transplanted into a primate and, after the transplant, donor C-peptide levels are detectable. In some instances, the donor C-peptide levels are porcine and, in some cases, the porcine C-peptide levels are about between 0.2 to about 1.0, about between 0.2 to about 0.75, about between 0.2 to about 0.65, about between 0.2 to about 0.55, about between 0.2 to about 0.45, or about between 0.2 to about 0.35 ng/ml. The donor porcine levels after transplant may be about 0.2, 0.3, 0.4, 0.5, 0.6, 0.7, 0.8, 0.9 or 1.0 ng/ml. In some cases, the donor porcine levels are greater than 1.0 ng/ml. In some cases, the donor porcine levels are greater than zero. In one embodiment, donor porcine C-peptide levels are about 0.5 ng/ml.

The methods of the invention also include methods of treating or preventing diabetes wherein after the transplantation of transgenic pancreatic tissues or cells, histological analysis of the host primate is conducted. In some cases, the histological analysis of the native pancreas after necropsy indicates reduced, or in one non-limiting example, no, insulin-positive beta cells. In these cases or in other cases wherein the native pancreas is not examined, the histological examination of the liver or other site of islet transplant indicates multiple viable insulin-positive cells.

The methods of the invention also include methods of treating or preventing diabetes wherein after the transplantation of transgenic pancreatic tissues or cells, there are not numerous, or serious life-threatening, complications associated with the transplant procedure, immunosuppressive regimen, tolerance-inducing regimen, and/or the encapsulation of the islets.

The methods of the invention also include methods of treating or preventing diabetes wherein after the transplantation of transgenic pancreatic tissues or cells, the transplant is repeated. The transplant may be performed twice, three times or more in any one primate. The transplants may be conducted at regular intervals to maintain appropriate insulin levels. The transplant may occur once a year. The transplant may occur twice a year. The transplant may occur three times a year. The transplant may occur more than three times a year. The transplant may occur at various times over multiple years. The parameters of any one transplant, including, but not limited to, surgical procedures, delivery methods, donor tissues and/or cells used, immunosuppressive regimens used and the like, may be different or the same when compared to other transplants performed in the same primate.

In some embodiments, the method reduces the need for administration of anti-inflammatories to the host. In other embodiments, the method reduces the need for administration of anticoagulant to the host. In certain embodiments, the method reduces the need for administration of immunosuppressive agents to the host. In some embodiments, the host is administered an anti-inflammatory agent for less than thirty days, or less than 20 days, or less than 10 days, or less than 5 days, or less than 4 days, or less than 3 days, or less than 2 days, or less than one day after administration of the pancreatic islet cells. In some embodiments, the host is administered an anti-coagulant agent for less than thirty days, or less than 20 days, or less than 10 days, or less than 5 days, or less than 4 days, or less than 3 days, or less than 2 days, or less than one day after administration of the pancreatic islet cells. In some embodiments, the host is administered an immunosuppressive agent for less than thirty days, or less than 20 days, or less than 10 days, or less than 5 days, or less than 4 days, or less than 3 days, or less than 2 days, or less than one day after administration of the pancreatic islet cells.

The recipient (host) may be partially or fully immunosuppressed or not at all at the time of transplant Immunosuppressive agents/drugs that may be used before, during and/or after the time of transplant are any known to one of skill in the art and include, but are not limited to, MMF (mycophenolate mofetil (Cellcept)), ATG (anti-thymocyte globulin), anti-CD154 (CD40L), alemtuzumab (Campath), CTLA4-Ig (Abatacept/Orencia), belatacept (LEA29Y), sirolimus (Rapimune), tacrolimus (Prograf), daclizumab (Zenapax), basiliximab (Simulect), infliximab (Remicade), cyclosporin, deoxyspergualin, soluble complement receptor 1, cobra venom, methylprednisolone, FTY720, everolimus, anti-CD154-Ab, leflunomide, anti-IL-2R-Ab, rapamycin, and human anti-CD154 monoclonal antibody. One or more than one immunosuppressive agents/drugs may be used together or sequentially. One or more than one immunosuppressive agents/drugs may be used for induction therapy or for maintenance therapy. The same or different drugs may be used during the induction and maintenance stages. In one embodiment, daclizumab (Zenapax) is used for induction therapy and tacrolimus (Prograf) and sirolimus (Rapimune) is used for maintenance therapy. In another embodiment, daclizumab (Zenapax) is used for induction therapy and low dose tacrolimus (Prograf) and low dose sirolimus (Rapimune) is used for maintenance therapy. In one embodiment, alemtuzumab (Campath) is used for induction therapy. See Teuteberg et al., Am J Transplantation, 10(2):382-388. 2010; van der Windt et al., 2009, Am. J. Transplantation 9(12):2716-2726. 2009; Shapiro, The Scientist, 20(5):43. 2006; Shapiro et al., N Engl J. Med. 355:1318-1330. 2006 Immunosuppression may also be achieved using non-drug regimens including, but not limited to, whole body irradiation, thymic irradiation, and full and/or partial splenectomy. These techniques may also be used in combination with one or more immunosuppressive drug/agent.

The transgenic pancreatic islet cells may be transplanted using any means known in the art, including, but not limited to, introduction via the recipient organism's portal vein, under the renal capsule, into the sternomastoid muscle, intraperitoneally, in the gastric submucosa, in the testes, or in the spleen (see Rood et al., Cell Transplantation, 15:89-104. 2006; Dufrane and Gianello, Transplantation, 86:753-760. 2008; Hering et al., Nature Medicine, published online 19 Feb. 2006; van der Windt et al., Cell Transplant. 2008; 17(9): 1005-14), and they also may be transplanted in combination with sertoli cells, which have been suggested to provide an immune suppressive effect in islet allografts (Yin et al., 2009 Transplantation. 2009 Aug. 15; 88(3):339-45). In one embodiment, a method of xenotransplantation is provided to transplant the pancreatic cells provided herein into a primate wherein the islets are administered by intraportal infusion. In one embodiment, a method of xenotransplantation is provided to transplant the pancreatic cells provided herein into a primate wherein the islets are administered via the intraperitoneal space, renal subcapsule, renal capsule, omentum, or via pancreatic bed infusion.

The methods of the invention also include methods of xenotransplantation wherein the islets are encapsulated. The islets may be microencapsulated, macroencapsulated or a combination of both. All or some islets may not be encapsulated. The materials used to produce capsules may be any known to one of skill in the art including, but not limited to, nitrocellulose, alginate, acrylonitrile, agarose and polytetrafluoroethylene. The capsule may be permeable or semipermeable.

Sufficient time to allow for engraftment (for example, 1 week, 3 weeks, and the like) is provided and successful engraftment is determined using any technique known to one skilled in the art. These techniques may include, but are not limited to, assessment of donor C-peptide levels, histological studies, intravenous glucose tolerance testing, exogenous insulin requirement testing, arginine stimulation testing, glucagon stimulation testing, testing of IEQ/kg (pancreatic islet equivalents/kg) requirements, testing for persistence of normoglycemia in recipient, testing of immunosuppression requirements, and testing for functionality of transplanted islets (See Rood et al., Cell Transplantation, 15:89-104. 2006; Rood et al., Transplantation, 83:202-210. 2007; Dufrane and Gianello, Transplantation, 86:753-760. 2008; van der Windt et al., 2009, Am. J. Transplantation, 9(12):2716-2726. 2009).

One or more techniques may be used to determine if engraftment is successful. Successful engraftment may refer to relative to no treatment, or in some embodiments, relative to other approaches for transplantation (i.e., engraftment is more successful than when using other methods/tissues for transplantation). In some cases, successful engraftment is determined by assessment of donor C-peptide levels. When porcine animals, tissues, cells are used, in one embodiment, engraftment may be considered successful when porcine C-peptide levels are about between 0.2-1.0 (ng/ml) or, more specifically, about between 0.2-0.65 (ng/ml) (See Cooper and Casu, Xenotransplantation, 16:229-238. 2009; Rood et al, Cell Transplantation, 15:89-104. 2006). In another embodiment, testing of IEQ/kg (pancreatic islet equivalents/kg) requirements is used. In this embodiment, fewer IEQ/kg are required relative to that required using other methods/tissues for transplantation. In some cases, the IEQ requirements may be below approximately 50,000 IEQ/kg of neonatal porcine mass or below approximately 25,000 IEQ/kg of adult porcine mass (Dufrane and Gianello, Transplantation, 86:753-760. 2008). In some cases, the IEQ requirements may be below approximately 100,000 IEQ/kg of adult porcine mass. Achieving blood glucose regulation with lower IEQ/kg levels may be one indication of successful engraftment. In some cases, persistence of normoglycemia in the recipient (host) is a hallmark of successful engraftment. A prolonged decreased (or no) dependence on exogenous insulin for a period of time after the transplant is one indication of successful engraftment. This period of time may be for 3 months, 6 months, 1 year, or greater than 1 year. It may follow a first transplant or may be measured from subsequent transplants. In some cases, successful engraftment is illustrated by a reduced need for immunosuppression. This reduced need for immunosuppression may include the lowering of a dose of one or more immunosuppressive drugs/agents, a decrease in the number of types of immunosuppressive drugs/agents required, a shorter duration of immunnosuppression, and/or lower or no maintenance immunosuppression. In one embodiment, successful engraftment may be assessed by testing for functionality (partial or full) of the transplanted tissue. This may include detecting donor C-peptide (for example, porcine C-peptide) in combination with a greater than 50% reduction in exogenous insulin needs. In another example, functionality of transplanted tissue may be defined as basal or stimulated C-peptide greater than 0.3 ng/dl.

Further direction regarding islet cell transplantation may be found in the following references: Bertuzzi et al., Cur Mol Med, 6(4):369-74. June 2006; Ricordi et al., Diabetes, 35:649. 1986; Korsgren et al., Transplantation, 45:509. 1988; Dufrane et al., Xenotransplantation, 13(3):204-14. May 2006; Toso et al., Cell Transplantation, 9:297. 2000; Cozzi and Bosio, Curr Opin Organ Transplant, 13(2):155-8. April 2008; Bottino and Cooper, Xenotransplantation, 15(2):104-6. March 2008.

A host in need of treatment or prophylaxis of diabetes can be a host identified as having diabetes, pre-diabetes or a diabetic related illness. The host can be suffering from: increased thirst or hunger, dry mouth, frequent urination, unexplained weight loss, fatigue, blurred vision, headaches, loss of consciousness (rare), slow-healing sores or cuts, itching of the skin, frequent yeast infections, recent weight gain, velvety dark skin changes of the neck, armpit and groin, called acanthosis nigricans, numbness and tingling of the hands and feet, decreased vision, impotency. Prediabetes, also known as "impaired glucose tolerance," is a health condition with few symptoms but is almost always present before a person develops the more serious type 2 diabetes. More than 50 million people in the U.S. over age 20 have prediabetes with blood sugar levels that are higher than normal, but are not high enough to be classified as diabetes. To determine prediabetes, one of two blood tests is used—the fasting plasma glucose (FPG) test and the oral glucose tolerance test (OGTT). During the FPG blood test, blood sugar level is measured after an 8 hour fast. In the FPG test, a measurement of 100 mg/dL-125 mg/dL indicates prediabetes and Greater than 126 mg/dL on two or more tests indicates diabetes. During the OGTT test, blood sugar is measured after a fast and then again 2 hours after drinking a beverage containing a large amount of glucose. In the OGTT test, a measurement of 140 mg/dL to 199 mg/dL indicates prediabetes and a measurement of greater than 200 mg/dL indicates diabetes.

EXAMPLES

Example 1

Islet-Specific Expression Vector Construction

The mammalian expression vector pCI-Neo (Promega) sewed as a backdrop for the pancreatic islet-specific expression cassette. This vector was modified by a Cla1 excision of a 1967 base pair (bp) fragment containing the phage f1 region, the SV40enhancer and early promoter, the SV40 minimum origin of replication, and the neomycin phosphotransferase gene. In addition, the CMV immediate-early enhancer/promoter was excised when the insulin-II promoter was inserted into this vector using restriction enzymes BglII and Hind III.

A choice of sequence to serve as the promoter element for the pancreas specific expression vector was made by comparison of two cloned sequences amplified from the proximal sequence upstream of the rat insulin II gene CDS. These amplified products varied in length from 497 bp to 767 bp; the shortest amplified product most closely corresponded to that used previously in the literature. To determine which promoter sequence amplimer was the best choice, the cDNA for GFP was introduced downstream of each promoter sequence and these test vectors were used for transfection of Beta-TC-6 mouse pancreatic insulinoma cells. FACS analysis was performed to test for transgene (GFP) expression in transfected cells. The analysis indicated that the longest amplimer (767 bp) resulted in better expression of GFP; therefore all vectors used to produce islet-specific expression contain this longest promoter element.

The 767 bp region 5' to the rat insulin II gene coding region was amplified by PCR using purified high molecular weight rat DNA as template, PFx DNA polymerase (Invitrogen), and primers:

(SEQ ID NO:1) pins2bgl 5': gacgagatct accaaatcag gaacagaaag agtc (SEQ ID NO:2) pins2hd 3': tatcaagctt acctgcttgc tgatggtttc cgac This fragment serves as promoter in all vectors used to produce pigs and mice with pancreas specific expression of transgenes.

This rat insulin II (rins2) promoter region, as a BglII/HindIII fragment, was inserted into the ClaI-deleted pCI neo vector by digestion with restriction enzymes BglII and Hind III, which at the same time removes the CMV enhancer promoter (765 bp frag) from pCIneo.

The murine PDX-1 gene distal enhancer (483 bp) was amplified by PCR using purified high molecular weight mouse DNA as template, PFx DNA polymerase, and primers:

(SEQ ID NO:3) muPDXbg15': actgagatcttctagagagttcttctgtttgcta (SEQ ID NO:4) muPDXbam3': gctcggatccttaaaggtaaatgaattttatata The murine PDX-1 enhancer was inserted as a Bgl II/BamHI fragment 5' of the rInsII promoter in the BglII restriction site to create the intermediate pInsII vector.

Multiple chicken β-globin insulator fragments were inserted into the vector at locations flanking the enhancer/promoter/transgene site. The chicken β-globin insulator (227 bp) was amplified by PCR using an in-house vector containing the insulator sequence, PFx DNA polymerase, and primers:

```
globins Cla5':
                                    (SEQ ID NO: 5)
attaatcgatgggacagccccccccaaag globins Xba3':
                                    (SEQ ID NO: 6)
atattctagattttccccgtatcccccaggtgt globins Spe5':
                                    (SEQ ID NO: 7)
attaactagtgggacagccccccccaaag globins Cla3':
                                    (SEQ ID NO: 8)
atatatcgattttccccgtatcccccaggtgt
```

ClaI/XbaI insulator fragments and SpeI/ClaI insulator fragments were generated from this amplification and introduced into the ClaI site at the 3' end of the pInsII vector containing the murine PDX-1 enhancer in a 3-fragment ligation. A total of 4 insulator fragments were introduced at this site.

Insulators for the 5' end of the cassette were prepared by excising a pair of insulator fragments from the vector containing the four 3' insulator fragments (above) with a ClaI digest, blunting this ClaI fragment with DNA polymerase I, large (Klenow) fragment, and inserting this blunt-ended fragment into a blunted BglII site in the rInsII vector already containing the promoter, enhancer, and 3' flanking insulators.

This base vector is referred to as pREV788 and was used for all subsequent introductions of transgenes for pancreatic islet-specific expression. The vectors containing the introduced transgenes are shown in FIG. 1. The vectors utilized in the following examples are:

pREV788: The islet-specific vector cassette contains the rat insulin II promoter with flanking chicken β-globin insulators and the murine PDX-1 enhancer. A multiple cloning site (MCS), with an upstream chimeric intron and downstream SV40 pA signal, is provided for transgene insertion and expression.

pREV790: A 1841 bp Xho1/Not1 fragment containing the human TFPI cDNA fused to cDNA coding for domains 3 and 4 of human CD4 and the C-terminal sequence was inserted into the Xho1/Not1-digested vector cassette.

pREV792: A 1637 bp Sal1/Not1 fragment containing the porcine CTLA4 extracellular region cDNA, fused via a flexible linker to the hinge CH2 and CH3 regions of human IgG1, was inserted into the Sal1/Not1-digested vector cassette.

pREV835: A 1609 bp Xho1/Xho1 fragment containing the human CD39 cDNA was inserted into the Xho1-digested vector cassette.

Sequence for pCTLA4-Ig and TFPI are in part derived from sequences described in U.S. Pat. Nos. 7,432,344 and 6,423,316.

These vectors were transfected into two different primary porcine fetal cell lines (see Example 3). Cell line 183-6-6, was isolated from a male fetus that was genotype homozygous GTKO and heterozygous transgenic for CD46. Cell line 227-3 was isolated from a female pig (ear biopsy) that was homozygous GTKO and homozygous transgenic for CD46.

Transgenic mice were produced to test the pancreatic expression vector, with TFPI as the introduced transgene. Subsequently, pigs were produced with demonstrated pancreas expression of CD39 (e.g. pig 320-2), and a fetus was produced (548/A3) and subsequently recloned to produce pigs which had demonstrated pancreas expression of both pCTLA4-Ig and TFPI transgenes (e.g pig 347-3). The pigs embodied in the following examples were all produced on a genetic background that was homozygous GTKO and CD46 transgenic (cell lines used were 183-6-6 or 227-3). Thus the genome of these resulting pigs has three to four genetic modifications relevant to xenotransplantation, with at least one of these modifications resulting in transgene expression specifically in the pancreas for utility in islet transplantation.

Example 2

Production of TFPI Transgenic Mice with Pancreas-Specific Expression Vector pREV790

Zygote stage mouse embryos were obtained from B6C3 F1 females mated to B6C3 F1 males (Harlan Sprague Dawley, Dublin, Va.). The females were superovulated with 7.5 IU PMSG (i.p., Calbiochem, San Diego, Calif.) and 5.0 IU Hcg (i.p., Intervet, Millsboro, Del.) 44 to 48 h later. Zygotes were collected and manipulated by standard methods (Hogan et al., 1994) in FHM (Specialty Media, Lavallette, N.J.). In vitro embryo culture was done in KSOM medium (Specialty Media) at 37° C. with 5.0% $CO^2$ in humidified air. Pronuclear microinjection of the pREV790 construct was performed using methods described previously (Page et al., 1995 Transgenic Res. 4:12-17). Injected embryos were cultured in vitro overnight, at which time they were removed from KSOM and placed into FHM. Viable two-cell embryos were transferred into the oviducts of pseudo pregnant ICR mice (Harlan Sprague Dawley) using known techniques (Hogan et al., Manipulating the Mouse Embryo, $2^{nd}$ edition, 2004) and allowed to deliver their pups naturally. At 21 days of age, pups were weaned, sexed, and identified by toe notching. Tail tip biopsies were collected for genotype analysis.

One-hundred twenty zygotes were microinjected, 87 were cultured overnight, and 76 resulting two-cell embryos were transplanted into pseudo pregnant recipients. Nineteen pups were born of which 4 were screened by PCR and Southern analysis and found to be transgenic for the pREV790 construct (21% transgenic rate). This transgenic rate is within the normal expected range using microinjection techniques.

Example 3

Cell Line Preparation for Nuclear Transfer

Isolation of Cell Lines:

Two cell lines (183-6-6 and 227-3) were used as the genetic background for transfections to add the additional transgenes, and ultimately for nuclear transfer to generate pigs. Both cell lines were produced by breeding of GTKO pigs (Dai et al., (2002) Nature biotechnology 20, 251-255; Phelps et al., Science, (2003) 299:411-414) with ubiquitously expressing hCD46 transgenic pig lines (Loveland et al., Xenotransplantation, 2004, 11:171:183). Both cell lines were confirmed by genotype and phenotype as homozygous GTKO and hCD46 transgenic. The cell lines were prepared for use in NT as follows: A fetal fibroblast cell line was isolated from fetus 183-6-6 at day 36 of gestation. The Fetus was mashed through a 60-mesh metal screen using curved surgical forceps slowly so as not to generate excessive heat. The cell suspension was then pelleted and resuspended in DMEM containing 20% fetal calf serum and Antibiotic-Antimycotic (Invitrogen). Cells were cultured three days, and cryopreserved.

An ear fibroblast cell line was isolated from a 48 day old pig (227-3) from an ear punch. The ear punch was washed with 200 proof ethanol followed by a wash with PBS. Tissue was minced with surgical scissors and cultured for 12 days prior to cryopreservation. Fetus 548/A3 was collected on day 73 of gestation, and pancreatic samples were isolated for expression analysis (Examples 6-7). In addition, fetal cells were isolated (as described above) and banked for later recloning. (Example 4).

Plasmid Fragment Preparation for Transfection:

pREV790 plasmid fragment was prepared for transfection by restriction enzyme digestion with AatII and AhdI (New England Biolabs). pREV792 was prepared by digestion with AseI and AatII (New England Biolabs). The plasmid fragments generated by digestion were separated on a 1% low melt agarose gel (Cambrex) to remove the plasmid backbone. The transgene-containing cassette fragment of interest was excised and incubated twice in 2 volumes of 1× agarase buffer on ice for 15 minutes. After removing the buffer, the gel was melted at 65° C. 10 minutes. After 10 minutes at 42° C., 1 uL Agarase (New England Biolabs) per 100 uL of gel melt and incubated minimum 1 hour at 42° C. One-tenth volume of 3M Sodium Acetate was added to the gel melt and incubated on ice 15 minutes. Centrifugation at 15000 rpm for 15 minutes at 4° C. separates any undigested agarose. Two volumes of 100% ethanol were added to the supernatant and centrifugation was used to pellet the DNA fragment. 70% ethanol was used to wash the pellet before drying at 37° C. The pellet was resuspended in TE.

Transfection, Selection, Harvesting of Colonies for Screening:

Porcine ear fibroblasts from pig 227-3 were transfected with pREV790 (Pdx-rInsII-hTFPI), pREV792 (Pdx-rInsII-pCTLA4-Ig) and pREV828 (a Puromycin selectable marker gene vector). Approximately 5 million cells were co-electroporated with 3 μg of each of the transgene vectors and 0.5 μg of the selectable marker vector. Forty-eight hours post transfection, transfected cells were selected with the addition of 0.5 mg/ml of the antibiotic Puromycin (InvivoGen, San Diego, Calif.) in 20×10 cm dishes at a density of approximately 25,000 cells per dish. Media was changed 72 hours post initiation of puromycin selection. Colonies were harvested 7 days post initiation of selection. 70 puromycin-resistant colonies were harvested and cultured further for 3 days. Forty-five of 70 colonies grew and were split into two samples: one for PCR analysis and one for expansion. PCR analysis for both pREV790 and pREV792 was performed as described in Example 5. Thirty-seven double-PCR positive colonies were pooled and cryopreserved for future us in nuclear transfer.

Similar procedures were used for co-transfection, selection and harvesting of colonies using the pREV835 (Pdx-rInsII-CD39) vector, in combination with pREV828 and pREV792, except in this case cell line 183-6-6 was used for transfection.

Example 4

Production of Multi-Transgenic Pigs by Nuclear Transfer (NT)

Figure 7:
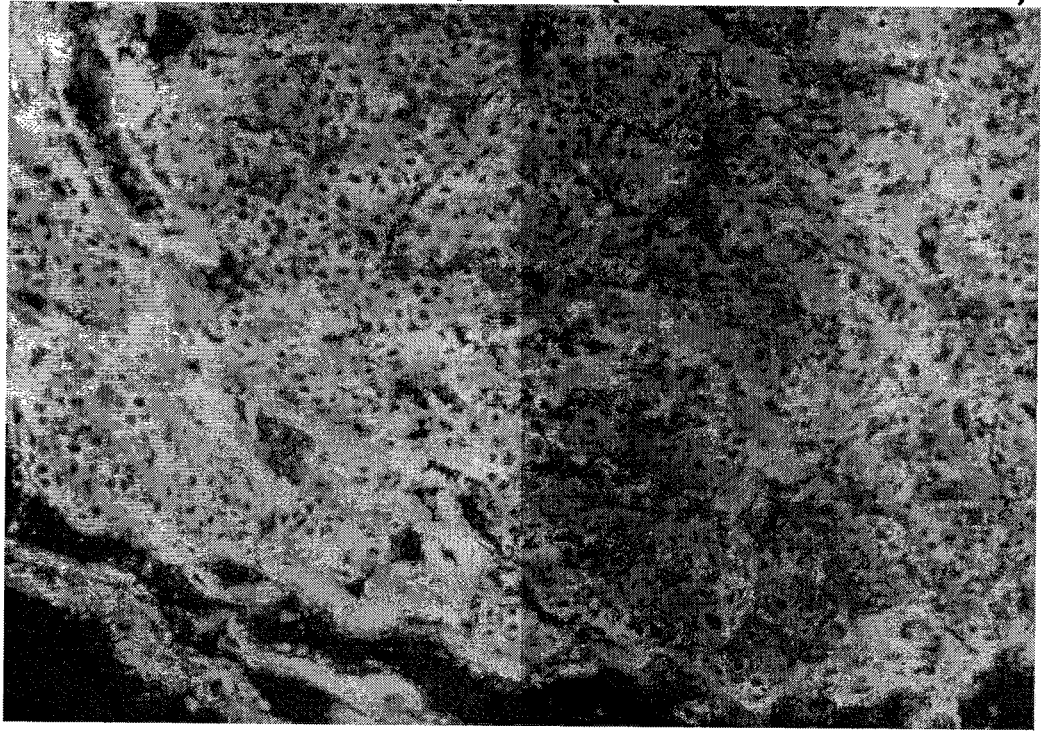
FIG. 7 is images of pancreas from piglet 342-3, a reclone of 548/A3 stained with FITC-labeled anti-human CD46, showing high expression of CD46.

Various methods can be used to produce the multi-transgenic pigs of the current invention. The following is one example in which donor cells used (line 227-3 and line 183-6-6) were the genetic background homozygous GTKO (lacked any function αGT) and were also transgenic for CD46 (and expressed CD46 in pancreas; FIG. 7). Donor cells were transfected, selected and screened positive for the pREV790, pREV792, and/or pREV835 vectors, as described in Example 3, prior to being used for NT. In some cases, multiple colonies of transfected and selected cells, all screening positive for the transgene(s), were pooled together prior to their use in NT.

Donor cells (fetal or adult fibroblast cells) for NT were cultured in Dulbecco's Modified Eagle Medium (DMEM, Gibco, cat#11995-065) supplemented with 10-20% fetal calf serum and 0-4 ng/ml basic fibroblast growth factor, in a humidified incubator at 5% O2, 5% CO2 balanced with nitrogen at 37° C. For culture, cells were seeded 3-7 days prior to the nuclear transfer procedure, at an appropriate dilution such that the cells would reach confluency 24-48 hours prior to nuclear transfer. On the day of nuclear transfer, donor cells were harvested about 30-45 minutes before use in embryo reconstruction by using Trypsin-EDTA (Gibco, cat#25300-054), making a single cell suspension in suitable holding medium (e.g. Hepes buffered M199, Gibco cat #12350-039).

NT procedures were performed on in vitro matured oocytes (Desoto Biosciences, Christiansburg, Va.) using methods well known in the art (see, e.g., Polejaeva, et al., (2000) Nature 407, 86-90, Dai et al., (2002) Nature biotechnology 20, 251-255, Campbell et al., (2007) Theriogenology 68 Suppl 1, S214-231, Vatja et al., (2007) Reprod Fertil Dev 19, 403-423). Electrical fusion and activation of reconstructed oocytes was performed using an ECM2001 Electrocell Manipulator (BTX Inc., San Diego). Fused and activated nuclear transfer embryos were held in culture in phosphate buffered NCSU-23 medium (J Rprod Fertil Suppl. 1993; 48:61-73) for 1-4 h at 38.5° C., and then transferred to the oviduct of an estrus-synchronized recipient gilt. Crossbred gilts (large white/Duroc/Landrace) (280-400 lbs) were synchronized as recipient animals by oral administration of 18-20 mg Matrix (Altrenogest, Hoechst, Warren, N.J.) mixed into their feed. Matrix was fed for 14 consecutive days. Human Chorionic Gonadotropin (hCG, 1000 units; Intervet America, Millsboro, Del.) was administered intramuscularly 105 h after the last Regu-Mate treatment. Embryo transfers were performed by mid-ventral laparotomy 22-26 h after the hCG injection. Pregnant Mare Serum Gonadotropin (PMSG, 1000 IU) and hCG (500 IU) we used on day 10 and 13 post transfer for maintenance of pregnancy. Pregnancy was confirmed via ultrasonography 28 days post-transfer. Pregnancies were monitored thereafter on a weekly basis. All piglets were born via natural parturition.

Nuclear transfer using 183-6-6 cells which were puromycin selected and screened positive for the pREV792 and pREV835 transgenes resulted in three litters of piglets born to date; some piglets were genotypic positive for both the pREV792 and pREV835 transgenes. One of these piglets, #320-2, was used for phenotypic analysis (see Example 7).

Fibroblasts isolated from piglet 320-2 were also subsequently used for nuclear transfer (recloning) and have produced litters and live offspring.

Nuclear transfer using 227-3 cells which were puromycin selected and screened positive for the pREV790 and pREV792 transgenes resulted in the production of fetus 548/A3, which was genotyped positive for both the pREV790 and pREV792 transgenes as well as the GTKO and CD46 genetic modifications from the parent cell line. Cells isolated from fetus 548/A3 were used for recloning and have produced seven litters to date (see Table 1). Piglet 347-3, from one lifter, was used for phenotypic analysis in Examples 6-7. All of these recloned piglets were confirmed to have the same genotype as the 548/A3 fetus, i.e. they were transgenic for the pREV790 (TFPI) and pREV792 (pCTLA4-Ig) transgenes (pancreas specific expression) and additionally were CD46 transgenic and GTKO (due to the genetic background of the cell line used for transfection; 227-3). To our knowledge, this is the first time pigs have been produced comprising more than three genetic modifications.

TABLE 1

Litters of piglets recloned from fetus 548/A3.

| Litter ID Number | Piglets Born (#) | Viable Piglets*(#) |
|---|---|---|
| 342 | 3 | 1 |
| 346 | 2 | 1 |
| 347 | 5 | 5 |
| 367 | 2 | 2 |
| 371 | 2 | 2 |
| 375 | 2 | 2 |
| 384 | 2 | 2 |
| TOTALS | 18 | 15 |

*Viable Piglets are piglets born alive and viable for at least 24 hours. Some piglets were euthanized at various ages for analysis of transgene expression or for other research studies. Two of these animals are currently being raised for breeding.

Example 5

Genotyping of Cells and Transgenic Animals by PCR and Southern Blot Analysis

Genotype Analysis:

Genomic DNA was extracted from transfected cells, and blood or tissue samples from each mouse or piglet to be tested. In brief, tissue samples were lysed overnight at 60° C. in a shaking incubator with approximately 1 ml lysis solution (50 mM Tris pH8.0, 0.15 M NaCl, 0.01 M EDTA, 1% SDS, 25% Sodium perchlorate and 1% of β-Mercaptoethanol and Proteinase K) per 175 mg tissue. DNA was precipitated with isopropyl alcohol following phenol/chloroform extraction. Resolubilized DNA was treated with RNase (1 mg/ml)+ RNase T1 (1000 U/μl) at 37° C. for 1 hour, with proteinase K (20 mg/ml) at 55° C. for 1 hour, extracted with phenol/chloroform, precipitated and resuspended in Tris Ethylenediaminetetraacetic acid (EDTA). DNA was isolated from whole blood samples using a DNA isolation kit for mammalian blood (Roche Diagnostics Indianapolis, Ind.).

For Southern blot analysis, about 10 μg of DNA was digested with the appropriate restriction enzyme (detail below) and separated on a 1% agarose gel. Following electrophoresis, the DNA was transferred to a nylon membrane and probed with a 3'-end digoxigenin-labeled probe (probe sequence below). Bands were detected using a chemiluminescent substrate system (Roche Diagnostics, Indianapolis, Ind.).

pREV790-TFPI

The presence of integrated pREV790 construct was determined by PCR using primers 790.5 L and 790.5 R which target a 1000 bp fragment extending from the rat insulin II promoter into the 5' region of the TFPI coding sequence.

```
790.5L:
                                        (SEQ ID NO: 9)
         agcaaagtccaggggtcag 790.5R:
                                       (SEQ ID NO: 10)
         gaaatctggcttttcttgttgc
```

The presence of integrated pREV790 construct was confirmed by Southern blot analysis using a BamHI digest and probing with probe TFPI5'/3'.

```
TFPI5'/3' probe sequence:
                                       (SEQ ID NO: 11)
GGATTGTGTCGTGCCAATGAGAACAGATTCTACTACAATTCAGTCATTG

GGAAATGCCGCCCATTTAAGTACAGTGGATGTGGGGGAAATGAAAACAA

TTTTACTTCCAAACAAGAATGTCTGAGGGCATGTAAAAAAGGTTTCATC

CAAAGAATATCAAAAGGAGGCCTAATTAAAACCAAAAGAAAAAGAAAGA

AGCAGAGAGTGAAAATAGCATATGAAGAAATTTTTGTTAAAAATATcTG cAgGAACCAGAAGAAGGTGGAaTTCAAAATAGACATCGTGGTGCTAGCT

TTCCAGAAGGCCTCCAGCATAGTCTATAAGAAAGAGGGGGAACAGGTGG

AGTTCTCCTTCCCACTCGCCTTTACAGTTGAAAAGCTGACGGGCAGTGG

CGAGCTGTGGTGGCAGGCGGAGAGGGCTTCCTCCTCCAAGTCTTGGATC

ACCTTTGACCTGAAGAACAAGGAAGTGTCTGTAAAACGGGTTACCCAGG

ACCCTAAGCTCCAGATGGGCAAGAA
``` pREV792-pCTLA4-Ig

The presence of integrated pREV792 construct was determined by PCR using primers (792.s and 792.a) targeting a 473 bp fragment extending from the rat insulin II promoter into the 5' region of the CTLA4 coding sequence. The sequence of these primers was:

```
792.s:
                                       (SEQ ID NO: 12)
         cgctgtgggctcttctcttacat 792.a:
                                       (SEQ ID NO: 13)
         gagcaagccatggctaagctta
```

The presence of integrated pREV792 construct was confirmed by Southern blot analysis using a BamHI digest and probing with probe 792.s1792/a2265.

```
792s1792/a2265 probe seq:
                                       (SEQ ID NO: 14)
CGCTGTGGGCTCTTCTCTTACATGTACCTTTTGCTAGCCTCAACCCTGA CTATCTTCCAGGTCATTGTTCCAACaagctTATTGCGGTAGTTTATCA

CAGTTAAATTGCTAACGCAGTCAGTGCTTCTGACACAACAGTCTCGAAC

TTAAGCTGCAGTGACTCTCTTAAGGTAGCCTTGCAGAAGTTGGTCGTGA

GGCACTGGGCAGGTAAGTATCAAGGTTACAAGACAGGTTTAAGGAGACC
```

```
-continued
AATAGAAACTGGGCTTGTCGAGACAGAGAAGACTCTTGCGTTTCTGATA

GGCACCTATTGGTCTTACTGACATCCACTTTGCCTTTCTCTCCACAGGT

GTCCACTCCCAGTTCAATTACAGCTCTTAAGGCTAGAGTACTTAATACG

ACTCACTATAGGCTAGCCTCGAGAATTCACGCGTGGTACCTCTAGAgtc gacGGTATCGATAAGCTTAGCCATGGCTTGCTC
``` pRE'V835-CD39

The presence of integrated pREV835 construct was determined by PCR using primers CD39R3 and CD39L3 which targets a 584 bp fragment within the CD39 coding region.

```
CD39R3:
                                             (SEQ ID NO: 15)
CATAGAGGCGAAATTGCAGAG

CD39L3:
                                             (SEQ ID NO: 16)
AGTATGGGATTGTGCTGGATG
```

The presence of integrated pREV835 construct was confirmed by Southern blot analysis using a Sad digest and probing with probe CD39L3/R3.

```
CD39 L3/R3 probe sequence:
                                             (SEQ ID NO: 17)
AGTATGGGATTGTGCTGGATGCGGGTTCTTCTCACACAAGTTTATACAT

CTATAAGTGGCCAGCAGAAAAGGAGAATGACACAGGCGTGGTGCATCAA

GTAGAAGAATGCAGGGTTAAAGGTCCTGGAATCTCAAAATTTGTTCAGA

AAGTAAATGAAATAGGCATTTACCTGACTGATTGCATGGAAAGAGCTAG

GGAAGTGATTCCAAGGTCCCAGCACCAAGAGACACCCGTTTACCTGGGA

GCCACGGCAGGCATGCGGTTGCTCAGGATGGAAAGTGAAGAGTTGGCAG

ACAGGGTTCTGGATGTGGTGGAGAGGAGCCTCAGCAACTACCCCTTTGA

CTTCCAGGGTGCCAGGATCATTACTGGCCAAGAGGAAGGTGCCTATGGC

TGGATTACTATCAACTATCTGCTGGGCAAATTCAGTCAGAAAACAAGGT

GGTTCAGCATAGTCCCATATGAAACCAATAATCAGGAAACCTTTGGAGC

TTTGGACCTTGGGGGAGCCTCTACACAAGTCACTTTTGTACCCCAAAAC

CAGACTATCGAGTCCCAGATAATGCTCTGCAATTTCGCCTCTATG
```

Example 6

Phenotypic Analysis (pCTLA4-Ig) of Tissues from Transgenic Pigs Western Blot for pCTLA4-Ig Expression Tissue and cell lysates were prepared by homogenization in the presence of protease inhibitors (Thermo Scientific, Rockford, Ill.) followed by the addition of SDS (1% final concentration) and centrifugation to remove residual cellular debris. Protein concentration was determined with a bicinchoninic acid (BCA) protein assay kit (Pierce, Rockford, Ill.). Heat-denatured and β-mercaptoethanol-reduced samples (10-20~g protein) were fractionated on 4-12% BisTris SDS gradient gels (Invitrogen, Carlsbad, Calif.). Recombinant human CTLA4-Ig/Fc (R&D Systems, Minneapolis, Minn.) was used as a standard control protein. Following electrophoresis, proteins were transferred to a nitrocellulose membrane, stained with Memcode Protein Stain (Thermo Scientific) for total protein visualization, and blocked with casein-blocking buffer (Sigma-Aldrich., St. Louis, Mo.). The blocked membrane was incubated in rabbit anti-human IgG1-horseradish peroxidase (HRP) (The Binding Site, San Diego, Calif.), which recognizes the human IgG1 heavy chain region of pCTLA4-Ig. Immunoreactive bands were detected with Super Signal West Pico Chemiluminescent Substrate (Thermo Scientific) and photographic imaging.

Figure 2:
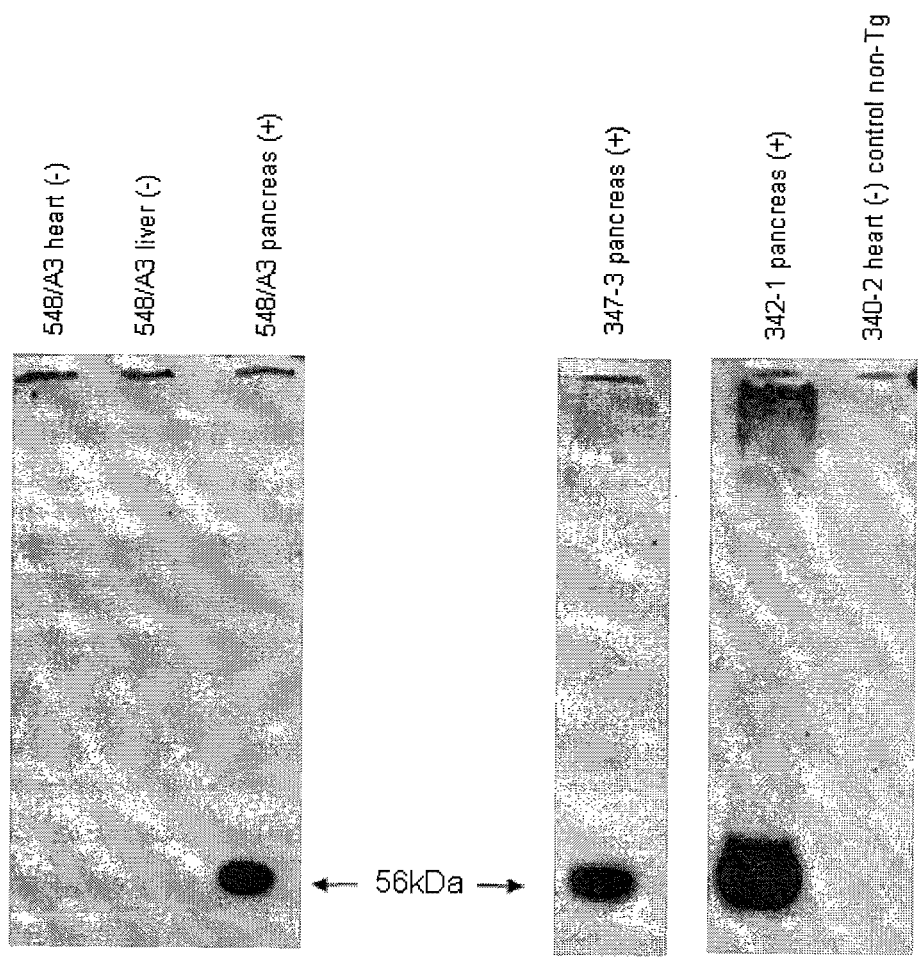
FIG. 2 shows images of pCTLA4-Ig protein expression in transgenic pig organ lysates as detected by Western blot analysis under reduced and denaturing conditions. Bands were detected with antibody specific for the Ig portion of the fusion protein. 347-3 and 342-1 are reclones of fetus 548/A3 and 340-2 is a non-transgenic animal (used as a negative control).

Fetus 548/A3, and a recloned piglet from 548/A3 cells (piglet 347-3) showed expression of the 56 kDa pCTLA4-Ig protein by Western, specifically in pancreas. (FIG. 2.)

Example 7

Phenotypic Analysis of Animals Expressing Transgenes in Pancreas Histology and Immunofluorescence Mouse or pig Pancreata were removed and were either fixed in 10% formalin or frozen down in blocks of OCT (Electron Microscopy Sciences, Hatfield, Pa.). Formalin fixed tissues were blocked in paraffin and cut at 5 μm for staining with Hematoxylin and Eosin (H+E) staining. H and E staining was performed using standard procedures. Frozen sections were cut at 5 μm on a cryostat and were stained with rabbit anti-human TFPI (polyclonal, American Diagnostica, Stamford, Conn., #4901), sheep anti-human IgG1 (polyclonal, The Binding Site, Birmingham, UK, #AUOO6), mouse anti-human CD46 (clone O.N. 137, mIgG2a, U.S. Biological, Swampscott, Mass.), mouse anti-human CD39 (clone BU6I, mIgG1, Ancell, Bayport, Minn.) or mouse anti-rat insulin/proinsulin (clone D3E7, mIgG1, Serotec, Oxford, UK). Isotype controls were run for rabbit IgG (Jackson ImmunoResearch, West Grove, Pa.), sheep IgG (Jackson), mouse IgG2a (clone MRC OX-34, Serotec) and mouse IgG1 (clone MOPC-31C, BD Pharmingen, San Jose, Calif.), respectively. Immunofluorescent (IF) staining was performed using a 3-step procedure. Frozen sections were dried and fixed in cold acetone (Sigma, St. Louis, Mo.), followed by avidin-biotin blocking (Invitrogen, Carlsbad, Calif.). Secondary Ab host species serum blocking steps were also included (10% Donkey serum, Jackson). Primary Abs were diluted in PBS and incubations were performed for 1 h at room temperature in a humidified chamber. The secondary Ab used was biotinylated donkey anti-(rabbit, sheep, or mouse) IgG for 45 mm and the tertiary Ab used was fluorescein-conjugated strep avidin for 30 mm (Jackson). Slides were washed in PBS between steps, were cover slipped using 22×30 mm coverslips (VWR, West Chester, Pa.) and were preserved using Slowfade with DAPI (Invitrogen). Representative histological and IF pictures were taken using an Olympus DP71 camera on a Provis microscope, and analyzed using DP controller software (Olympus, Center Valley, Pa.) with a magnification of 200×.

Figure 3:
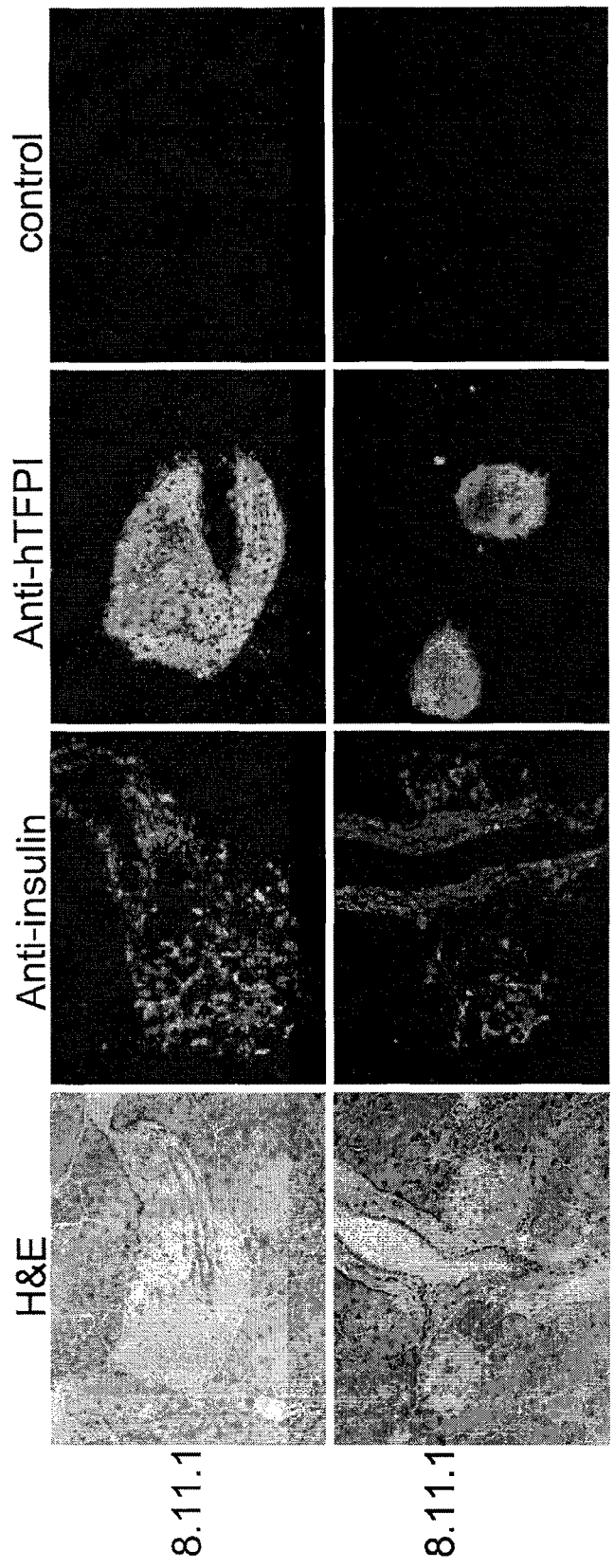
FIG. 3 is images of cells stained with FITC-labeled anti-human TFPI antibody showing high levels of hTFPI observed in adult transgenic mouse pancreas, with localized expression in islets. H&E staining shows representative islet morphology.
Figure 4:
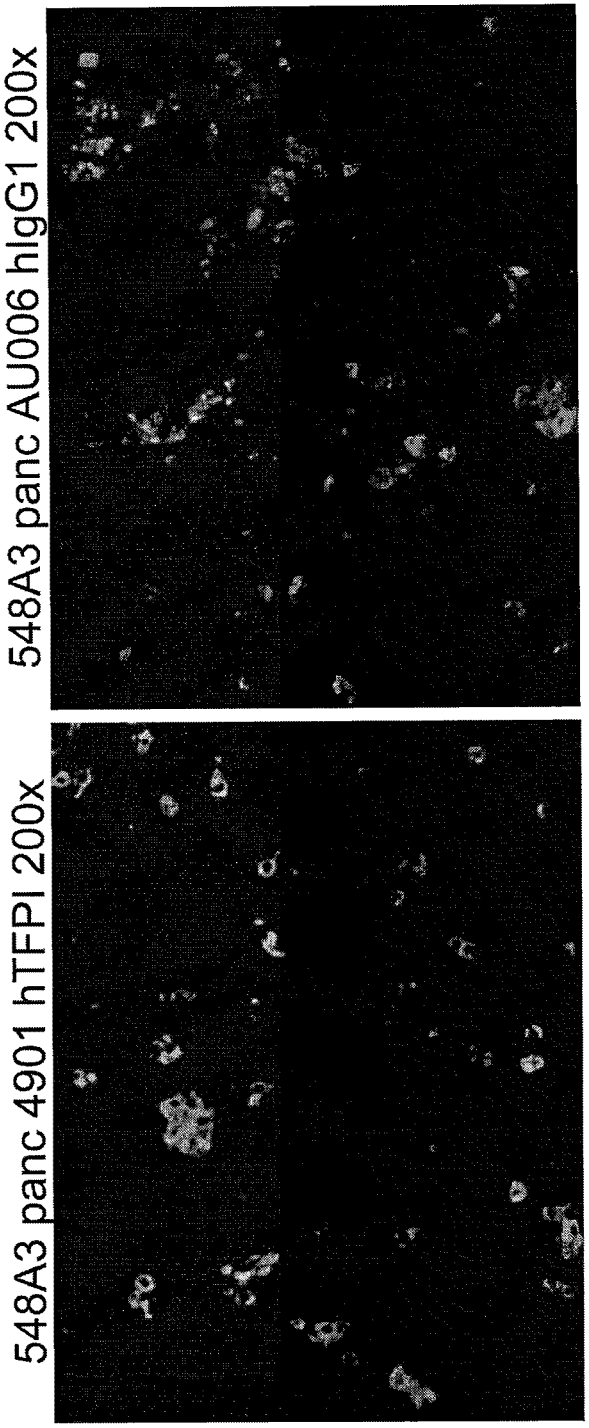
FIG. 4 is images of fetal pancreas from 548/A3 stained with FITC-labeled anti-human TFPI Ab and FITC-labeled anti-human IgG1 (which binds to the human Ig portion of the pCTLA4-Ig), showing expression of TFPI and pCTLA4-Ig.
Figure 5:
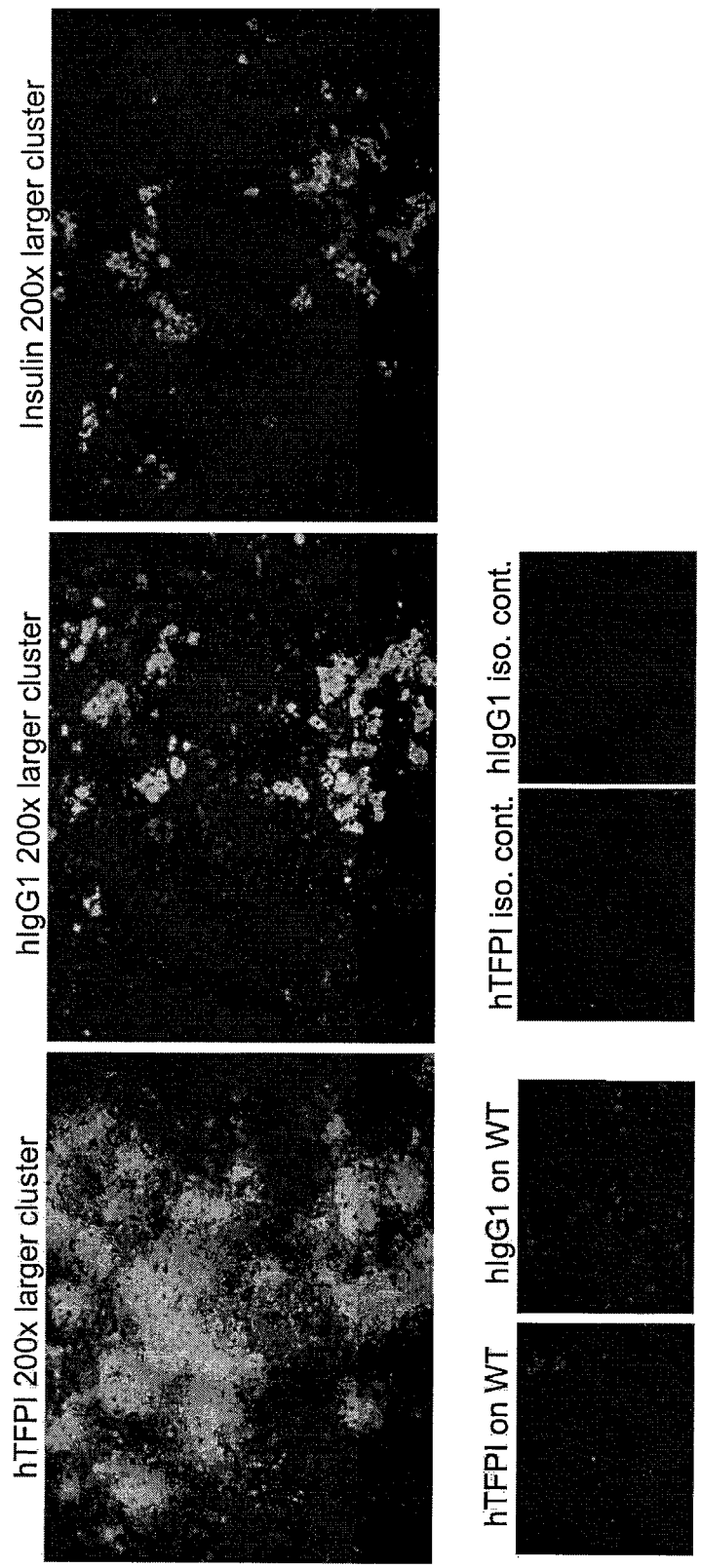
FIG. 5 is images of pancreas from 2.5 month old piglet 347-3 (a redone of 548/A3), stained with FITC-labeled anti-human TFPI Ab, and FITC-labeled anti-human IgG1 (which binds to the human Ig portion of the pCTLA4-Ig), showing expression of both the TFPI and pCTLA4-Ig transgenes. Staining for insulin shows a similar pattern to that of the transgenes. Wild type pig and isotype controls are also shown.
Figure 6:
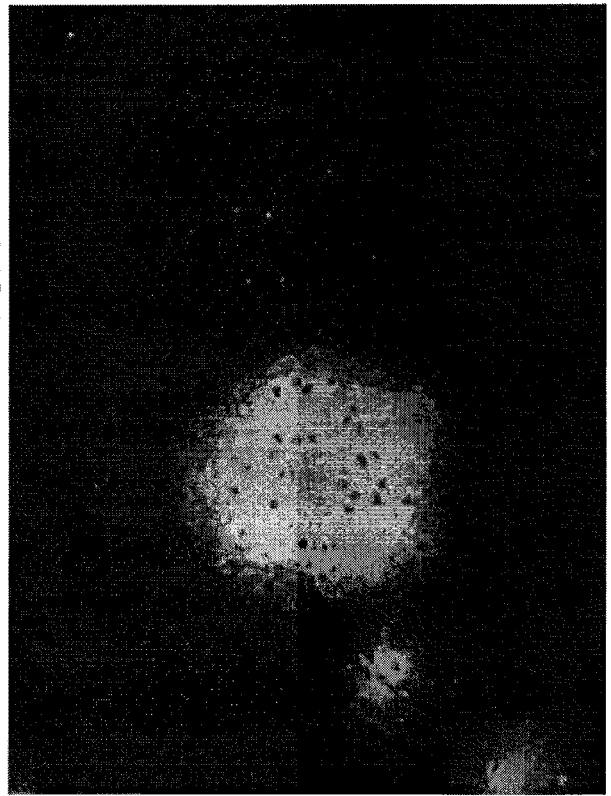
FIG. 6 is images of pancreas from piglet 320-2, stained with FITC-labeled anti-human CD39, showing high expression of CD39. Staining for insulin is also shown.
Figure 6:
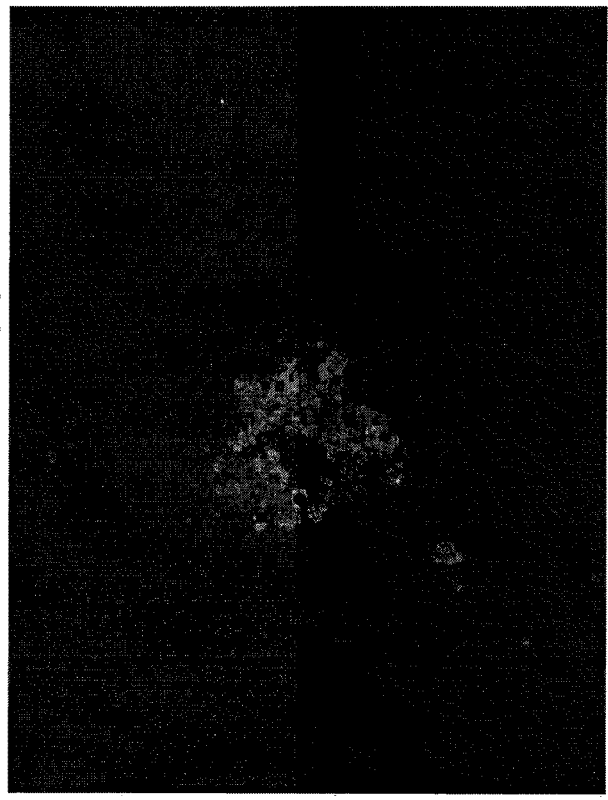

Results:

pREV790 (TFPI) Transgenic Mice:

One year old mice had very well clustered islets, as shown in the representative H+E histology. These mice expressed hTFPI in an islet-specific manner, staining was localized in a similar manner to that of insulin (FIG. 3). hTFPI staining was more intense than insulin, indicating efficient islet-specific expression using the presently described system.

pREV790/pREV792 Transgenic Pigs:

Fetus 548/A3 was characterized by histology at 73 days of gestation (FIG. 4). Piglet 347-3 (a reclone of 548/A3) was characterized at about 2.5 months of age (FIG. 5). Beta cells are scattered and diffuse in a fetal pancreata, which can be seen in the representative photos. Staining patterns for hTFPI and pCTLA4-Ig (hIgG1 Ab) were similar to insulin. Staining was more intense for hTFPI and pCTLA4-Ig than insulin. Piglet 347-3, at 2.5 months of age, had more developed islet clusters, and showed strong staining therein. The islet-specific expression in piglet 347-3 was most intense for hTFPI, somewhat less intense for pCTLA-4-Ig, and less intense for insulin.

pREV835 (CD39) Transgenic Pigs:

Piglet 320-2, at ~3.5 months of age, had fully developed islet clusters, and showed strong staining for CD39 therein. The islet-specific expression in 320-2 for hCD39 was more intense than for insulin, as shown in previous mouse and pig examples. (FIG. 6).

Example 8

Islet Isolation and In Vitro Coagulation Assays of Transgenic Mouse and Pig Islets Porcine and murine pancreatic islets can be isolated, cultured and tested in vitro for coagulation (clotting time), using laboratory protocols known in the art, examples of which are provided here.

Solutions for Islet Isolation and Culture:

---

25% Ficoll Stock solution:

33.3 g Ficoll 400, Type 400, Sigma #F-4375
100 ml HBSS/Hepes
Mix together with stirring and low heat until Ficoll goes into into soln. Sterile filter. Store at 40° C. Make gradients from the 25% soln.

| For 50 ml: | 25% Ficoll | HBSS/Hepes |
|---|---|---|
| 23% soln = | 46 ml | 4 ml |
| 20.5% soln = | 41 ml | 9 ml |
| 11% soln = | 22 ml | 28 ml |

Mix together thoroughly. Store at 40° C.
HBSS/Hepes:

500 ml HBSS with calcium and magnesium
  10 ml Hepes 1 M
Mix together thoroughly. Store at 40° C.
HBSS/BSA:

500 ml HBSS with calcium and magnesium
  10 ml Hepes 1 M
  2.5 g BSA Fraction V
Filter sterilize after adding BSA. Mix together thoroughly. Store at 40° C.
Collagenase:

1.95 mg Collagenase Type V Sigma #C-9263
  1 ml HBSS/Hepes
Mix gently. Too much agitation will destroy enzyme action. Keep at 40° C. Soln. is best used fresh but may be used for up to 3 days if kept at 40° C. Soln. gets weaker as it ages and may also be frozen but activity is less after thawing.
Murine Islet Culture Media:

500 ml RPMI 1640
  50 ml Fetal bovine serum (heat inactivated)
  10 ml Hepes 1 M
  5 ml Penicillin/Streptomycin (10,000 U/10,000 mg/ml)
  5 ml L-glutamine (200 mM)
500 ul 2-Mercapto-ethanol 50 mM (stock: 0.2 ml in 55 ml PBS)
Filter sterilize and store at 40° C.

---

Mouse Islet Isolation Protocol:

Sacrifice mouse immediately before pancreas is harvested. Carry out the harvest and isolation procedure under sterile conditions in a flow hood. Perform a laparotomy and pull the skin and body wall back toward the head. The liver will be reflected back against the diaphragm. Locate the common bile and follow to the juncture with the intestine. Place a clamp around the duodenum and over the end of the bile duct to prohibit flow from the bile duct into the intestine.

Fill a 3 ml or 5 ml syringe with cold collagenase soln. and attach a 30 G needle. Bend the needle about half way down the shaft to form a 90 degree angle. Insert the needle into the bile duct, close to the liver with the needle pointed toward the intestine. Slide the needle into the bile duct as far as possible without further damaging the duct (no other punctures) Inject the collagenase into the pancreas until it is fully distended. Inject only a little at first making sure it is not leaking into the intestine. If it is, readjust the clamp. Depending on the size of the animal, the inflation may take 2-5 ml collagenase. After pancreas inflation, remove needle and clamp. The pancreas is removed by tearing and cutting away from the attached tissue and ducts. For maximum yield, remove the entire pancreas. Wash the excised pancreas in cold collagenase soln, then placed in a 25 cm2 flask and kept on ice until all other pancreata are harvested. No more than 4 pancreata are placed in one flask. Place an additional 1-2 ml in the flask before incubation. Incubate the flask at 370 C. for 18-20 minutes without shaking.

After incubation, shake the flask sharply for about 10 seconds or until the tissue is homogenous. Stop the action of the enzyme by adding 10 ml cold HBSS-BSA to the flask. Replace the cap and shake the flask again sharply for 2-3 more seconds. Pour the tissue slurry into a 50 ml conical tube and fill to 50 ml with HBSS-BSA. Mix, then let gravity settle for 5 minutes. This is done to remove the fine particles of tissue that are not islets. The islets are large and will fall to the bottom without centrifugation. Remove the supernatant without disturbing the loosely settled pellet. Mix the pellet by pipetting or shaking and wash again. Repeat washing step 2-5 times until the supernatant is relatively clear. The amount of washing depends on the size of tissue used. Chunks of undigested tissue may be removed by passing the tissue through a wire 20 mesh screen during the second or third wash.

After the last wash, resuspend the pellet at the rate of 5 ml HBSS-BSA per pancreas. The digested tissue is divided and placed into 17×100 mm (14 ml) round bottom polystyrene tubes. No more than 2 pancreata are put into a tube. Gently centrifuge the tubes at 1000 RPM for 1 minute to pellet the tissue. Remove as much of the supernatant as possible from the pellet so as not to dilute the Ficoll gradient. Add 4 ml of the 25% Ficoll soln to the tube and resuspend the tissue by vortexing for 5-10 seconds. Overlay the remaining Ficoll gradients (2 ml of each) starting with 23%, 20.5% and finally 11%. Do not disturb or mix the layers or interfaces. Centrifuge tubes at 1800 RPM for 10 minutes.

After centrifugation, the islets are mostly at the interfaces between the 11 & 20.5% layers and between 20.5 & 23%. Take all the layers and interfaces separately and put them into 15 ml conical tubes. Examine every layer for islets before discarding. Wash the layers with HBSS-BSA once. Centrifuge for 1 minute at 1000 RPM. Remove supernatant by pipet. Wash once more in complete media and let gravity settle for 3-5 minutes. Remove supernatant by pipet. Do not disturb the loose pellet. Collect what is left in the tube and place in a 60 mm non-tissue culture sterile Petri dish. Islets are now ready to hand-pick and count.

Pig Pancreas Digestion with Collagenase:

Prepare the collagenase (Liberase PI or Collagenase P, Roche). Prepare a solution of HBSS with 1 mg/collagenase/ml. Keep on ice until ready to use. Prior to use it warm to 24° C. For the entire pancreas of an adult pig make up 500 ml of solution.

1. On a sterile bucket on ice, clean the pancreas from connective tissue, fat, blood.

2. Take the organ out of ice.
3. Locate the pancreatic duct (if using the entire pancreas) then inject collagenase through the duct. Alternatively, for partial organ samples or if the duct cannot be located, inject collagenase directly in the parenchyma.
4. Injection can go on for up to 5 minutes.
5. Cut the organ into pieces (½ inch each) and put into a beaker with more pre-warmed collagenase (enough to cover the entire piece/s).
6. Place in a 37° C. waterbath and continue to shake manually.
7. After a few minutes the tissue will start to break up. The entire piece may not digest. Avoid overdigestion of the cells that are released, therefore after 10 minutes of shaking, if the solution is getting cloudy, begin to recover the free cells with a pipette and transfer the cells to a bottle or beaker (on ice) with abundant cold RPMI solution containing serum (5%).
8. Continue the warm digestion until enough cells are collected, but don't expose the tissue for longer than 30 minutes to the warm collagenase.
9. Wash the cells in cold RPMI+ serum several times to remove the collagenase.
10. Centrifuge at 1000 RPM for 3 minutes.
11. To obtain isolated islets, run a ficoll gradient.
12. For small amounts of tissue pellet, use 50 ml conical tubes.
13. Make density gradients of: stock 1.132, layers 1.108, 1.096, 1.037.
14. Load 2 ml of pellet dispersed in 10 ml of stock Ficoll on the bottom. On top 8 ml of 1.108, 8 ml of 1.096. 8 ml of 1.037, and 5 ml of HBSS.
15. Centrifuge 20 minutes at 800 g or 2000 rpm.
16. The islets should be at the second and third interface, but check other layers to be sure.
17. Wash out ficoll very well (at least 3 washes for 3 minutes at 1200 rpm, with RPMI+ serum), then culture or fix the cells as needed.

Protocol for In Vitro Coagulation (Clotting Time) Assay:
Materials
    CMRL-1066 medium (Gibco/Invitrogen, Carlsbad, Calif.) at 37 C
    Incubator shaker at 37 C
    Polysyterene untreated 24 well plates
    Pipettes
    1 mL syringes
    Vacutainer set: needle, rubber band,
    Alcohol swaps
    Band aid
    Container for trash
    Timer
Method
    Plate 100 handpicked islets in 200 uL CMRL medium at 37 C per well
    Plate 200 uL CMRL medium at 37 C in control wells with blood only
    Add 200 uL freshly drawn human blood to each well.
    Mix gently by shaking the plate and place plate in incubator shaker
    Observe the experiment for coagulation times Islets were isolated using methods such as those detailed above. Normal wild-type (WT) mouse or pig islets were used as controls. Islets were also prepared from a TFPI-transgenic mouse line (pREV790; see Example 2). The TFPI transgenic pig islets were obtained from the 548/A3 pig line described in Example 4. Islets were mixed with freshly isolated human blood and coagulation time was determined for clot formation. The in vitro coagulation times (in minutes) for transgenic mouse and pig islets exposed to human blood (two separate experiments), are shown in Table 2 below:

| Sample | Experiment One | Experiment Two |
|---|---|---|
| Control (human blood-no islets) | 28.27 | >30.00 |
|  | Mouse (pREV790) | Pig (pREV790/pREV792)* |
| Wild Type Islets | 8.05 | 4.30 |
| Transgenic Islets | 10.24 | 6.12 |

*The pig sampled was also GTKO and CD46 transgenic.

Expression of the transgenes in islets lead to a 33% increase in clotting time in mouse islets, and a 38% increase in clotting time in pig islets.

Example 9

Determination of In Vivo Functionality of a Transgenic Porcine Islet Xenograft in Non-Human Primate (NHP) Transplantation Induction of Diabetes and Immunosuppression in NHP:
In a non-human primate model, diabetes can be chemically induced using a recently-developed streptozotocin protocol as adapted for cynomolgous monkeys, and diabetic state and donor islet survival/function can be monitored using insulin and primate-specific and porcine-specific C-peptide assays (Rood et al. 2006, Casu et al 2008, Bottino et al. 2009).

A co-stimulatory blockade drug, human CTLA4Ig, with similar activity as human anti-CD 154 mAB, can be used in combination with ATG induction therapy, and maintenance therapy with MMF. CTLA4-Ig is currently a potential alternative to CD 154 mAB, that has already been used by one group for pig-to-nonhuman primate islet Tx (Cardona et al., 2006). This CTLA4Ig (Orencia) can be administered at 12.5-25 mg/kg i.v. at the same time intervals as anti-CD 154 mAb (days −1, 0, 4, 7, 10, 14, 19, and weekly, to maintain a trough level >300 ng/ml) to STZ-induced diabetic monkeys. This dosing regimen, in combination with ATG and MMF, was demonstrated, in preliminary studies, to be sufficient to prevent sensitization in baboons that received a GTKO pig artery graft (Ezzelarab et al, manuscript in preparation).

In summary, immunosuppression of NHP for islet transplantation can be as follows:
Induction:
    Anti-thymocyte globulin (ATG) 1-10 mg/kg i.v.×2 (days −3 and −1) to reduce the T cell count to <500 cells/mm$^3$ on day 0.
Maintenance:
    Mycophenolate mofetil (MMF) 50-100 mg/kg/day p.o. to maintain 12-hour whole blood trough levels at 3-6 ug/ml
    CTLA4-Ig 25 mg/kg i.v. on days −1, 0, 4, 7, 10, 14, and then weekly.

Porcine Islet Preparation and Transplantation:
Pig islet isolation is carried out shortly after removal of the pancreas from anesthetized pig donors. Porcine islets are obtained using a modification of the semi-automated method described by Ricordi, using specific collagenase blends designed for swine, lower digestion temperature, gentle injection of enzyme and virtually no mechanical shaking (Bottino et al., 2007). Purification of the islets is achieved by centrifugation on a cell processor machine (COBE 29911) on discontinuous gradients (Bottino et al., 2007, 2009). Functional properties and viability of the isolated islets are evaluated for each islet batch. In the absence of a non human primates model of autoimmune type 1 diabetes, hyperglycemia is induced by the i.v. injection of streptozotocin (STZ, Zanosar, 125-150 mg/kg). Vascular lines inserted in the carotid artery and jugular vein of the monkeys, and connected to the tether system, allow easy access for drug delivery and blood drawing and permit optimal i.v. insulin administration following diabetes induction. Intravenous glucose tolerance tests (IVGTT) and arginine stimulation tests (AST) are carried out before and after streptozotocin administration to confirm the diabetic status, and after the transplantation, to evaluate the graft response to secretagogues. On the day of transplantation, islets, following overnight culture in CMRL-1066 medium supplemented with 10% Heat-Inactivated Fetal Calf Serum, 10 mM Nicotinamide, 2 mM glutamine and Pen-Strepto, are counted, resuspended in CMRL containing 4 mg Dextrane Sulphate to prevent coagulation, and injected in the portal vein by gravity over a period of 5-10 minutes. Porcine C-peptide release, an indicator of islet cell destruction, is measured after one and two hours after islet infusion and a peak indicates the degree of initial islet cell loss due to IBMIR. Historical data accrued from previous experiments, can be used to evaluate the ability of the transgenes to prevent early islet loss. Serum C-peptide concentrations are determined using specific porcine and human antibodies that do not cross react with each other, making it possible to distinguish between endogenous and graft insulin production following xenotransplantation (Casu et al. 2008).

The early loss of islets from IBMIR can be monitored by (i) measurement of the C-peptide levels within the first 24 hours (as a marker of islet destruction), (ii) the blood glucose level, (iii) exogenous insulin requirement post-Tx (as indicators of the success of the transplant in maintaining a state of normoglycemia), (iv) presence of numerous viable islets (insulin-positive) in the liver, and (v) extent of cellular infiltration of the graft on histologic examination after necropsy.

Example 10

In Vivo Function of CD46 Transgenic Pig Islets in Diabetic Monkeys

To determine the utility of the CD46 expressing cells for treatment of diabetes in a primate, diabetes was chemically induced in cynomolgous monkeys as described in Example 9.

hCD46+ pig islet donors were derived by outcrossing from a progenitor line carrying the hCD46 transgene, a minigene under control of its endogenous promoter. Ubiquitous hCD46 expression was observed by immunofluorescent microscopy of all tissues analyzed and of isolated islets (Loveland et al., Xenotransplantation, 2004, 11:171:183). Diabetes was induced and confirmed in 9 monkey recipients as described in Example 9. Group A recipients (n=4) were transplanted with either wild-type porcine islets (n=2) or islets isolated from GTKO pigs (n=2), in numbers of 85,000 to 100,000 IEQ/kg of body weight. Group B recipients (n=5) received equal numbers of islets from hCD46+ pigs. Two group B animals were retransplanted after 49 and 91 days, respectively. Immunosuppression was identical for both groups and consisted of antithymocyte globulin for induction, anti-CD154 monoclonal antibodies and mycophenolate mofetil (MMF). Monkeys were followed until loss of graft function, or up to 3 months after transplant, except for one group B animal that was allowed >1 yr of follow-up.

Functional porcine islet survival, determined by detectable porcine C-peptide in combination with a more than 50% reduction of exogenous insulin needs, was achieved in all monkeys. In group A, islet survival lasted for 7, 20, 31, and 46 days. In group B, the use of hCD46+ islets significantly prolonged functional porcine islet survival to the full 3 months or beyond yr of follow-up, respectively (log-rank test P=0.0042). Post-transplant weekly fasting porcine C-peptide levels were comparable for groups A and B during the first 45 days (1.10±0.41 versus 1.19±0.88 ng/mL, student t-test P=0.860). After 45 days, C-peptide positivity was maintained at 0.87±0.41 ng/mL only in group B recipients.

Insulin independence was achieved in 3 of 4 Group A monkeys for a period of 5, 17, and 36 days, respectively. Four of 5 group B monkeys became insulin independent for 87, 91 92, and >396 days, respectively. During times of insulin independence, fasting blood glucose values were well controlled (group A: 91±18 mg/dL; group B: 112±22 mg/dL, student t-test P=0.250). None of the monkeys recovered endogenous beta cell function.

Histological evaluation of post-transplant livers revealed many viable porcine islets in group B animals. T cell infiltration was successfully prevented. Serum levels of anti-Gal and/or anti-nonGal antibodies did not increase in group A, nor group B monkeys, nor after re-transplant. Nevertheless, IgM, IgG, and C4d was seen on engrafted islets by histological analysis of group A livers, but only to a minimal extent on islets in group B livers.

With CD46 as the only transgene, large islet doses were still required (75,000-100,000 IEQ/kg), and there was still significant early graft loss associated with the hCD46 xenograft. In addition, the exogenous immunosuppression regime utilized is not amenable to use in human patients (see van der Windt et al., Am. J. Transplantation, 9(12):2716-2726. 2009).

Example 11

Phenotype of pCTLA4-Ig Expressing Pigs

Although the development of pCTLA4-Ig expressing animals has been suggested, these animals are severely immunocompromised. Pigs expressing CTLA4-Ig ubiquitously using a CAG enhancer/promoter were found to have an immunocompromised phenotype and were not viable in a typical husbandry environment.

Primary fetal fibroblasts (originating from Landrace/Duroc/Large White crosses) from WT or GTKO pigs were co-transfected by electroporation with a 10:1 ratio of linearized pCTLA4-Ig construct to either a pgkpuromycin$^r$ or pgkncomycin$^r$ vector. At 48 h, cells were seeded in 48-well plates at a concentration of 100-500 cells/cm$^2$, and selected with either 250 µg/ml G418 (Gibco BRL, Grand Island, N.Y.) or 0.5 µg/ml puromycin (InvivoGen, San Diego, Calif.). Selected clones were screened for the pCTLA4-Ig transgene by polymerase chain reaction (PCR), and positive clones (8 with WT background, 70 with GTKO background) were pooled and used for nuclear transfer. These cells were subject to nuclear transfer as described above. Animals were farrowed in segregated housing to minimize exposure to pathogens and received feed containing tetracycline (110 g/kg of feed) starting at birth and continuing until euthanasia. pCTLA4-Ig expression was assessed via western blot and immunofluorescence showing robust expression. Serum concentrations of pCTLA4-Ig were high, ranging from approximately 380 to 1,600 µg/ml serum.

The pCTLA4-Ig transgenic pigs and non-transgenic littermates appeared healthy for a period of approximately 2 months. At that point, the transgenic piglets began showing signs of illness, including fever, general malaise, abnormal hair growth, and, in some cases, skin lesions. In the WT/pCTLA4-Ig pigs, which had been weaned from the sows (their mothers) and housed in the whole-herd nursery these illnesses were acute and, after symptoms became evident death rapidly resulted. Most transgenic pigs succumbed to illness or required euthanasia by 10-11 weeks of age. Non-transgenic littermates in these litters remained healthy. Hematological analyses indicated that, without prophylactic treatment, transgenic pigs, in contrast to their non-transgenic littermates, had low white blood cell (WBC) counts, ranging from 53% to 71% of normal values. Total lymphocyte counts were also subnormal in these animals, ranging from 14% to 61% of normal values.

The CAG-pCTLA4-Ig transgenic pigs produced on a homozygous GTKO background, developed a more chronic illness and, despite antibiotic treatment, the health of these pigs continued to deteriorate and, at approximately 10 weeks of age, the last of these pigs was euthanized. The 4 non-transgenic littermates, raised with their CTLA4-transgenic siblings, remained healthy and vigorous (see: Phelps et al., Xenotransplantation, 16(6):477-485. 2009).

Example 12

Production of Pig Containing Five Genetic Modifications (GTKO, CD46, and Pancreatic Islet Specific TFPI, CTLA4-Ig and CD39)

Transfection of cells from fetus 548/A3 (genetic modifications: homozygous GTKO/CD46/TFPI/CTLA4-Ig) was performed to add the pREV835 (CD39) transgene. Fetal fibroblasts were transfected with the pREV835 transgene using procedures similar to those described in Example 3. Ninety-nine colonies were harvested and screened for the presence of the pREV835 transgene using procedures described in Example 5. Cells from ten positive colonies were pooled and prepared for use in nuclear transfer. Nuclear transfer was performed using the pooled pREV835 positive cells as nuclear donors and following procedures described in Example 4. Embryos were transferred to 4 recipient gilts, and 2 pregnancies were established. Ten pigs were born; four of these pigs were born alive. Genotypic analysis indicated that three of the four live born pigs contained the pREV835 (CD39) transgene in addition to the four genetic modifications from the 548/A3 line (GTKO/CD46/TFPI/CTLA4-Ig). To our knowledge, this is the first time pigs have been produced comprising more than four genetic modifications.

Example 13

Fertility of Multi-Transgenic Pigs and Stable Transmission and Co-Segregation of Multiple Transgenes to Offspring when a Multi-Transgenic Pig was Bred Naturally Natural breeding of female pig 347-2 (a pig produced by NT using 548/A3 donor cells) to a homozygous GTKO male pig, resulted in a normal pregnancy and a litter of eleven pigs born, thus demonstrating fertility of this multi-transgenic animal. Five of these pigs were born alive. Two of the live born pigs carried the two additional islet specific (548/A3 line) transgenes transmitted from their dam (TFPI and CTLA4-Ig) as well as the GTKO and CD46 genetic modifications inherent to the parent cell line. The other three offspring were positive for GTKO and CD46 only. The table below summarizes the genotype of the 347-2 offspring (determined by Southern analysis).

| | Genotype (as determined by Southern analysis) | | | |
|---|---|---|---|---|
| Animal | GTKO | CD46 | TFPI (pREV790) | CTLA4-Ig (pREV792) |
| Dam (347-2) | (+) | (+) | (+) | (+) |
| Sire | (+) | (−) | (−) | (−) |
| Offspring | | | | |
| 417-1 M | (+) | (+) | (+) | (+) |
| 417-2 M | (+) | (+) | (−) | (−) |
| 417-3 F | (+) | (+) | (−) | (−) |
| 417-4 F | (+) | (+) | (+) | (+) |
| 417-5 F | (+) | (+) | (−) | (−) |

Southern analysis indicates that all animals transgenic for TFPI are also transgenic for CTLA4Ig; this suggests that the TFPI and CTLA4-Ig transgenes co-integrated in the porcine genome, co-segregated during meiosis, and were transmitted together via breeding. Resulting offspring produced by breeding the 548A3 line carry either the two islet specific transgenes together, or neither islet specific transgene. Fluorescent in situ hybridization (FISH) analysis of offspring animal 417-4 is underway to further analyze this co-integration. In this analysis, probes for CTLA4Ig and TFPI will be labeled with distinctive fluorescent tags and hybridized with chromosomal DNA. Hybridization of both probes at a single locus will indicate that these transgenes co-integrated and will be inherited together in future generations of pigs Animal 417-4 is being raised for future breeding as well.

Example 14

ATPase Functional Assay of CD39 Positive Porcine Islet Cells

Isolation of Porcine Islets from Pig 390-1:

Pancreatic tissue was obtained from animal 390-1, a pig with five genetic modifications produced in Example 12. The pancreas was trimmed of fat and injected with cold HBSS+ 0.5 mg/ml of Collagenase P (Roche Applied Science, Indianapolis, Ind.). The pancreas was warmed to 37 C for 30 minutes. It was then placed in cold HBSS and the organ was teased apart using forceps. Dispersed tissue was run through a mesh screen (30 mesh) to remove large pieces of tissue. Pancreatic islets were purified using an Optiprep™ (Axis-Shield, Oslo, Norway) protocol. The tissue pellet was resuspended in 20 ml RPMI and 10 ml of Optiprep working solution (final concentration 1.1 g/ml) Eight ml of 1.085 Optiprep™ was overlaid followed by 10 ml of RPMI. The tubes were spun at 500×g for 5 minutes at 4 C. Islets present in the top interface were removed and a sample was stained to confirm presence of islets. Islets were plated in a 96 well plate in preparation for ATPase assay.

ATPase Assay on 390-1 Islets:

CD39 is an extracellular enzyme which catalyzes ATP and ADP to AMP (thus liberating phosphate). Therefore an ATPase chromogenic assay (QuantiChrom™ ATPase/GTPase Assay Kit, BioAssay Systems (Hayward, Calif.), which measures the liberation of phosphate, was used to determine functionality of the CD39 transgene in porcine islets, as compared to islets isolated from a wildtype pig. Fetal fibroblasts from a pig with high level ubiquitous expression of CD39 (animal 325.1) were used as a positive control.

Cells were diluted to provide confluency in a row of wells of a 96-well plate, with a 1:10 dilution in a second row of wells. All cells received one wash with Tris buffered saline (TBS). Cells were frozen overnight, thawed, and the contents of 6 confluent wells were pooled and suspended in a final volume of 100 ul TBS. This volume was split (50 ul/ea) into 2 1.5 ml Eppendorf tubes. To each tube was added:
90 ul 2× sample diluent
1.8 ul 100 mM ATP (final 1 mM concentration) or $H_2O$
38.2 ul $H_2O$ The reaction mix was incubated with shaking at 37 C for 30 minutes, and then centrifuged at 8000 rpm. Ten ul of the supernatant was mixed with 190 ul $H_2O$ (1:20 dilution). An 80 ul volume of this dilution was added to the first row of wells on a 96 well plate. Two-fold serial dilutions were made down the columns of wells for dilutions from 1:20 to 1:2560. Phosphate dilutions (0-50 uM) were prepared and added to the plate to serve as a standard curve. Malachite green reagent (200 ul) from the ATPase kit was added to each well and the plate was incubated at room temperature for 45 minutes. Readings at OD620 were performed and concentrations of released phosphate were determined by interpolation from the phosphate standard curve.

Figure 8:
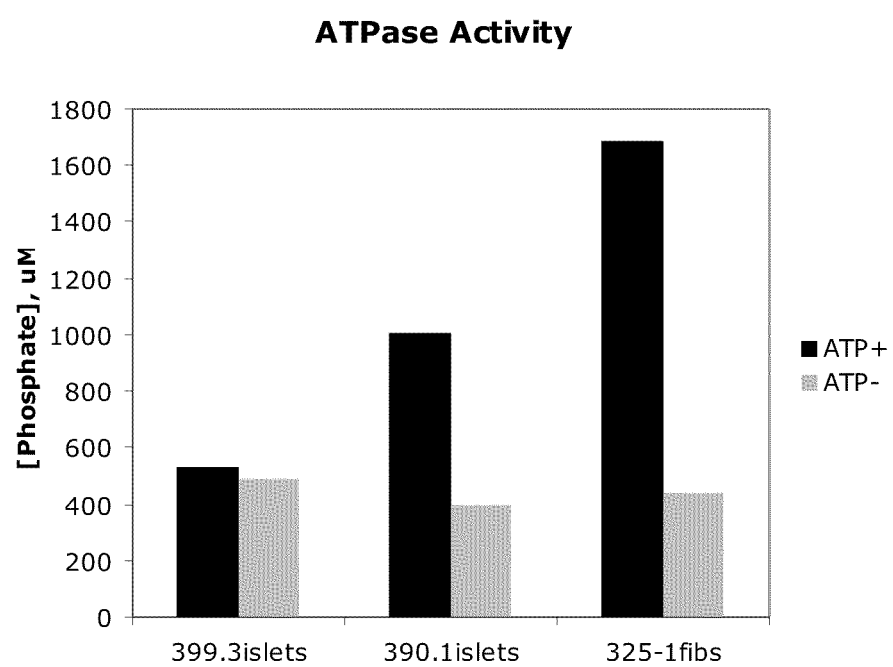
FIG. 8 illustrates released phosphate levels in islets from pig 390-1 compared to wildtype islets.

As shown in FIG. 8, islets from pig 390-1 had higher levels of released phosphate than wildtype islets, indicating functionality of the expressed CD39 transgene.

Example 15

Immunofluorescence of Pancreatic Tissue from Multi-Transgenic Pig

Figure 9:
FIG. 9 is staining results for CD46, TFPI, CTLA4-Ig, CD39, and insulin in pig 390-1
Figure 9:
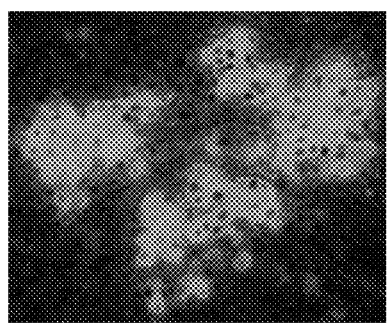
Figure 9:
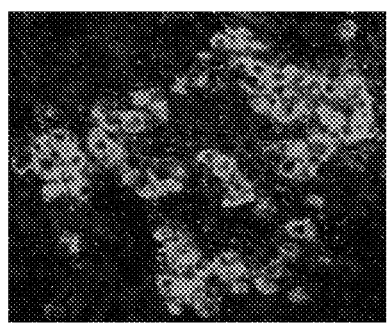
Figure 9:
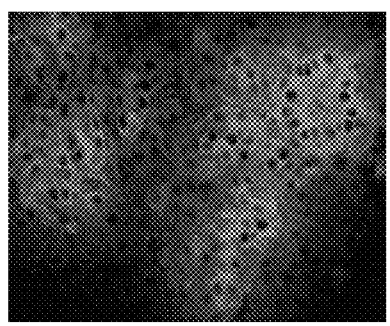
Figure 9:
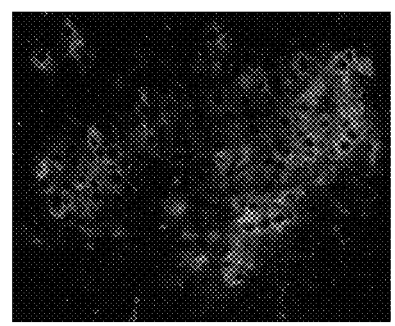

Samples of pancreatic tissue were collected from piglet 390-1 at approximately 3 months of age (genotype: GTKO, CD46, TFPI, CTLA4-Ig and CD39 transgenic) and phenotypically characterized by IF as described in Example 7. Strong staining was present for all transgenic proteins in pancreas: CD46, TFPI, CTLA4-Ig, and CD39 (FIG. 9); notably in the islet cell component. Insulin staining of islets in the tissue examined is also shown. Expression of TFPI, CTLA4-Ig and CD39 was islet-specific and was not seen in other tissues/organs tested (not shown) All isotype controls stained negative (not shown).

What is claimed is:

1. A genetically modified transgenic porcine animal, wherein the genetic modifications comprise modifications to the genome of the porcine that result in (i) the lack of any expression of functional alpha 1,3 galactosyltransferase (GTKO), (ii) incorporation of a human CD46 transgene under the control of the human CD46 promoter and expression of the human CD46 transgene in at least pancreatic islet cells and tissues; (iii) incorporation and expression of at least one immunosuppressant transgene under the control of an islet-specific promoter in the genome of pancreatic islet cells and tissues; (iv) incorporation and expression of at least one anti-coagulant transgene under the control of an islet-specific promoter in the genome of pancreatic islet cells and tissues; (v) wherein the phenotype of the porcine is characterized by specific expression of the anticoagulant and immunosuppressant transgenes in pancreatic islet cells and tissues; and (vi) wherein transgenic porcine islet cells isolated from the porcine animal produce insulin and reduce the instant blood mediated inflammatory reaction (IBMIR), in comparison to non-transgenic porcine islet cells, after transplantation into a host.

2. The porcine animal of claim 1, wherein the anticoagulant is selected from the group consisting of tissue factor pathway inhibitor (TFPI), CD39, hirudin, thrombomodulin and endothelial cell protein C receptor (EPCR).

3. The porcine animal of claim 2, wherein the anticoagulant is tissue factor pathway inhibitor (TFPI).

4. The porcine animal of claim 2, wherein the anti-coagulant is CD39.

5. The porcine animal of claim 2, wherein the anti-coagulant is selected from the group consisting of hirudin, thrombomodulin and endothelial cell protein C receptor (EPCR).

6. Pancreatic tissue derived from the porcine animal of claim 1.

7. Pancreatic cells derived from the porcine animal of claim 1.

8. The tissue of claim 6, wherein the tissue is neonatal.

9. The cells of claim 7, wherein the cells are pancreatic islets.

10. The cells of claim 7, wherein the pancreatic cells are beta cells.

11. The cells of claim 7, wherein the cells are encapsulated.

12. The porcine animal of claim 1, wherein the animal specifically expresses at least two anticoagulant transgenes in pancreatic tissue.

13. The porcine animal of claim 12, wherein the anti-coagulants are TFPI and CD39.

14. The porcine animal of claim 1, wherein the animal specifically expresses at least three transgenes in pancreatic tissue wherein the at least three transgenes are the anticoagulant transgenes TFPI and CD39 and the immunosuppressant transgene CTLA4.

15. Pancreatic tissue derived from the animal of claim 14.

16. Pancreatic cells derived from the animal of claim 14.

17. The tissue of claim 15, wherein the tissue is neonatal.

18. The cells of claim 16 wherein the cells are pancreatic islets.

19. The cells of claim 16, wherein the pancreatic cells are beta cells.

20. The cells of claim 16, wherein the cells are encapsulated.

21. The porcine animal of claim 1, wherein the immunosuppressant is selected from the group consisting of CTLA4, CIITA, CD47, HLA-E, and TRAIL.

22. The porcine animal of claim 1, wherein the immunosuppressant is CTLA4.

23. Pancreatic tissue derived from the animal of claim 21.

24. Pancreatic cells derived from the animal of claim 21.

25. The tissue of claim 23, wherein the tissue is neonatal.

26. The cells of claim 24 wherein the cells are pancreatic islets.

27. The cells of claim 24, wherein the pancreatic cells are beta cells.

28. The cells of claim 24, wherein the cells are encapsulated.

* * * * *